US007531522B2

(12) United States Patent
Peschen et al.

(10) Patent No.: US 7,531,522 B2
(45) Date of Patent: May 12, 2009

(54) ANTIBODIES, RECOMBINANT ANTIBODIES, RECOMBINANT ANTIBODY FRAGMENTS AND FUSIONS MEDIATED PLANT DISEASE RESISTANCE AGAINST FUNGI

(75) Inventors: Dieter Peschen, Geilenkirchen-Tripsrath (DE); Rainer Fischer, Monschau (DE); Stefan Schillberg, Aachen (DE); Yu-Cai Liao, Aachen (DE); Simone Dorfmüller, Aachen (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 314 days.

(21) Appl. No.: 10/512,184

(22) PCT Filed: Apr. 14, 2003

(86) PCT No.: PCT/EP03/03852

§ 371 (c)(1),
(2), (4) Date: May 10, 2005

(87) PCT Pub. No.: WO03/089475

PCT Pub. Date: Oct. 30, 2003

(65) Prior Publication Data

US 2005/0244901 A1    Nov. 3, 2005

(30) Foreign Application Priority Data

Apr. 22, 2002 (EP) .................................. 02008929
May 28, 2002 (EP) .................................. 02011807

(51) Int. Cl.
*C12P 19/30* (2006.01)
*C12P 19/34* (2006.01)
*C12N 15/00* (2006.01)
*C12N 15/64* (2006.01)
*C12N 15/76* (2006.01)
*C12N 15/87* (2006.01)
*A01H 1/00* (2006.01)

(52) U.S. Cl. .......................... 514/44; 435/89; 435/91.1; 435/91.4; 435/455; 435/458; 435/462; 435/468; 435/471; 435/490; 800/278; 800/279; 930/10

(58) Field of Classification Search ....................... None
See application file for complete search history.

(56) References Cited

U.S. PATENT DOCUMENTS 6,087,560 A    7/2000    Cornelissen et al.

FOREIGN PATENT DOCUMENTS

WO    WO 96/00783 A1    1/1996

(Continued)

OTHER PUBLICATIONS

Gan et al., (International J. of Food Microbiol. 1997. vol. 38: 191-200).*

(Continued)

*Primary Examiner*—Mark Navarro
*Assistant Examiner*—JaNa Hines
(74) *Attorney, Agent, or Firm*—Dardi & Associates, PLLC

(57) ABSTRACT

A method for the production of fungus resistant transgenic plants, plant cells or plant tissue comprising the introduction of an Ab, rAb, rAb fragment or fusion or vector of the invention or the vectors of the composition of the invention into the genome of a plant, plant cell or plant cell tissue and a transgenic plant cell comprising stably integrated into the genome a polynucleotide or vector of the invention or the vectors of the composition of the invention.

23 Claims, 2 Drawing Sheets

FOREIGN PATENT DOCUMENTS

| WO | WO 96/09398 | * | 3/1996 |
| WO | WO 96/09398 A1 | | 3/1996 |
| WO | WO 00/23593 | * | 4/2000 |
| WO | WO 00/23593 A2 | | 4/2000 |

OTHER PUBLICATIONS

Taviadoraki et al., "Transgenic plants expressing a functional single-chain Fv antibody are specifically protected from virus attack," Nature, vol. 366, pp. 469-472, Dec. 2, 1993.

Liao et al., "Characterization of a wheat class Ib chitinase gene differentially induced in isogenic lines by infection with *Puccinia graminis*," Plant Science, vol. 103, No. 2, pp. 177-187, 1994.

Schouten et al., "The C-terminal KDEL sequence increases the expression level of a single-chain antibody designed to be targeted to both the cytosol and the secretory pathway in transgenic tobacco," Plant Molecular Biology, vol. 30, pp. 781-793, 1996.

Gan et al., "The characterization of chicken antibodies raised against *Fusarium* spp. By enzyme-linked immunosorbent assay and immunoglotting," International Journal Of Food Microbiology, vol. 38, No. 2-3, pp. 191-200, 1997.

Min et al., "Characterization of recombinant scFv antibody reactive with an apical antigen of *Eimeria acervulina*," Biotechnology Letters, vol. 23, No. 12, pp. 949-955, Jun. 2001.

Grover et al., "Removal of Vascuolar Targeting Signal from Class I Vasuolar Chitinase leads to its Extracellular Secretion in Transgenic Tobacco," Journal of Plant Biochemistry and Biotechnology, vol. 10, No. 2, pp. 139-142, Jul. 2001.

Chen et al., "Expression of Engineered Antibodies in Plants: A Possible Tool for Spiroplasma and Phytoplasma Disease Control," Phytopathology, vol. 88, No. 12, pp. 1367-1371, Dec. 1998.

Min et al., "Synthetic construct for anti-*Eimeria acervulina* spical protein ScFv antibody, clone 6D12," Database Accession No. AJ300836, 2 pages, Jan. 23, 2002.

Peschen et al., "Synthetic construct for anti *Fusarium* ScFv antibody, clone CWP2", EMBL Accession No. AJ517190, 2 pages, Nov. 29, 2002.

Peschen Et Al., "Fusion proteins comprising a *Fusarium*-specific antibody linked to antifungal peptides protect plants against a fungal pathogen", *Nature Biotechnology*, 22(6):Jun. 2004.

* cited by examiner

ANTIBODIES, RECOMBINANT ANTIBODIES, RECOMBINANT ANTIBODY FRAGMENTS AND FUSIONS MEDIATED PLANT DISEASE RESISTANCE AGAINST FUNGI

RELATED APPLICATION

This application claims priority to PCT Application No. PCT/EP03/03852 filed Apr. 14, 2003 and European Application Nos. 02008929.8 filed Apr. 22, 2002 and 02011807.1 filed May 28, 2002.

FIELD OF THE INVENTION

Molecular biotechnology has provided powerful new measures for the control of plant diseases. Antibody engineering is a novel approach to create pathogen-resistant plants, which is based on the expression of antibodies (Ab), recombinant Abs (rAbs), rAb fragments or fusions that inactivate pathogens and pathogen proteins. Antibody-based resistance can create plants that are resistant to pathogens and do not require the undesirable and expensive chemical controls currently used in agriculture. Pathogenic fungi are the most devastating of plant diseases. The interaction between fungi and plant consists of very complex mechanisms. To protect plants by using. Abs, rAb, rAb fragments and fusions containing antifungal peptides or proteins (AFPs) is the present invention of controlling fungal plant diseases. This invention is related to the genetic engineering of plants with fungal specific Abs, rAb, rAb fragments and/or fungal inhibiting fusions with this Ab derivates, which blocks stages of the fungal life cycle, the fungal infection, the fungal replication or spreading within a plant with the goal of receiving resistant agriculture and ornamental plants.

BACKGROUND OF THE INVENTION

Plant disease constitutes a major and ongoing threat to human food stocks and animal feed. Most crop plants are regularly exposed to one or more pathogen(s) that can cause incredible damage resulting in substantial economical losses every year. Attack by pathogens, such as viruses, bacteria, fungi, nematodes and insects is a severe economic problem, which impacts all economically important crops, for example rice, soybean, sweet potato, wheat, potato, grape, maize and ornamental plants as cyclamen or carnation. Current protective measures rely heavily on chemical control measures for pathogens, which have undesirable environmental consequences. Natural based resistance against fungi often not exists.

A more effective approach to protecting plants from pathogen attack is to create plants that are endogenously resistant to fungi. However, plant breeders have limited sources of resistance genes against plant diseases. This can now be achieved using genetic engineering techniques, by providing the plant with genetic information required for affecting the pathogens and for being resistant to the disease caused by the pathogen. For example, in the case of a fungal pathogen, the host plant is resistant if it has the ability to inhibit or retard the growth of a fungus, the symptoms of fungal infection or the life cycle of the fungus, including its spreading. "Resistant" is the opposite of "susceptible" and may be divided into three levels:
1. Full
2. Medium
3. Partial resistance A plant may be considered fully resistant when it shows no symptoms on infection and there is no evidence of pathogen reproduction and spreading. The host plant may be resistant to the establishment of infection, pathogen reproduction and/or pathogen spreading and transmission.

An alternative way to protect plants against pathogen infection is the generation and expression of Ab, rAb, rAb fragments and their fusions with AFPs. Pathogen-specific rAb targeted to different compartments of plant cells or different plant organs overcome many of the problems mentioned before and confer a broader spectrum of resistance to disease. To achieve this, rAb against the target proteins have to be generated by cloning the corresponding antibody heavy and light chain genes from hybridoma cells, synthetic, semi-synthetic and immunocompetent phage display, peptide display or ribosome display libraries; or by the generation of fully synthetic designer antibodies or pathogen specific peptide ligands. This is followed by subsequent modification and rAb expression in different compartments of heterologous hosts such as bacteria, yeast, algae, baculovirus infected insect cells, mammalian cells and plants. For example, antibodies and antibody-fusion proteins binding to conserved functional domains of fungal proteins or other components involved in fungal infection, growth and spreading can be used to inactivate such targets inside or outside the plant cell through immunomodulation. The feasibility of expressing recombinant antibodies for the generation of resistance has been shown recently for plant viruses (see for review Schillberg et al., 2001).

The potential of recombinant antibodies to interfere with the infection of a plant virus was demonstrated in 1993 (Tavladoraki et al., 1993). In this case, the constitutive expression of a cytosolic scFv against the coat protein of artichoke mottled crinkle virus in transgenic tobacco caused a reduction in viral infection and a delay in symptom development. This result supported the hypothesis that transgenically expressed antibodies or antibody fragments recognizing critical epitopes on structural or non-structural proteins of invading viruses may interfere with viral infection and confer viral resistance. Further support of this hypothesis was demonstrated by Voss et al. (1995). *Nicotiana tabacum* cv. *Xanthi* nc plants secreting full-size antibodies binding to intact TMV particles displayed a reduced number of necrotic local lesions when challenged with TMV. The results indicated that the number of infection events was directly correlated to the amount of secreted full-size antibodies and the local lesions were reduced by 70% when levels of apoplast targeted antibodies reached 0.23% of total soluble protein in transformed plants.

Cytosolic expression of the scFv fragment derived from this TMV-specific full-size antibody was evaluated as an alternative to protect plants from virus infection (Zimmermann et al., 1998). The TMV specific scFv accumulated to very low levels in the plant cytosol (0.00002% of total soluble protein). Nevertheless, the low cytosolic scFv accumulation led to remarkably enhanced resistance although the amounts of expressed scFv were approximately 20,000-fold lower when compared to elite plants secreting high levels of the TMV-specific full-size antibody (Zimmermann et al., 1998). Transgenic plants accumulating the TMV-specific scFv in the cytosol showed >90% reduction of local lesion number and a significant portion showed resistance in systemic infection assays. This phenomenon could be explained by the fact that upon infection only a few TMV molecules are needed to enter the cytosol of a plant cell to initiate viral replication and cell-to-cell movement of progeny RNA. Presumably, the low amount of intracellular expressed scFv is sufficient for neutralizing the invading virions either by interfering in viral uncoating or assembly of progeny virions.

A different approach for engineering disease resistant crops was developed by integrating antiviral antibody fragments in the plasma membrane in planta. TMV specific scFv fragments were efficiently targeted to the plasma membrane of tobacco cells by a heterologous mammalian transmembrane domain and the membrane anchored scFv fusion proteins, facing to the apoplast, retained antigen binding and specificity (Schillberg et al., 2000). Transgenic plants expressing membrane targeted scFv fusion proteins were resistant to TMV infection, demonstrating that membrane anchored anti-viral antibodies were functional in vivo, offering a powerful method to shield plant cells from invading pathogens.

The engineering of bacterial resistance is another interesting topic of commercial interest. Many different genetic strategies have been used to generate plants resistant to bacterial diseases, including enhancing natural plant defense, artificially inducing cell death at the site of infection and the expression of antibacterial proteins or peptides (Mourgues et al., 1998). Recently, it has been demonstrated that antibody-based resistance is also useful against bacterial diseases. Le Gall et al. (1998) have shown that expression of an scFv specific for the stolbur phytoplasma major membrane protein provided a way to control phytoplasma diseases. Stolbur phytoplasma are strictly restricted to the sieve tubes within the phloem tissues. Therefore, the phytoplasma specific scFvs were expressed through the secretory pathway. Transgenic tobacco shoots expressing phytoplasmaspecific scFv top-grafted on tobacco plants heavily infected by the phytoplasma grew free of symptoms while non-transgenic tobacco shoots showed severe stolbur symptoms.

These studies demonstrate the potential of heterologously expressed recombinant antibodies to protect plants against virus and bacteria. However none of these publication describe that Ab, rAb, rAb fragments for its own or Ab, rAb, rAb fragments fused to antifungal peptides or proteins expressed in plants can yield resistance against pathogenic fungi.

Pathogenic fungi are the most devastating of plant diseases and most challenging for antibody-based resistance approaches. Fungal infections affect crops by destroying plants and seeds and by contaminating the harvested crop with fungal toxins. When fungal pathogens infect plants, they parasitize the host plant for nutrients and their invasive mycelia spread throughout the host. The fungi secrete proteins essential for fungal pathogenesis as part of an intimate relationship between the host plant and pathogen for penetration and nutrition. These proteins and any others like surface structures are suitable targets that could be neutralized by expression of recombinant antibodies. The antibodies may have to be transported to the site of the infection since the fungi should be inactivated prior to degradation of the host cell wall. This could reduce the damage caused by fungi without the environmental pollution that occurs when fungicides are used to control such diseases.

In mammals, antibody-based protection against fungal pathogens has been shown. (Yuan et al., 1998). In plants, symptom development for avocado, mango, and banana infected with *Colletotrichum gloeosporioide* was delayed using polyclonal antibodies that bound fungal pectate lyase (Wattad et al., 1997). To date, there is no evidence that an antibody produced in transgenic plants can protect it from fungal infection. An attractive idea is to use antibodies as a carrier to target linked anti-fungal (poly)peptides to the fungal cell surface, where they destroy the hyphae. Moreover, antibodies may directly contribute to increase crop yield by neutralizing fungal toxins in infected crop harvests. A wide variety of fungal metabolites are toxic to plants, animals and humans, having dramatic effects on animal and human health, in addition to their involvement in plant pathogenesis (Desjardins & Hohn, 1997).

SUMMARY OF THE INVENTION

One object of the invention is to provide the means and methods for protecting plants, in particular monocotyledonous and dicotyledonous agricultural crops and ornamental plants, against fungi in a more effective and environmentally sensitive manner.

As will be described herein below, the above-mentioned object is met according to the invention by any one of the embodiments of the independent claims and claims depending thereon. A system is provided for the expression of fungus specific rAb and parts thereof, or by fusing antibodies or parts thereof to secondary metabolites, toxins, peptides, proteins, or enzymes having activity against fungus.

The object of the invention is accomplished by a method for the production of fungus resistant transgenic plants, plant cells or plant tissues comprising the introduction of a polynucleotide coding for an Ab, rAb, rAb fragment or fusion protein into the genome of a plant, plant cell or plant tissue. In particular, the fungus is from the species *ascomyceta*, more particularly the fungus is *Fusarium* ssp., *Sclerotinia sclerotiorum, Phoma lingam* and *Verticillium dahliae*. In the following it is referred to either of these species. When explaining the invention in more detail however, reference to *Fusarium* ssp., *Sclerotinia sclerotiorum, Phoma lingam* and *Verticillium dahliae* is not limiting the disclosure of the invention. The skilled person is able to transfer the disclosure concerning the embodiment for the above mentioned species.

The present invention also relates to a transgenic plant cell comprising stably integrated in the genome a polynucleotide coding for an Ab, rAb, rAb fragment or fusion protein.

In addition, the present invention relates to a transgenic plant or plant tissue comprising the above-described plant cells or obtainable by the method of the invention. Encompassed are also the transgenic plants wherein the fusion protein or Ab, rAb, rAb fragment are made functional against pathogens by in vivo assembly after co-transformation of at least two independent plant expression constructs or after sexual crossing to form hybrid offspring from two parental plants expressing one or more of the domains of the fusion protein or the Ab, rAb, rAb fragment, or any other form of genetic recombination. Preferably, the transgenic plant of the invention displays improved resistance against a pathogen that the wild type plant was susceptible to.

Furthermore, the present invention relates to harvestable parts and propagation material of a plant of the invention comprising plant cells of the invention.

Subject of the present invention is also a polynucleotide in form of a vector, plasmid, clean DNA-fragment and or an expression casette. The vector of the invention comprises preferably a polynucleotide operatively linked to regulatory sequences for the expression of a fusion protein, rAb or domains thereof in a host cell. Typically, the regulatory sequence of the invention is selected from the group consisting of constitutive, chimeric, tissue specific and/or inducible synthetic and cryptic promoters.

Preferred scFvs for performing the invention are having the nucleotide sequence ID No.1, 2, 3, 4, 5, 6, 7, 8, 9, 10 and 11 and the amino acid sequence ID No. 26, 27, 28, 29, 30, 31, 32, 33, 34, 35 and 36. The scFvs may contain an N- and/or C-terminal tag(s). A tag can be selected from the group of tags comprising c-myc, his6, his5, tag54, FLAG, HA, HSV-, T7, S, strep, and/or an E-tag.

Preferred AFPs for performing the invention are having the nucleotide sequence ID No 12, 13, 14, 15, 16 and 17 and amino acid sequence ID No. 37, 38, 39, 40, 41 and 42. If the AFPs are expressed alone without the scFv fusion partner the ORF may contain an N- and/or C-terminal tag(s).

Preferred AFP-scFv fusions for performing the invention are having the nucleotide sequence ID No. 12 or 13 or 14 or 15 or 16 or 17 plus 19 plus 1 or 2 or 3 or 4 or 5 or 6 or 7 or 8 or 9 or 10 or 11 and amino acid sequence ID No. 37 or 38 or 39 or 40 or 41 or 42 plus 44 plus 26 or 27 or 28 or 29 or 30 or 31 or 32 or 33 or 34 or 35 or 36. AFP-scFvs may contain an N- and/or C-terminal tag(s).

Subject of the invention is also an anti-fungal protein or peptide (AFP) portion. Preferably they are selected from the group of proteins consisting of chitinases, glucanases, lactoferrin, ACE, AG, MBP, RS, indolicidin, apidaecin, pyrrhocoricin, histatin 5, and combinations thereof.

Also a fusion protein is subject of the invention. The fusion protein of the invention is an immune-fungicide having an affinity portion against fungal surface structure(s) and an anti-fungal protein portion or an anti-fungal peptide portion.

The fusion protein of the invention comprises a targeting signal in particular N- and/or C-terminal. If present, the targeting is for example a signal for secretion, membrane anchoring, apoplast targeting, vacuolar targeting and ER retention.

The fusion protein comprises an affinity portion against fungal surface(s). Preferably, the affinity portion of the fusion protein of the invention is in form of a scFv having the amino acid sequence. ID No. 26 or 27, or 28 or 29 or 30 or 31 or 32 or 33 or 34 or 35 or 36. In a special embodiment of the invention scFvs according to the invention comprise an N- and/or C-terminal tag (s).

Special AFP-scFv fusion proteins in the invention comprise or consist of the amino acid Seq. ID. No. 44 which is framed by at least one of the Seq. ID. No. 37 or 38 or 39 or 40 or 41 or 42 either N- or C-terminal or N- and C-terminal. Alternatively, Seq. ID No. 44 may be framed by at least one of the amino acid sequences with Seq ID No 26 or 27 or 28 or 29 or 30 or 31 or 32 or 33 or 34 or 35 or 36 No. and/or comprising or consisting of the amino acid sequences with the Seq. ID. No. 37 or 38 or 39 or 40 or 41 or 42 at the C- and/or N-terminal of Seq. ID No. 44. Subject of the present invention are therefore also AFP-scFv fusion proteins having the amino acid Seq. ID. No. 37 or 38 or 39 or 40 or 41 or 42 linked N- and/or C-terminal to Seq. ID No. 44 and/or comprising the amino acid sequence 26 or 27 or 28 or 29 or 30 or 31 or 32 or 33 or 34 or 35 or 36 linked to Seq. ID No. 44 at N- or C-terminal position, i.e. if a AFP sequence selected from the group of sequences with Seq ID. No.: 37-42 is N-terminal of Seq. ID. No. 44, then a scFv sequence selected out of the group of sequences 26-36 are C-terminal of Seq. Id. No. 44, and vice versa, if a scFv sequence selected out of the group of sequences 26-36 is N-terminal of Seq. ID. No. 44, then a AFP sequence selected from the group of sequences with Seq ID. No.: 37-42 is C-terminal of Seq. ID. No. 44. The AFP-scFv of the invention may comprise a N- and/or C-terminal tag(s), i.e. the tag can be N-terminal of the AFP sequence and/or directly C-terminal of the AFP sequence, and/or N-terminal of the scFv sequence and/or C-terminal of the scFv sequence.

Polynucleotides coding for AFP-scFv fusion proteins mentioned above have the nucleotide Seq. ID. No. 12, 13, 14, 15, 16 or 17 linked either 3' or 5' to Seq. ID No 19 and comprising Seq. ID. No. 1, 2, 3, 4, 5, 6, 7, 8, 9, 10, or 11 or having the nucleotide Seq. ID. No. 1, 2, 3, 4, 5, 6, 7, 8, 9, 10, or 11 linked either 3' or 5' to Seq. ID. No. 19 and/or comprising Seq. ID. No. 12, 13, 14, 15, 16 or 17.

The novel Ab, rAb, rAb fragment or fusions of the invention are also subject of the invention. In another embodiment the present invention relates to the use of the described Ab, rAb, rAb fragment or fusions of the invention in agriculture for the protection of a plant against the action of a fungus.

The present invention is also related to compositions comprising a polynucleotide of the invention.

In a still further embodiment, the present invention relates to a kit comprising fusion proteins, Ab, rAb, rAb fragment, polynucleotides, compositions or molecular fungicides.

The Ab, rAb, rAb fragments or fusions can be targeted to the apoplast or to organelles and plant cell compartments or immobilized and membrane anchored by addition of targeting sequences and/or membrane anchors.

According to the invention it is possible to regenerate for example *Fusarium oxysporum* f.sp. *matthiolae* resistant *Arabidopsis thaliana* plants which express *Fusarium* specific scFvs and scFvs fused to antifungal peptides or proteins. *F. oxysporum* f.sp. *matthiolae* specific scFvs are also binding to other *Fusarium* ssp. like *F. graminearum*, *F. culmorum*, *F. solani*, *F. avenaceum* and *F. oxysporum* f.sp. *cyclaminis*. These *Fusarium* ssp. pose a large threat for crops and ornamental plants, which can only be protected by using high priced fungicides which have major negative impacts on the environment.

According to this invention it is also possible to regenerate *Brassica napus* plants which express *Verticillium dahliae* and *Phoma lingam* specific scFvs fused to antifungal peptides or proteins which show a significant resistance to *Phoma lingam*.

Some aspects of the present invention will be described herein below.

DETAILED DESCRIPTION OF THE INVENTION

Antibody and Antibody Fragment

The term "antibody" and "antibody fragment" is used to denote polypeptide chain(s) which exhibit a strong monovalent, bivalent or polyvalent binding to a given epitope or epitopes. The antibodies may be generated by any suitable technology, such as hybridoma technology, or ribosome display, or phage display, of natural naïve origin, or immunized origin, semi-synthetic or fully synthetic libraries or combinations thereof. The term "antibody" is also used to denote designer antibodies. These antibody polypeptides are encoded by an immunoglobulin gene or immunoglobulin genes, or fragments thereof which specifically bind the given epitope or epitopes. The recognized immunoglobulin genes include the κ and λ light chain genes, the μ, δ, γ, α and ε constant regions as well as all immunoglobulin variable regions from vertebrate, camelid, avian and pisces species. The term antibody, as used herein, includes in particular those antibodies synthesized or constructed de novo using recombinant DNA methodology, such as recombinant full-size antibodies, dimeric secretory IgA antibodies, multimeric IgM antibodies, F(ab')2-fragments, Fab-fragments, Fv-fragments, single chain Fv-fragments (scFvs), bispecific scFvs, diabodies, single domain antibodies (dAb), minibodies (Vaughan and Sollazzo, 2001) and molecular recognition units (MRUs). Antibody sequences may be derived from any vertebrate, camelid, avian or pisces species using recombinant DNA technology, or also by using synthetic, semi-synthetic and naïve or immunocompetent phage and ribosome display libraries, gene shuffling libraries, molecular evolution, and fully synthetic designer antibodies. In this invention, the antibodies are generated against specific pathogen or host plant epitopes that are involved in the pathogen growth, reproduction or life cycle.

The term "pathogen" is used to denote viral or virus like organisms, bacteria, mycoplasmas, fungi, insects or nematodes that affect the germination of seed, growth, development, reproduction, harvest, yield or utility of a plant.

The term AFP (anti fungal peptide or polypeptide) refers to an activity, which may be peptide or polypeptide encoded, that affects the reproduction or growth of a fungus and/or any stages of its life cycle. In the case of fungal pathogens, this includes germination of spores, adhesion to the plant surface, entry into the plant, formation of appressoria and haustoria, penetrating a plant cell tissue or spreading. Antibodies or recombinant proteins in themselves are also considered toxic when they affect the fungus by binding to it and or host proteins that are utilized by a pathogen during its growth, reproduction, life cycle or spreading.

Monoclonal antibodies (Köhler and Milstein, 1975) can be raised against almost any epitope or molecular structure of a pathogen or host protein using several techniques. The most common method is the hybridoma technique starting with immunocompetent B lymphocytes from the spleen or thymus which are obtained after immunization with native antigen, recombinant antigen, antigen fusion proteins, antigen domains or by in vitro or genetic immunization. In addition, recent advances in molecular biology techniques now permit the use of cloned recombinant antibody fragments and antibodies derived from mice and other organisms than the mouse. Suitable recombinant antibody fragment(s) include the complete recombinant full-size antibodies, dimeric secretory IgA antibodies, multimeric IgM antibodies, the F(ab')2 fragment, the Fab-fragment, the Fv-fragment, single chain antibody fragments (scFvs), single binding domains (dAbs), a bivalent scFv (diabody), minibody, and bispecific scFv antibodies where the antibody molecule recognises two different epitopes, which may be from the pathogen or the host or both the pathogen and the host, triabodies or other multispecific antibodies and any other part of the antibody such as, molecular recognition units (MRUs), which show binding to the target epitopes. Genes encoding these suitable recombinant antibody fragment(s) may be derived from vertebrates, camelids, avian or pisces species.

Also, single chain antibodies that have affinities for pathogen or host structures and proteins can be identified using phage display libraries or ribosome display libraries, gene shuffled libraries, which can be constructed from synthetic, semi-synthetic or naïve and immunocompetent sources. Phage display and suitable techniques can be used to specifically identify antibodies, or fragments thereof, with the desired binding properties. Using recombinant antibody technology it is possible to identify antibodies or fragments that are highly specific for a single pathogen, or which recognize a consensus epitope conserved between several pathogens, where the antibodies will have a broad specificity against pathogens. The durability and effect of antibody mediated resistance can be improved by i) recombinant antibody affinity maturation, ii) CDR randomization and selection, iii) stabilization by framework optimization of a selected pathogen specific antibody, iv) bi-specific antibody expression, v) the generation of antibody fusion proteins, or vi) the expression of antibodies in combinations with others that may potentiate their individual effects. For example, surface plasmon resonance as employed in the BIAcore system can be used to increase the efficiency of phage displayed antibodies selections, yielding a high increment of affinity from a single library of phage antibodies which bind to an epitope of a pathogen with desired on- and off-rates.

The recombinant antibodies can be identified and utilized according to methods that are familiar to anyone of ordinary skill in the art.

This invention describes antibodies or fragments thereof which recognize structures of the fungi directly or indirectly leading to resistance or partial resistance when expressed alone or when expressed as a chimeric fusion protein coupled to an antifungal activity and coexpression of several of these constructs.

Antibodies can be generated that recognize fungal-specific epitopes or host plant-specific epitopes which have a role in the life cycle of a fungus. These antibodies or fragments thereof may be inactivating in themselves or in combination with one or more other antibodies, or an antifungal substance (AFP), or in combination with a carrier, transmembrane domain or signal peptide. Importantly, plant pathogen resistance can be enhanced by the co-expression of multiple antibodies.

Antifungal Peptides and Proteins

Antifungal peptides and proteins (AFPs) that have a detrimental effect on a fungus during its life cycle and/or an effect on the pathogen during plant infection, fungus growth or spreading. This includes antifungal substances that specifically kill an infected host cell and so limit the spread and development of a disease.

Suitable antifungal substances include the following:

Antifungal peptides or proteins, which are specific for fungi and mediates toxicity ACE, AG, MBP, RS, Lactoferricin, Chitinase or others e.g. Indolicidin, Apidaecin, Pyrrhocoricin or Histatin 5 (Zasloff, 2002)

Antifungal peptides or proteins like ACE, AG, MBP, RS, or Lactoferricin that integrate into the fungal cell walls and form small pores and openings, resulting in an inversion of the ion gradient between the inside of the cell and the surrounding medium and subsequent death of the fungus.

Chitinases and glucanases are involved in the defense mechanism of plants. They hydrolyze the 1,4-bonds of N-acetyl-D-glucoseaminpolymers resulting in a collapse of the fungal chitin structure.

Binding domains, such as antibodies defined above specifically recognizing an epitope of a plant fungus. Moreover, rAb and rAb fragments can also be fused to other toxins that inactivate the fungal pathogen, for example by killing the host cell where the fungal pathogen is growing and has entered the appropriate plant cell compartment including the cytosol, for example RIPs (Ribosome inactivating proteins) which enter the cytosol and are among the most potent cytotoxins known.

In principle all antibodies, proteins, peptides and enzymes that have a specificity and activity, that may or may not be enzymatic, which are able to interfere with fungal life cycles are suitable as part of the present constructs.

In a preferred embodiment of the present invention said enzyme is chitinase or glucanase, ACE, AG, MBP, RS, or Lactoferricin or active fragments thereof either singly or in any combination(s).

Constructs

Gene constructs may comprise the following or any combination of the following and may be encoded on one or more plasmids or clean DNA fragments: Gene constructs may comprise a nucleotide sequence or nucleotide sequences encoding complete recombinant full-size antibodies, dimeric secretory IgA antibodies, multimeric IgM antibodies, the F(ab')2 fragment, the Fab-fragment, the Fv-fragment, single chain antibody fragments (scFvs) (FIG. 1), single binding domains (dAbs), a bivalent scFv (diabody), minibody, bispecific scFv antibodies where the antibody molecule recognizes two different epitopes that may come from the fungus or the host or both, triabodies and any other part of the antibody (molecular recognition units (MRUs)) which shows binding to the target epitopes. Genes encoding these suitable recombinant antibody fragment(s) may be derived from vertebrates, camelids, avian or pisces species.

In the constructs according to the invention, the antibody is fused to a complete sequence of an antifungal agent or a part thereof which still has activity, or which is still functionally active (FIG. 1). The antibody or antibody fragment can be fused N- or C-terminal or N- and C-terminal to the antifungal agent. Also, the chimeric protein may be encoded by nucleotide sequences on one or more constructs and may be assembled in vivo by the plant or expression organisms protein assembly and translation machinery. The chimeric protein can also be obtained by biochemical assembly or in vitro or in vivo assembly of the chimeric fusion protein subunits using the cell's endogenous protein assembly and targeting machinery.

The antibody, antibodies or fragments thereof are fused directly to the antifungal agent or linked by a flexible spacer, which does not interfere with the structure or function of the two proteins. Such flexible linkers include copies of the (Glycine-Glycine-Glycine-Glycine-Serine)*n* linker, where n is 1 to 4 or more copies of the linker unit, the Genex 212 and 218 linker and the flexible linker peptide of *Trichoderma reesei* cellobiohydrolase I (CBHI) (Turner et al., 1997).

The fusion construct comprising antibody, antibodies or fragments thereof, a linker and an antifungal agent or a part thereof or a fusion construct of antibody, antibodies or fragments thereof and antifungal agent or a part thereof can comprise an additional targeting sequence or a membrane anchor.

Optionally, a fusion construct has one or more suitable restriction enzyme sites included between the targeting sequence, antibody or fragments thereof, the linker and the antifungal agent or a part thereof, in order to allow flexible exchange of the different parts of the construct. Optionally, if no linker is present, at least one suitable restriction enzyme site is included between the antibody or fragments thereof and the antifungal agent or a part thereof.

Protein constructs having the amino acids of Seq. ID. No. 26 to 36, 47 to 50, 62 to 72 and polynucleotide constructs having the nucleotide sequences of Seq. ID. No. 1 to 11, 22 to 25 and 51 to 61 are also subject of the present invention.

Kits

In addition, the present invention relates to a kit e.g. a dip-stick-kit, an ELISA kit or protein chip comprising the above-described Ab, rAb, rAb fragments and their corresponding AFP fusion proteins. Said kit can also comprise the above described Ab, rAb, rAb fragments carrying at their C- or N-terminus a tag and/or are fused to a detection enzyme. Detection enzymes can be alkaline phosphatase and/or horse radish peroxidase. The kit of the invention may advantageously be used for carrying out diagnostic tests to detect the fungal infection in crops or ornamental plants as well as harvestable materials thereof.

Target Pathogens

The target pathogens are plant fungi e.g. *Fusarium* species, *Verticillium dahliae, Sclerotinia sclerotiorum* and *Phoma lingam* as selected member of ascomycota. Fungal plant pathogens cause devastating yield losses in crops and ornamental plants worldwide. The earliest food producers used mechanical means to control fungal outbreaks. Several fungal diseases could be overcome by the classic plant breeding. Moreover fungicides are used to control fungal pathogens, but they are very expensive and encompass health and environmental risks.

Genetic engineering is an alternative to chemical control, especially when there is no genetical resource for the breeding of new resistant varieties available. Several genes capable of controlling fungal plant pathogens have been inserted and expressed in plants. Most research efforts have been directed toward overexpression of the enzyme classes containing chitinases and glucanases (Benhamou, 1995).

To date, antibody-based resistance has focused on pathogenic virus, bacterial and nematodes, but the use of Ab, rAb, rAb fragments and their corresponding AFP fusions to protect plants against pathogenic fungi has not been investigated.

35S CaMV: enhanced 35S Cauliflower Mosaic Virus (CaMV) promoter; UT: Chalcone synthase 5' untranslated region (Zimmermann et al., 1998); LP: plant codon optimized original mouse leader peptide of the rAb24 light chain for targeting of recombinant proteins to the apoplast (Voss et al., 1995); AFP=antifungal peptid or protein; (G4S)2: 10 amino acid glycine-serine-linker (GGGGSGGGGS) (Seq. ID. No. 44); scFv: single chain fragment; tag: c-myc epitope tag sequence (Seq. ID. No. 45) and/or 6 histidine residue epitope tag sequence (Seq. ID. No. 46); TCaMV: CaMV termination sequence; restriction sites: EcoRI, NdeI, NcoI, SalI, SfiI, NotI.

FIG. 2: In vitro inhibition test.

*F. graminearum* and *F. oxysporum* f.sp. *matthiolae* spores were germinated o/n at 28° C., bacterially produced recombinant anti-*Fusarium* scFv fragments, AFPs and AFP-scFv fusion proteins were added and inhibition of fungal growth was monitored after 14 days of incubation at 28° C. The scFv PIPP, which is directed against human chorionic gonadotropin (hCG), was used as a control. The amount of recombinant proteins added to the germinated spores is indicated. 0.02% (w/v) Na-azid in serial dilutions was used as inhibition control, 2TY medium containing 100 μg/ml ampicillin was used as control.

FIG. 3 shows the phage display and bacterial expression vector pHENHi containing an integrated scFv. pelB: leader sequence for localisation in the periplasm; VH: variable region of the heavy chain, 218*: modified 218 18 amino acid linker with a mutation from a tyrosin to a prolin; VL: variable region of the light chain; c-myc: epitope tag sequence (Seq. ID. No. 45); his6: 6 histidine residue epitope tag sequence (Seq. ID. No. 46); restriction sites: SfiI, NcoI, BstEII, AscI, NotI, SalI; Amber*=stop codon; gene III: phage protein.

The following examples are given to better describe the practice and applications of the present invention and should not be considered to be a limiting description nor interpreted to limit the scope and applications of the present invention. Those skilled in the art will recognize that various modifications can be made to the methods and genes described here without substantively departing from the spirit and scope of the present invention.

EXAMPLE 1

Generation of *Fusarium*-specific scFvs by Hybridoma Technology

1. Antigens (secreted proteins from fungal hyphae) were prepared from *Fusarium graminearum*.
2. Mice were separately immunized with the antigens.
3. Spleen cells from immunized mice were isolated and hybridomas were generated. Several limiting dilution steps were performed to isolate hybridoma cell lines that secrete antibodies specifically recognizing fungal antigens.
4. mRNA from selected hybridoma cell lines was isolated and cDNA generated using reverse transcriptase. cDNA sequences encoding the antibody variable heavy and light chains (VH and VL) were amplified by PCR and cloned into the pHEN4II and pHENHi vector.
5. The final scFv construct scFv SPIII7 (Seq. ID. No. 4) was used for bacterial and plant expression.

EXAMPLE 2

Generation of *Fusarium*-specific scFvs by Phage Display

Figure 3:
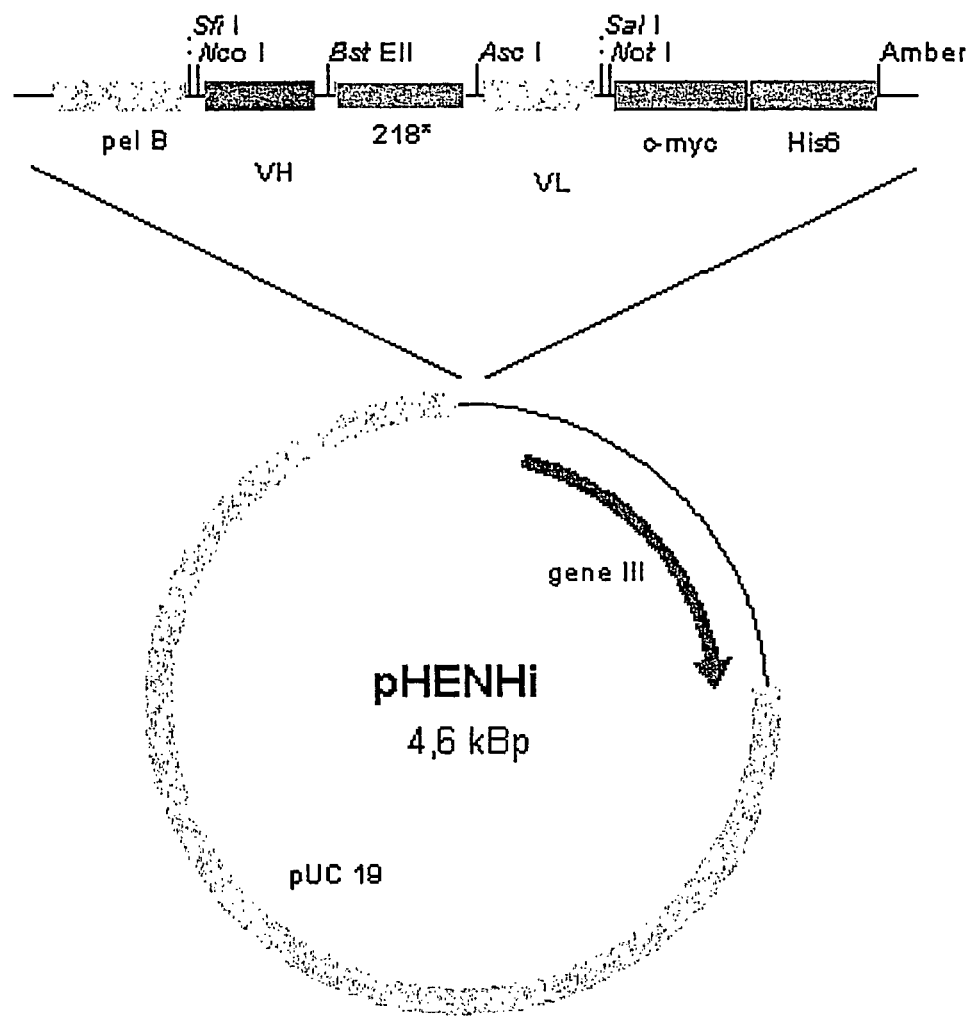

1. Antigens were prepared from *Fusarium graminearum*. The following antigens were prepared: cell wall proteins, germinated spores and fresh plate culture washing proteins.
2. Chicken were immunized separately with the antigens.
3. mRNA from chicken spleen cells was isolated and cDNA generated using reverse transcriptase. Variable domains of heavy and light chains (VH and VL) were amplified by PCR and cloned via unique restriction sites separately into the phage display vector pHENHi (FIG. 3) to generate a VH and a VL library, pHENHi contained a pelB signal sequence for targeting of recombinant proteins to the bacterial periplasm and a C-terminal c-myc (Seq. ID. No. 20) and his6 tag (Seq. ID. No. 21). Subsequently, VL fragments were cut out from the VL library and ligated into the VH library to assemble the scFv cDNA whereas VH and VL cDNAs were connected by a linker peptide. The libraries obtained from the chickens immunized with the three antigens were mixed.
4. A phage library derived from the different scFv libraries (step 3) were generated and specific scFv fragments were identified by library panning using the three different fungal antigens described in step 1. After each panning round eluted phages were used for infection of *E. coli* and the new phage libraries were prepared for the next round of panning. After three rounds of panning the best binders were selected, by ELISA.
5. The final scFv genes scFv CWPD2 (Seq. ID. No. 1) panned against cell wall proteins, scFv FPCWPA5 (Seq. ID. No. 3) panned against fresh plate culture washing proteins and scFv SGB3 (Seq. ID. No. 2) panned against germinated spores were expressed in bacteria and plants.

EXAMPLE 3

Characterization of scFvs

1. ScFv CWPD2 (Seq. ID. No. 1), scFv FPCWPA5 (Seq. ID. No. 3), scFv SGB3 (Seq. ID. No. 2) and scFv SPIII7 (Seq. ID. No. 4) cDNAs from the examples 1 and 2 in PHENHi were bacterially expressed, purified by IMAC and characterized by immunoblot, ELISA and immunofluorescence microscopy.
2. Integrity of purified scFvs was verified by immunoblot.
3. ELISA confirmed that the scFv CWPD2 (Seq. ID. No. 26), scFv FPCWPA5 (Seq. ID. No. 28), scFv SGB3 (Seq. ID. No. 27) and scFv SPIII7 (Seq. ID. No. 29) including cmyc (Seq. ID. No. 45) and his6 tag (Seq. ID. No. 46) bound to all three fungal antigens, cell wall proteins, germinated spores and, fresh plate culture washing proteins. They bound to the surface of germ tubes and mycelia from different *Fusarium* ssp., e.g. *F. graminearum, F. culmorum, F. solani, F. oxysporum* f.sp. *cyclaminis, F. oxysporum* f.sp *lycopsersici* and *F. oxysporum* f.sp. *matthiolae*.
4. Immunofluorescence microscopy verified binding of the scFv CWPD2 (Seq. ID. No. 26), scFv FPCWPA5 (Seq. ID. No. 28), scFv SGB3 (Seq. ID. No. 27) and scFv SPIII7 (Seq. ID. No. 29) to the surface of germ tubes and mycelia from different *Fusarium* ssp. e.g. *Fusarium graminearum, F. culmorum, F. solani, F. oxysporum* f.sp. *cyclaminis, F. oxysporum* f.sp *lycopsersici* and *F. oxysporum* f.sp. *matthiolae*.

EXAMPLE 4

Construction of AFP and AFP-ScFv Fusions

Figure 1:
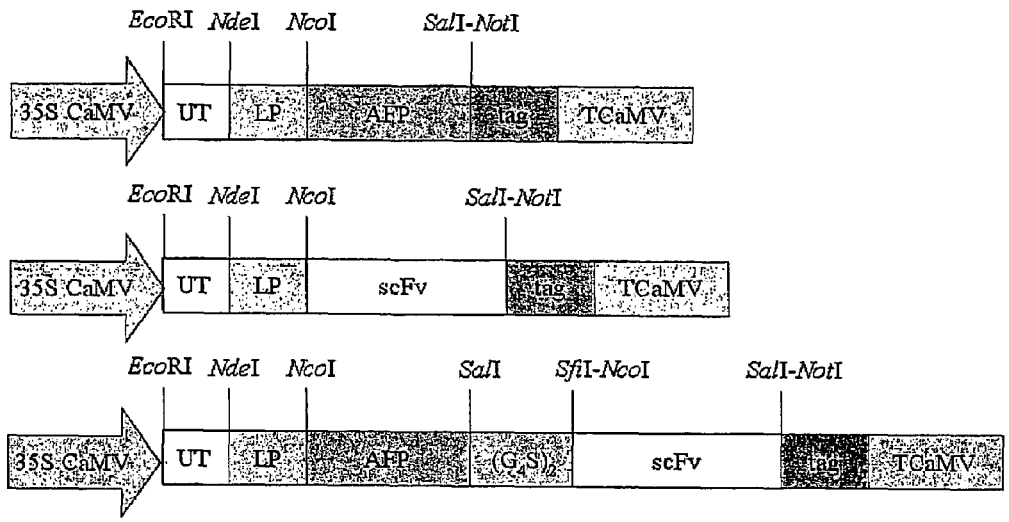
FIG. 1: Plant expression cassettes for expression of AFP, scFv and AFP-scFv fusion proteins in plants.

1. Antifungal peptides and proteins AG (Seq. ID. No. 15), RS (Seq. ID. No. 13), Lactoferricin (Seq. ID. No. 14) and chitinase (Seq. ID. No. 12) (FIG. 1, Table 1) were amplified by PCR using specific primers containing restriction sites for subcloning and fusion to scFvs.
2. Nucleotide sequences for antifungal peptides and proteins AG, RS, Lactoferricin and chitinase were fused to scFv CWPD2 (Seq. ID. No. 1) via a (Gly4Ser)2 (Seq. ID. No. 19) linker to generate fusion constructs AG-scFv CWPD2 (Seq. ID. No. 51), RS-scFv CWPD2 (Seq. ID. No. 52), Lactoferricin-scFv CWPD2 (Seq. ID. No. 53), and chitinase-scFv CWPD2 (Seq. ID. No. 54).
3. Antifungal peptides and proteins AG, RS, Lactoferricin and chitinase and fusion constructs AG-scFv CWPD2, RS-scFv CWPD2, Lactoferricin-scFv CWPD2 and chitinase-scFv CWPD2 were cloned into pHENHi containing a pelB signal sequence and a C-terminal cmyc (Seq. ID. No. 20) and his6 tag (Seq. ID. No. 21), expressed in *E. coli* and used for in vitro inhibition tests (example 5).

EXAMPLE 5

In Vitro Inhibition Tests for Fungal Growth

Figure 2:
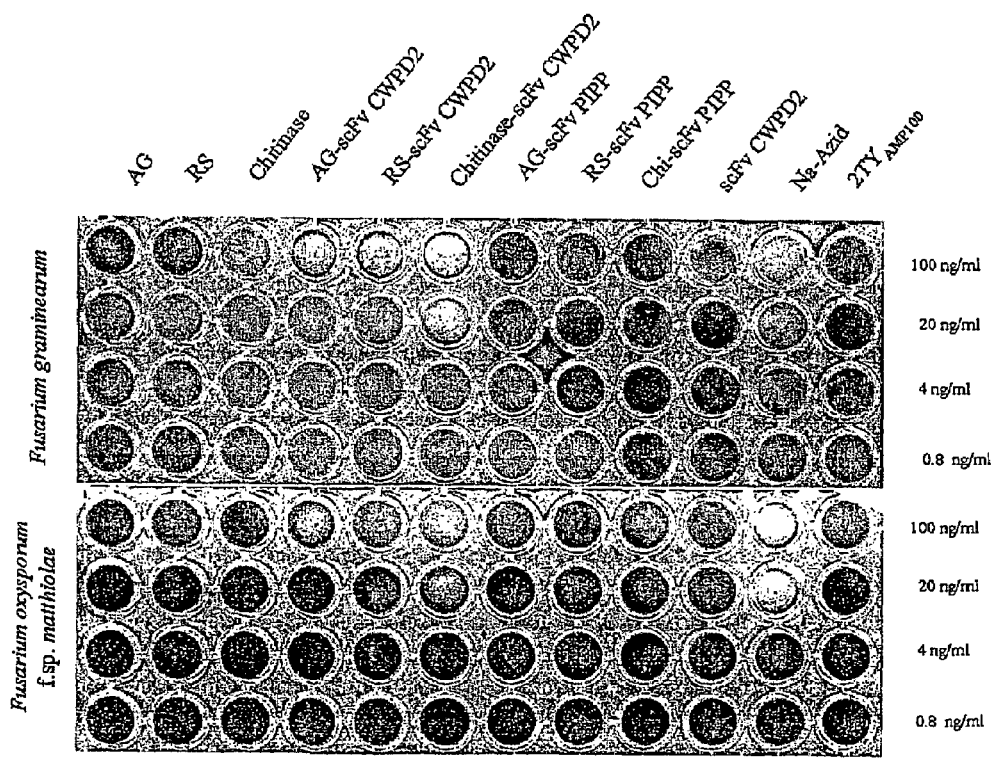

1. To analyze the biological effect of bacterial expressed scFv CWPD2 (Seq. ID. No. 26), AFPs AG (Seq. ID. No. 40), RS (Seq. ID. No. 38), and chitinase (Seq. ID. No. 37), and fusion proteins AG-scFv CWPD2 (Seq. ID. No. 62), RS-scFv CWPD2 (Seq. ID. No. 63), and chitinase-scFv CWPD2 (Seq. ID. No. 65), (from example 3 and 4) were used in in vitro inhibition tests.
2. *F. graminearum* and *F. oxysporum* f.sp. *matthiolae* spores were germinated o/n at 28° C., bacterially produced recombinant anti-*Fusarium* scFv fragments, AFPs and AFP-scFv fusion proteins were added in serial dilutions from 100 ng/ml to 0.8 ng/ml and inhibition of fungal growth was monitored after 14 days of incubation at 28° C. The scFv PIPP, a scFv against human chorionic gonadotropin (hCG), was used as control.
3. The results of the inhibition tests demonstrated that AG-scFv CWPD2 (Seq. ID. No. 62), RS-scFv CWPD2 (Seq. ID. No. 63), and chitinase-scFv CWPD2 (Seq. ID. No. 65), including cmyc (Seq. ID. No. 45) and his6 tag (Seq. ID. No. 46) inhibit fungal growth in vitro (FIG. 2).

EXAMPLE 6

Transient Expression in Plants

1. The following scFv, AFP and AFP-scFv cDNAs were cloned into the plant expression vector pTRAkc, a modified version of the pSS vector (Voss et al., 1995): scFv CWPD2 (Seq. ID. No. 1), AG (Seq. ID. No. 15), RS (Seq. ID. No. 13), Lactoferricin (Seq. ID. No. 14), chitinase (Seq. ID. No. 12), AG-scFv CWPD2 (Seq. ID. No. 51), RS-scFv CWPD2 (Seq. ID. No. 52), Lactoferricin-scFv CWPD2 (Seq. ID. No. 53), chitinase-scFv CWPD2 (Seq. ID. No. 54), RS-scFv PIPP, AG-scFv PIPP. The scFv PIPP, a scFv against human chorionic gonadotropin (hCG), was used as control. The expression cassette in pTRAkc contained the enhanced 35S promoter from Cauliflower Mosaic Virus (CaMV), the 5' untranslated region from chalcone synthase, the plant codon-optimized original mouse leader signal of the rAb24 light chain (seq. ID. No. 18) (Vaquero et al., 1999), a C-terminal his6 tag (Seq. ID. No. 21) and the CaMV termination sequence.

2. *Agrobacterium tumefaciens* were transformed by N2 transformation with all the constructs derived from step 1 and 2.

3. Expression of scFvs, AFPs and AFP-scFv fusion proteins in plant cells was verified by transient transformation of tobacco leaves and their integrity and binding activity to the corresponding fungal antigens were demonstrated by immunoblot and ELISA.

EXAMPLE 7

Stable Transformation of *Arabidopsis thaliana* and Characterization of Transgenic Plants 1. *Arabidopsis thaliana* plants were transformed by the floral dipping using recombinant agrobacteria from example 6.

2. Regenerated transgenic plants were analyzed by PCR to verify integration of the transgene into the plant genome.

3. Accumulation of the recombinant proteins was verified by immunoblot or ELISA.

4. The binding of the plant-produced scFv CWPD2 (Seq. ID. No. 26) and the fusion proteins AG-scFv CWPD2 (Seq. ID. No. 62), RS-scFv CWPD2 (Seq. ID. No. 63), Lactoferricin-scFv CWPD2 (Seq. ID. No. 64), chitinase-scFv CWPD2 (Seq. ID. No. 65) including his6 tag (Seq. ID. No. 46) was analyzed by ELISA using of *F. graminearum* and *F. oxysporum* f.sp. *matthiolae* germinated spores as an antigen.

EXAMPLE 8

Resistance Tests of Transgenic *Arabidopsis thaliana* Plants

1. The activity of the recombinant proteins in generating resistance against fungi is assayed by fungal infection bioassays on transgenic *Arabidopsis* plants, generated in example 7 by using *Fusarium oxysporum* f.sp. *matthiolae*.

2. Transgenic *Arabidopsis thaliana* plants producing AG-scFv CWPD2 (Seq. ID. No. 62), RS-scFv CWPD2 (Seq. ID. No. 63), Lactoferricin-scFv CWPD2 (Seq. ID. No. 64), and chitinase-scFv CWPD2 (Seq. ID. No. 65) including his6 tag (Seq. ID. No. 46) were used for the bioassay. The results demonstrated that AG-scFv CWPD2, RS-scFv CWPD2, Lactoferricin-scFv CWPD2 and chitinase-scFv CWPD2 conferred significant resistance to *Fusarium oxysporum* f.sp. *matthiolae* compared to non-transgenic *Arabidopsis thaliana* plants.

EXAMPLE 9

Transformation of Rice and Wheat and Regeneration of Transgenic Plants 1. scFv cDNAs from scFv CWPD2 (Seq. ID. No. 1), scFv FPCWPA5 (Seq. ID. No. 3), scFvSGB3 (Seq. ID. No. 2) and scFv SPIII7 (Seq. ID. No. 4) and AFP cDNA from AG (Seq. ID. No. 15), RS (Seq. ID. No. 13), Lactoferricin (Seq. ID. No. 14) and chitinase (Seq. ID. No. 12) and AFP-scFv cDNAs of AG-scFv CWPD2 (Seq. ID. No. 51), RS-scFv CWPD2 (Seq. ID. No. 52), Lactoferricin-scFv CWPD2 (Seq. ID. No. 53) and chitinase-scFv CWPD2 (Seq. ID. No. 54) were integrated into the plant expression vector pAHC25. pAHC25 contained the ubiquitin promoter and NOS terminator, the chalcone synthase 5' untranslated region and plant codon-optimized LP signal sequence of the murine rAb24 light chain (Seq. ID. No 18) and a C-terminal cmyc (Seq. ID. No. 20) and his6-tag (Seq. ID. No 21).

2. Rice and wheat were stable transformed by particle bombardment.

3. Stable transformed rice and wheat plants were regenerated.

TABLE 1

Comparison of *Fusarium*-specific scFv, antifungal peptides or proteins (ATP) and AFP-scFv fusions expressed in *E. coli* and *Arabidopsis thaliana* and bioassays with transgenic *A. thaliana* plants.

| | Construct | *E. coli* expression[1] | In Vitro Assay[2] | Recombinant protein accumulation in *A. thaliana*[3] | Bioassay[4] |
|---|---|---|---|---|---|
| scFv | scFv CWPD2 | + | − | + | S |
| | scFv FPCWPA5 | + | − | + | S |
| | scFv SGB3 | + | − | + | S |
| | scFv SPIII7 | + | − | + | S |
| AFP | AG | + | − | + | S |
| | RS | + | − | + | S |
| | Lactoferricin | − | − | + | S |
| | Chitinase | + | − | + | S |
| AFP-scFv fusion protein | AG-scFv CWPD2 | + | + | + | R |
| | RS-scFv CWPD2 | + | + | + | R |
| | Lactoferricin-scFv CWPD2 | − | − | + | R |
| | Chitinase-scFv CWPD2 | + | + | + | R |

[1]recombinant protein accumulation was detected by immunoblot and/or ELISA;
[2]bacterially expressed recombinant proteins were used to analyze inhibition of fungal growth in vitro;
[3]recombinant protein accumulation in stable transformed *Arabidopsis* plants was detected via immunoblot and ELISA;
[4]transgenic *Arabidopsis* plants were infected with *F. oxysporum* f.sp. *matthiolae* and monitored for resistance three weeks post inoculation.
S: susceptible plant;
R: resistant plant;
n.d.: not done;
+: positive;
−: negative

EXAMPLE 10

Generation of *Sclerotinia sclerotiorum*, *Phoma lingam* and *Verticillium dahliae*-specific scFvs by Hybridoma Technology 1. Antigens (fungal hyphae and secreted proteins from fungal hyphae) were prepared from *Sclerotinia sclerotiorum*, *Phoma lingam* and *Verticillium dahliae*.

2. Mice were separately immunized with a mix of prepared antigens of each individual fungus species.

3. Spleen cells from immunized mice were isolated and hybridomas were generated. Several limiting dilution steps were performed to isolate hybridoma cell lines that secrete antibodies specifically recognizing fungal antigens.

4. mRNA from selected hybridoma cell lines was isolated and cDNA generated using reverse transcriptase. cDNA sequences encoding the antibody variable heavy and light chains (VH and VL) were amplified by PCR and cloned into the pHEN4II vector.

5. The final scFv construct scFv SS2 (Seq. ID. No. 11) (*Sclerotinia sclerotiorum*-specific), scFv PL2 (Seq. ID. No. 9) (*Phoma lingam*-specific) and scFv VD2 (*Verticillium dahliae*-specific) were used for bacterial and plant expression.

EXAMPLE 11

Generation of *Phoma lingam*-specific scFvs by Chicken Phage Display

1. Antigens (fungal hyphae and secreted proteins from fungal hyphae) were prepared from *Phoma lingam*.

2. Chickens were immunized separately with the antigens.

3. mRNA from chicken spleen cells was isolated and cDNA generated using reverse transcriptase. Variable domains of heavy and light chains (VH and VL) were amplified by PCR and cloned via unique restriction sites separately into the phage display vector pHEN4II to generate a VH and a VL library. Subsequently, VL fragments are cut out from the VL library and ligated into the VH library to assemble the scFv cDNA whereas VH and VL cDNAs are connected by a linker peptide. The libraries derived from the chicken immunized with fungal hyphae and secreted proteins from fungal hyphae were kept separated.

4. Phage libraries derived from the different scFv libraries (step 3) were generated and specific scFv fragments were identified by library panning using the fungal antigen which was used for immunization described in step 1 and 2.

After each panning round eluted phages were used for infection of *E. coli* and the new phage libraries were prepared for next round of panning. After three rounds of panning the best binders were selected by ELISA.

5. The final scFv genes scFv PLp9 (Seq. ID. No. 10) from the secreted proteins of fungal hyphae library panned against secreted proteins of fungal hyphae was expressed in bacteria and plants.

EXAMPLE 12

Generation of *Verticillium dahliae*-specific scFvs by Mouse Phage Display

1. Antigens (fungal hyphae, fungal cell wall fragments, spores and secreted proteins from fungal hyphae) were prepared from *Verticillium dahliae*.

2. Mice were immunized separately with a mix of two of the antigens (fungal hyphae and secreted proteins from fungal hyphae).

3. mRNA from mice spleen cells was isolated and cDNA generated using reverse transcriptase. Variable domains of heavy and light chains (VH and VL) were amplified by SOE-PCR and cloned via unique restriction sites into the phage display vector pHEN4II to generate a scFv library connected by a linker peptide.

4. A phage library derived from the scFv library (step 3) was generated and specific scFv fragments were identified by library panning using the fungal antigen described in step 1. After each panning round eluted phages are used for infection of *E. coli* and the new phage libraries were prepared for next round of panning. After three rounds of panning the best binders were selected by ELISA.

5. The final scFv genes scFv VDcw (Seq. ID. No. 6) from the library panned with fungal cell wall fragments, scFv VDM1 (Seq. ID. No. 7) and scFv VDM2 (Seq. ID. No. 8) from the library panned with fungal hyphae are expressed in bacteria and plants.

EXAMPLE 13

Characterization of scFvs Expressed in Bacteria 1. scFv SS2 (Seq. ID. No. 36), scFv PL2 (Seq. ID. No. 34), scFv VD2 (Seq. ID. No. 30), scFv PLp9 (Seq. ID. No. 35), scFv VDcw (Seq. ID. No. 31), scFv VDM1 (Seq. ID. No. 32) and scFv VDM2 (Seq. ID. No. 33) cDNAs from the examples 10, 11 and 12 were cloned in pSIN for bacterial expression. pSIN contained a pelB signal sequence for targeting of recombinant proteins to the bacterial periplasm and a C-terminal c-myc (Seq. ID. No 20) and his6 tag (Seq ID. No. 21).

2. Bacterially expressed scFvs were purified by IMAC and characterized by immunoblot, ELISA and immunofluorescence microscopy.

3. Integrity of purified scFvs was verified by immunoblot.

4. Immunoblot confirmed that scFv PL2 (Seq. ID. No. 34) including cmyc (Seq. ID. No. 45) and his6 tag (Seq. ID. No. 46) bound to a 36.5 kDA and a 25 kDA protein band in the secreted protein preparation from the fungal hyphae of a virulent *Phoma lingam* pathotype. ScFv SS2 (Seq. ID. No. 36) including cmyc (Seq. ID. No. 45) and his6 tag (Seq. ID. No. 46) bound to a 45 kDA protein band in the secreted protein preparation from fungal hyphae of *Sclerotinia sclerotiorum*. ScFv VD2 (Seq. ID. No. 30) including cmyc (Seq. ID. No. 45) and his6 tag (Seq. ID. No. 46) bound to a 32.5 kDa, scFv VDM2 (Seq. ID. No. 33) including cmyc (Seq. ID. No. 45) and his6 tag (Seq. ID. No. 46) to a 47.5 kDA protein band in the secreted protein preparation of fungal hyphae from *Verticillium dahliae*.

5. ELISA confirmed that the scFv VD2 (Seq. ID. No. 30) and scFv VDM2 (Seq. ID. No. 33) both including cmyc (Seq. ID. No. 45) and his6 tag (Seq. ID. No. 46) bound to all four *Verticillium dahliae* fungal, antigens, fungal hyphae, fungal cell wall fragments, spores and secreted proteins from fungal hyphae. ScFv VDcw (Seq. ID. No. 31) including cmyc (Seq. ID. No. 45) and his6 tag (Seq. ID. No. 46) bound to three of the *Verticillium dahliae* fungal antigens (fungal hyphae, fungal cell wall fragments and spores) and cross-reacts with *Phoma lingam* fungal hyphae and *Sclerotinia sclerotiorum* fungal hyphae and fungal cell wall fragments. ScFv VDM1 (Seq. ID. No. 32) including cmyc (Seq. ID. No. 45) and his6 tag (Seq. ID. No. 46) only bound to *Verticillium dahliae* fungal hyphae. ScFv PL2 (Seq. ID. No. 34) and scFv PLp9 (Seq. ID. No. 35) both including cmyc (Seq. ID. No. 45) and his6 tag (Seq. ID. No. 46) bound to secreted proteins from fungal hyphae of a virulent *Phoma lingam* pathotype. ScFv SS2 (Seq. ID. No. 36) including cmyc (Seq. ID. No. 45) and his6 tag (Seq. ID. No. 46) bound to *Sclerotinia sclerotiorum* secreted proteins from fungal hyphae and intracellular proteins from fungal hyphae.

5. Immunofluorescence microscopy demonstrated binding of the scFv VD2 (Seq. ID. No. 30), scFv VDM1 (Seq. ID. No. 32), scFv VDM2 (Seq. ID. No. 33) and scFv VDcw (Seq. ID. No. 31) all including cmyc (Seq. ID. No. 45) and his6 tag (Seq. ID. No. 46) to the surface of germ tubes and fungal hyphae from *Verticillium dahliae*. ScFv VDcw (Seq. ID. No. 31) including cmyc (Seq. ID. No. 45) and his6 tag (Seq. ID. No. 46) bound to the surface of germ tubes and fungal hyphae from *Phoma lingam*. ScFv PL2 (Seq. ID. No. 34) and scFv PLp9 (Seq. ID. No. 35) both including cmyc (Seq. ID. No. 45) and his6 tag (Seq. ID. No. 46) stained intracellular vesicles in the fungal hyphae of a virulent pathotype of *Phoma lingam*.

EXAMPLE 14

Characterization of scFvs Expressed in Planta

1. The scFv SS2 (Seq. ID. No. 11), scFv PL2 (Seq. ID. No. 9), scFv VD2 (Seq. ID. No. 5), scFv PLp9 (Seq. ID. No. 10), scFv VDcw (Seq. ID. No. 6), scFv VDM1 (Seq. ID. No. 7) and scFv VDM2 (Seq. ID. No. 8) cDNAs from the examples 10, 11 and 12 were cloned into the plant expression vector pTRAkc, a modified version of the pSS vector (Voss et al., 1995). The expression cassette in pTRAkc contained enhanced 35S promoter from Cauliflower Mosaic Virus (CaMV), the 5' untranslated region from chalcone synthase, the plant codon-optimized original mouse LP signal sequence of the rAb24 light chain (Seq. ID. No. 18) (Vaquero et al., 1999), a C-terminal his6 tag (Seq. ID. No. 21), a SEKDEL ER-retention signal and the CaMV termination sequence (FIG. 1). 2. *Agrobacterium tumefaciens* were transformed by N2 transformation with all the constructs derived from step 1. Expression of scFvs in plant cells was demonstrated by transient transformation of tobacco leaves.

3. Integrity of in planta expressed scFvs was demonstrated by immunoblot.

4. ScFv VDM1 (Seq. ID. No. 32) and scFv PLp9 (Seq. ID. No. 35) both including his6 tag (Seq. ID. No. 46) and SEKDEL sequence were purified by IMAC and characterised by ELISA.

5. ELISA confirmed that scFv VDM1 (Seq. ID. No. 32) including his6 tag (Seq. ID. No. 46) and SEKDEL tag only bound to *Verticillium dahliae* fungal hyphae. ScFv PLp9 (Seq. ID. No. 35) including his6 tag (Seq. ID. No. 46) and SEKDEL sequence bound to secreted proteins from fungal hyphae of a virulent *Phoma lingam* pathotype.

EXAMPLE 15

Construction of AFP and AFP-scFv Fusions

1. The sequences of antifungal peptides and proteins ACE, AG, MBP, RS and chitinase (Seq. ID. No. 17, 15, 16, 13 and 12) were amplified by PCR using specific primers containing restriction sites for subcloning and fusion to scFvs.

2. Antifungal peptides and proteins ACE, AG, MBP, RS and chitinase (Seq. ID. No. 17, 15, 16, 13 and 12) were fused to scFv SS2 (Seq. Id. No. 11), scFv PL2 (Seq. Id. No. 9), scFv VD2 (Seq. Id. No. 5), scFv PL2 (Seq. ID. No. 9), scFv PLp9 (Seq. ID. No. 10), scFv VDM1 (Seq. ID. No. 7), scFv VDM2 (Seq. ID. No. 8) and scFv VD cw (Seq. ID. No. 6) via a (Gly4Ser)2 linker (Seq. ID. No. 19) to generate 42 different (a combination of 7 scFv and 6 antifungal peptides and proteins) fusion constructs.

3. Antifungal peptides and proteins ACE, AG, MBP and RS (Seq. ID. No. 17, 15, 16, 13 and 12,) and fusion constructs chitinase-scFv VD2 (Seq. ID. No. 55), AG-scFv VD2 (Seq. ID. No. 56), RS-scFv VDcw (Seq. ID. No. 57), AG-scFv VDM1 (Seq. ID. No. 58), RS-scFv VDM2 (Seq. ID. No. 59), ACE-scFv PL2 (Seq. ID. No. 60) and MBP-scFv PLp9 (Seq. ID. No. 61) were used for plant transformation.

EXAMPLE 16

Transient Expression of AFP, AFP-scFv and Constructs in Tobacco Plants 1. cDNAs from the antifungal proteins and petides (Seq. ID. No. 17, 15, 16, 13 and 12) and all 42 different (a combination of 7 scFv and 6 antifungal peptides and proteins) AFP-scFv were integrated into the plant expression vector pSS (Voss et al., 1995). pSS contained the CaMV35S promoter, the chalcone synthase 5' untranslated region, the plant codon-optimized LP signal sequence of the murine rAb24 light chain (Seq. ID. No. 18) (Vaquero et al., 1999) a C-terminal c-myc (Seq. ID. No. 20) and his6 tag (Seq. ID. No. 21) and the pACaMV terminator.

2. *Agrobacterium tumefaciens* were transformed by N2 transformation with all the constructs derived from step 1.

3. Expression of AFPs and AFP-scFv fusion proteins in plant cells was verified by transient transformation of tobacco leaves and their integrity and binding activity to the corresponding fungal antigens were demonstrated by immunoblot.

EXAMPLE 17

Transformation of *Brassica napus*, Regeneration and Characterisation of Transgenic Plants 1. cDNAs from antifungal peptides and proteins ACE, AG, MBP and RS (Seq. ID. No. 17, 15, 16, 13 and 12) and fusion constructs chitinase-scFv VD2 (Seq. ID. No. 55), AG-scFv VD2 (Seq. ID. No. 56), RS-scFv VDcw (Seq. ID. No. 57), AG-scFv VDM1 (Seq. ID. No. 58), RS-scFv VDM2 (Seq. ID. No. 59), ACE-scFv PL2 (Seq. ID. No. 60) and MBP-scFv PLp9 (Seq. ID. No. 61) were integrated into the plant expression vector pLHSS. pLHSS contained the CaMV35S promoter, the chalcone synthase 5' untranslated region, the plant codon-optimized LP signal sequence of the murine rAb24 light chain (Seq. ID. No. 18) (Vaquero et al., 1999) a C-terminal c-myc (Seq. ID. No. 20) and his6 tag (Seq. ID. No. 21) and the pACaMV terminator. This vector is based on the pLH9000 Vector (GenBank: AF458478).

2. *Brassica napus* were stable transformed by agrobacteria mediated transformation.

3. Stable transformed *Brassica napus* plants were regenerated.

4. Regenerated transgenic plants were analyzed by PCR to demonstrate integration of the transgene into the plant genome.

5. Accumulation of the recombinant proteins was demonstrated by immunoblot.

EXAMPLE 18

Resistance Tests of Transgenic *Brassica napus* Plants

1. The activity of the recombinant proteins in generating resistance against fungi was assayed by fungal infection bioassays on transgenic *Brassica napus* plants, generated in example 17, by using *Phoma lingam*.

2. Transgenic *Brassica napus* plants producing ACE, AG, RS, MBP (Seq. ID. No. 42, 40, 38, 41) or chitinase-scFv VD2 (Seq. ID. No. 66) including cmyc (Seq. ID. No. 45) and his6 tag (Seq. ID. No. 46) were used for the bioassay. The results demonstrated that the AFP alone conferred resistance to

*Phoma lingam* compared to non-transgenic *Brassica napus* plants. The AFP-scFv fusion conferred significant higher resistance to *Phoma lingam* compared to the AFP-transgenic and non-transgenic *Brassica napus* plants.

EXAMPLE 19

Transformation of *Solanum tuberosum*, Regeneration and Characterisation of Transgenic Plants 1. cDNAs from the antifungal protein chitinase (Seq. ID. No. 12) and fusion constructs chitinase-scFv VD2 (Seq. ID. No. 55), AG-scFv VDM1 (Seq. ID. No. 58), RS-scFv VDM2 (Seq. ID. No. 59), ACE-scFv PL2 (Seq. ID. No. 60) and MBP-scFv PLp9 (Seq. ID. No. 61) were integrated into the plant expression vector pSS (Voss et al., 1995). pSS contained the CaMV35S promoter, the chalcone synthase 5' untranslated region, the plant codon-optimized LP signal sequence of the murine rAb24 light chain (Seq. ID. No. 18) (Vaquero et al. 1999) a C-terminal c-myc (Seq. ID. No. 20) and his6 tag (Seq. ID. No. 20,) and the pACaMV terminator.

2. *Solanum tuberosum* was stable transformed by agrobacteria mediated transformation.

3. Stable transformed *Solanum tuberosum* plants were regenerated.

4. Regenerated transgenic plants were analyzed by PCR to demonstrate integration of the transgene into the plant genome.

REFERENCES

Benhamou, N. 1995. Immunocytochemistry of plant defense mechanisms induced upon microbial attack. Microsc. Res. Tech. 31: 63-78.

Desjandins A. E. and T. M. Hohn. 1997. Mycotoxins in Plant Pathogenesis. Molecular Plant-Microbe Interactions. 10:147-152.

Köhler, G., and C. Milstein. 1975. Continuous cultures of fused cells secreting antibody of predefined specificity. Nature. 256:495-497.

Le Gall, F., Bove, J. M., and Garnier, M. 1998. Engineering of a single-chain variable-fragment (scFv) antibody specific for the stolbur phytoplasma (Mollicute) and its expression in *Escherichia coli* and tobacco plants. Appl Environ Micro. 64: 4566-4572.

Mourgues, F., Brisset, M. N., and Chevreau, E. 1998. Strategies to improve plant resistance to bacterial diseases through genetic engineering. TIBTECH 16: 203-210.

Schillberg, S., S. Zimmermann, K. Findlay and R. Fischer. 2000. Plasma membrane display of anti-viral single chain Fv fragments confers resistance to tobacco mosaic virus. Molecular Breeding. 6:317-326.

Schillberg, S., S. Zimmermann, M.-Y. Zhang and R. Fischer. 2001. Antibody-based resistance to plant pathogens. Transgenic Research. 10:1-12.

Tavladoraki, P., E. Benvenuto, S. Trinca, D. DeMartinis, and P. Galeffi. 1993. Transgenic plants expressing a functional scFv antibody are protected from virus attack. Nature. 366:469-472.

Turner, D. J., M. A. Ritter, and A. J. George. 1997. Importance of the linker in expression of single-chain Fv antibody fragments: optimisation of peptide sequence using phage display technology. J Immunol Methods. 205:43-54.

Voss, A., M. Niersbach, R. Hain, H. J. Hirsch, Y. C. Liao, F. Kreuzaler, and R. Fischer. 1995. Reduced virus infectivity in *N. tabacum* secreting a TMV-specific full size antibody. Mol. Breeding. 1:39-50.

Vaquero, C., Sack, M., Chandler, J., Drossard, J., Schuster, F., Monecke, M., Schillberg, S., and Fischer, R. 1999. Transient expression of a tumor-specific single-chain fragment and a chimeric antibody in tobacco leaves. Proc Natl Acad Sci USA 96: 11128-33.

Vaughan C K. and Sollazzo, M 2001. Of minibody, camel and bacteriophage. Comb Chem High Throughput Screen 2001 4:417-30

Wattad, C., Kobiler, D., Dinoor, A., and Prusky, D. 1997. Pectate lyase of *Colletotrichum gloeosporioides* attacking avocado fruits—cDNA cloning and involvement in pathogenicity. Physiological & Molecular Plant Pathology 50: 197-212.

Yuan, R., Clynes, R., Oh, J., Ravetch, J. V., and Scharff, M. D. 1998. Antibody-mediated modulation of *Cryptococcus neoformans* infection is dependent on distinct Fc receptor functions and IgG subclasses. J Exp Med 187: 641-648.

Zimmermann, S., S. Schillberg, Y. C. Liao, and R. Fischer. 1998. Intracellular expression of a TMV-specific single chain Fv fragment leads to improved virus resistance in *Nicotiana tabacum*. Molecular Breeding. 4:369-379.

Zasloff, M. 2002. Antimicrobial peptides of multicellular organisms. Nature. 415: 389-395.

The invention claimed is:

1. A polynucleotide comprising a nucleic acid sequence coding for a fusion protein, the fusion protein comprising
   a) an anti-fungal protein or peptide (AFP) and an antibody fragment, specifically recognising an epitope of an *Ascomyceta*, and
   b) a cellular targeting signal,
wherein the antibody fragment is a scFv encoded by Seq. ID. No. 1.

2. The polynucleotide of claim 1, further comprising a regulatory sequence for expression in a plant, plant organ, plant tissue, or plant cell.

3. A vector comprising the polynucleotide of claim 1.

4. An expression cassette comprising the polynucleotide of claim 1.

5. The polynucleotide according to claim 2, wherein the regulatory sequence is selected from the group consisting of constitutive, chimeric, tissue specific, inducible synthetic, and cryptic promoters.

6. The polynucleotide according to claim 1, wherein the AFP, and the antibody fragment are arranged in any order relative to each other.

7. A composition comprising a purified preparation of a polynucleotide comprising a nucleic acid sequence coding for a fusion protein, the fusion protein comprising a) an anti-fungal protein or peptide (AFP) and an antibody fragment, specifically recognising an epitope of an *Ascomyceta*, and b) a cellular targeting signal wherein the antibody fragment is a scFv encoded by Seq. ID. No. 1.

8. A method for the production of Ascomyceta-resistant transgenic plants, plant cells, or plant tissues, the method comprising the introduction of a fusion protein into a genome of a plant, plant cell, or plant tissue, the fusion protein comprising a) an anti-fungal protein or peptide (AFP) and an antibody fragment, specifically recognising an epitope of an *Ascomyceta*, and b) a cellular targeting signal wherein the antibody fragment is a scFv encoded by Seq. ID. No. 1.

9. A kit comprising a fusion protein, a polynucleotide coding for the fusion protein, or a combination thereof, with the fusion protein comprising a) an anti-fungal protein or peptide (AFP) and an antibody fragment, specifically recognising an epitope of an *Ascomyceta*, and b) a cellular targeting signal wherein the antibody fragment is a scFv encoded by Seq. ID. No. 1.

10. The kit according to claim 9, wherein the antibody fragment comprises an enzyme for ELISA or immunoblot detection.

11. The kit according to claim 10, wherein the enzyme is an alkaline phosphatase or a horse radish peroxidase.

12. A polynucleotide comprising a nucleic acid sequence coding for a fusion protein, the fusion protein comprising a) an anti-fungal protein or peptide (AFP) and an antibody fragment, specifically recognising an epitope of an *Ascomyceta*, and b) a cellular targeting signal, wherein the AFP is encoded by Seq. ID. No. 12.

13. The polynucleotide of claim 12, further comprising a regulatory sequence for expression in a plant, plant organ, plant tissue, or plant cell.

14. The polynucleotide according to claim 13, wherein the regulatory sequence is selected from the group consisting of constitutive, chimeric, tissue specific, inducible synthetic, and cryptic promoters.

15. A vector comprising the polynucleotide of claim 12.

16. An expression cassette comprising the polynucleotide of claim 12.

17. The polynucleotide of claim 12, wherein a scFv encoding sequence is linked to an AFP encoding sequence via Seq. ID. No. 19, and
the scFv encoding sequence has the 5' position with the AFP encoding portion in the 3' position, or
the AFP encoding portion has the 5' position and the and scFv encoding sequence has the 3' position.

18. The polynucleotide according to claim 12, wherein the AFP, and the antibody fragment are arranged in any order relative to each other.

19. A composition comprising a purified preparation of a polynucleotide comprising a nucleic acid sequence coding for a fusion protein, the fusion protein comprising
  a) an anti-fungal protein or peptide (AFP) and an antibody fragment, specifically recognising an epitope of an *Ascomyceta*, and
  b) a cellular targeting signal
wherein the AFP is encoded by Seq. ID. No. 12.

20. A method for the production of *Ascomyceta*-resistant transgenic plants, plant cells, or plant tissues, the method comprising the introduction of a fusion protein into a genome of a plant, plant cell, or plant tissue, the fusion protein comprising
  a) an anti-fungal protein or peptide (AFP) and an antibody fragment, specifically recognising an epitope of an *Ascomyceta*, and
  b) a cellular targeting signal
wherein the AFP is encoded by Seq. ID. No. 12.

21. A kit comprising a fusion protein, a polynucleotide coding for the fusion protein, or a combination thereof, with the fusion protein comprising
  a) an anti-fungal protein or peptide (AFP) and an antibody fragment, specifically recognising an epitope of an *Ascomyceta*, and
  b) a cellular targeting signal
wherein the AFP is encoded by Seq. ID. No. 12.

22. The kit according to claim 21, wherein the antibody fragment comprises an enzyme for ELISA or immunoblot detection.

23. The kit according to claim 22, wherein the enzyme is an alkaline phosphatase or a horse radish peroxidase.

\* \* \* \* \*

SEQUENCE LISTING

```
<160> NUMBER OF SEQ ID NOS: 72

<210> SEQ ID NO 1
<211> LENGTH: 774
<212> TYPE: DNA
<213> ORGANISM: Artificial Sequence
<220> FEATURE:
<223> OTHER INFORMATION: Description of Artificial Sequence: scFv CWPD2
      with specificity against Fusarium ssp.; originates
      from Gallus gallus.

<400> SEQUENCE: 1
atggctgccg tgacgttgga cgagtccggg ggcggcctcc agacgcccgg aggagggctc      60
agcctcgtct gcaagggctc cgggtttgac ttcagcagtg acaccatgat gtgggtgcgc     120
caggcgcccg gcaagggggtt ggaattcgtc gctggtatta gtggtgatgg tagtgacaca     180
```

-continued

```
aactacgggt cggcggtgaa gggccgtgcc accatctcga gggacaacgg gcagagcaca    240
gtgaggctgc agctgaacaa cctcagggct gaggacaccg ccacctacta ctgcaccaga    300
ggtccttgta gtcctacgaa gaattgtgct gctgatcgta tcgacgcatg gggccacggg    360
accgaggtca ccgtctcctc aggctccacc tcaggctccg gtaaacctgg cccaggggag    420
ggatcaacta agggcgcgcc tgcgctgact cagccgtcct cggtgtcagc aaacctggga    480
ggaaccgtcg agatcacctg ctccgggggt ggctataggt atggctggtt ccagcagaag    540
tctcctggca gtgcccctgt cacagtgatc tactgggatg atgacagcgc caacagaccc    600
tcgaacatcc cttcacgatt ctccggttcc acatctggct ccacagccac attaaccatc    660
actggggtcc aagccgacga cgaggctgtc tatttctgtg ggagctatga caggagtagt    720
ggttatgttt ctatatttgg ggccgggaca accctgaccg tcctaggcca gccc          774
```

```
<210> SEQ ID NO 2
<211> LENGTH: 750
<212> TYPE: DNA
<213> ORGANISM: Artificial Sequence
<220> FEATURE:
<223> OTHER INFORMATION: Description of Artificial Sequence: scFv SGB3
      with specificity against Fusarium ssp.; originates from
      Gallus gallus.

<400> SEQUENCE: 2
atggctgccg tgacgttgga cgagtccggg ggcggcctcc agacgcccgg aggagcgctc     60
agcctcgtct gcaaggcctc cgggttcacc ttcagcagta atggcatggc ctgggtgcga    120
caggcgcctg gcaaggggct ggagtgggtc gcgggtattg atgatggtgg tagtttcaca    180
ggatatgggg cggcggtgaa gggccgtgcc accatctcga gggacaacgg gcagagcaca    240
gtgaggctgc agctgaacaa cctcagggct gaggacaccg ccacctacta ttgcgccaga    300
ggtactggtg gttttggtgg tgatcgtatc gacgcatggg gccacgggac cgaggtcacc    360
gtctcctcag gctccacctc aggctccggt aaacctggcc caggggaggg atcaactaag    420
ggcgcgcctg cgctgactca gccgtcctcg gtgtcagcga acctgggagg aaccgtcaag    480
atcacctgct ccgggagtac tgctcactat agctggcacc agcagaagtc tcctggcagt    540
gcccctgtca ctctgatctc tttcaacaac cagagaccct cggacatccc ttcacgattc    600
tccggttcca aatccggctc cacgggcaca ttaaccatca ctggggtccg agccgaggac    660
gaggctgtct attactgtgg tggctgggac aggagcatta ctgctggttt atttggggcc    720
gggacaaccc tgaccgtcct aggccaaccc                                     750
```

```
<210> SEQ ID NO 3
<211> LENGTH: 756
<212> TYPE: DNA
<213> ORGANISM: Artificial Sequence
<220> FEATURE:
<223> OTHER INFORMATION: Description of Artificial Sequence: scFv
      FPCWPA5 with specificity against Fusarium ssp.; originates
      from Gallus gallus.

<400> SEQUENCE: 3
atggctgccg tgacgttgga cgagtccggg ggcggcctcc agacgcccgg aagagcgctc     60
agcctcgtct gcaaggcctc cgggttcacc ttcagcagtt atgccatggt gtgggtgcga    120
caggcgcccg gcaaagggat ggagtgggtc gctggtattg gcaaggatgg tggtggcaca    180
aactacgggt cggcggtgaa gggccgtgcc accatctcga gggacaacgg gcagagcaca    240
gtgaggctgc agctgaacaa cctcagggct gaggacaccg gcacctacta ctgcggcaaa    300
```

```
actagttgta ctacctcatc ttggtgtgct agtcacatcg acgcatgggg ccacgggacc    360
gaggtcaccg tctcctcagg ctccacctca ggctccggta aacctggccc aggggaggga    420
tcaactaagg gcgcgcctgc gctgactcag ccgtcctcgg tgtcagcaaa cccaggagaa    480
accgtcaagg tcacctgttc cgggggtagt ggcagctatg ctggtatca gcagaagtca     540 cctggcagtg cccctgtcac tctgatctat agcaacgaca gagaccctc gaacatccct     600 tcacgattct ccggttccaa atccggctct gcaaacacat taaccatcac tggggtccaa    660
gtcgaggacg aggctgtcta ttactgtggg agtgcagaca gtaacactaa tgctatattt    720
ggggccggga caaccctgac cgtcctaggc cagccc                              756

<210> SEQ ID NO 4
<211> LENGTH: 789
<212> TYPE: DNA
<213> ORGANISM: Artificial Sequence
<220> FEATURE:
<223> OTHER INFORMATION: Description of Artificial Sequence: scFv SPIII7
      with specificity against Fusarium ssp.; originates
      from Mus musculus.

<400> SEQUENCE: 4
atggccgagg tgcagctggt tgagtctggt ggaggcttgg tgaggcctgg aaattctctg     60
aaactctcct gtgttaccte gggattcact ttcagtaact accggatgca ctggcttcgc    120
cagcctccag ggaagaggct ggagtggatt gctgtaatta agtcaaatc tgaaaatttt     180 ggtgcagatt atgcagagtc tgtgaaaggc agattcacta tttcaagaga tgattcagaa    240
agaagtgtct acctgcagat gaacagatta agagaagaag acactgccac ttattattgt    300 agtagggta gctccgaggg gtttccttac tggggccaag gaccctggt caccgtctcc      360 tcaggctcca cctcaggctc cggtaaacct ggcccagggg agggatcaac taagggcgcg    420
cctgatattc agatgactca gtctccatct tccctgagtg tgtcagcagg agaagaagtc    480
actctgagct gcaagtccag tcagagtctg ttaaacagtg aaatcaaaa gaacttcttg     540 gcctggtatc agcagaaacc agggcagcct cctaaactgt tgatctacgg ggcatccact    600
agggaatctg ggtccctgc tcgcttcaca ggcagtggat ctggaaccga tttcactctt     660
accatcagca gtgtgcaggc tgaagaccag gcagtttatt actgtcagaa tgatcatagt    720
tatccattca cgttcggctc ggggacaaag ttggaaataa acgggctga tgctgcacca    780 actgtatcc                                                            789

<210> SEQ ID NO 5
<211> LENGTH: 753
<212> TYPE: DNA
<213> ORGANISM: Artificial Sequence
<220> FEATURE:
<223> OTHER INFORMATION: Description of Artificial Sequence: scFv VD2
      with specificity against Verticillium dahliae;
      originates from Mus musculus.

<400> SEQUENCE: 5
atggcccaga tccagttggt gcagtctgga cctgagctga agaagcctgg agagacagtc    60
aagatctcct gcaaggtttc tggagataac ttcacaaact atggaatgca atgggtgaag    120
caggctccag gaaagggttt aaagtggatg ggctggataa acacctacac tggagaggca    180
acatatgctg atgactccaa gggacggttt gccttctctt tggaaacctc tgccagcact    240
gcctatttgc agatcaacaa cctcaaaaat gaggacacgg ctacatattt ctgtgcaaga    300
```

```
tttttgggta acccgtacta tgttatggac tactggggtc aaggaacctc agtcactgtc    360
tctgcaggtg gcggcggtag cggcggtggc ggttctggag gcggcgattc tgatgttttg    420
atgacccaga ctccactctc cctgcctgtc agtcttggag atcaagcctc catctcttgc    480
agatctagtc agaacattgt acatagtaat ggaaacacct atttgcaatg gtacctgcag    540
aaaccaggcc agtctccaaa gctcctgatc tacaaagctt ccaaccgatt ttctggggtc    600
ccagccaggt tcagtggcag tggatcaggg acagatttca cactcaagat cagcagagtg    660
gaggctgagg atctgggagt ttattattgc tttcaaggtt cacatgttcc gtacacgttc    720 ggaggggggga ccaagttgga aataaaacgt gct                                753
```

<210> SEQ ID NO 6
<211> LENGTH: 777
<212> TYPE: DNA
<213> ORGANISM: Artificial Sequence
<220> FEATURE:
<223> OTHER INFORMATION: Description of Artificial Sequence: scFv VDcw
      with specificity against Vertcillium dahliae;
      originates from Mus musculus.

<400> SEQUENCE: 6

```
atggccgagg tgaagcttct cgagtctgga cctgagctga agaagcctgg agagacggtc     60
aagatctcct gcaaggcttc tgggtatacc ttcacaaagt atggaatgaa ctgggtgaag    120
caggctccag gaaagggttt aaagtggatg ggctggataa atacctacac tggagagcca    180
acatatgctg atgacttcaa gggacggttt gccttctctt tggaaaccct taccagcact    240 gccttttttgc agatcaacaa cctcaaaaat gaggacacgg ctacatattt ctgtgcaaga    300
tactacggta atccttacta cactatggac tattggggtc aaggaacttc actcaccgtc    360
tcctcaggtg gcggcggtag cggcggtggc ggttctggag gcggcggttc tgacattgtg    420
ctgtcacagt ctccatcctc cctagctgtg tcagttggag agaaggttac tatgagctgc    480
aagtccagtc agagcctttt atatagtagc aatcaaaaga actacttggc ctggtaccag    540
cagaaaccag gcagtctcc taaactgctg atttactggg catccactag gaatctgggg    600
gtccctgatc gcttcacagg cagtggatct gggacagatt tcaccctcac catcagcagt    660
gtgaaggctg aagacctggc agtttattac tgtcaacaat attatagcta tccattcacg    720
ttcggctcgg ggacaaagtt ggaaataaaa cgggctgatg ctgcaccaac tgtatcc       777
```

<210> SEQ ID NO 7
<211> LENGTH: 744
<212> TYPE: DNA
<213> ORGANISM: Artificial Sequence
<220> FEATURE:
<223> OTHER INFORMATION: Description of Artificial Sequence: scFv VDM1
      with specificity against Verticillium dahliae;
      originates from Mus musculus.

<400> SEQUENCE: 7

```
atggcccagg tgcagctgaa gcagtcagga gctgaggtgg tgaaacctgg ggcttcagtg     60
aagatatcct gcaaggcctc tggctacagg ttcactgacc atgctattca ctgggtgaag    120
cagaagcctg aacagggcct ggaatggatt ggatatattt ctcccggaaa tggtgatatt    180
aagtacaatg agaagttcag gggcaaggcc acactgactg cagacaaatc ctctagcact    240
gcctacatgc agctcaacag cctgacatct gaggattctg cagtgtatct ctgtaaaaga    300
tggcctggag cggggatgga ctactgggt caaggaacct cagtcaccgt ctctgcaggt    360
ggcggcggta gcggcggtgg cggttctgga ggcggcggtt ctgatattgt gatgacccaa    420
```

```
aatgagctct cctatcctgt cacttctgga gaatcagttt ccatctcctg caggtctagt    480
aagagtctcc tatataagga tgggaagaca tacttgaatt ggtttctgca gagaccagga    540
caatctcctc agctcctgat ctatttgatg tccacccgtg catcaggagt ctcagaccgg    600
tttagtggca gtgggtcagg aacagatttc accctggaaa tcagtagagt gaaggctgag    660
gatgtgggtg tgtattactg tcaacaactt gtagagtatc cgctcacgtt cggtgctggg    720
accaagttgg agctgaaacg ggct                                          744
```

<210> SEQ ID NO 8
<211> LENGTH: 777
<212> TYPE: DNA
<213> ORGANISM: Artificial Sequence
<220> FEATURE:
<223> OTHER INFORMATION: Description of Artificial Sequence: scFv VDM2
      with specificity against Verticillium dahliae;
      originates from Mus musculus.

<400> SEQUENCE: 8

```
atggccgagg tgaagcttct cgagtttgga cctgagctga agaagcctgg agagacggtc    60
aagatctcct gcaaggcttc tgggtatacc ttcacaaagt atggaatgaa ctgggtgaag   120
caggctccag gaaagggttt aaagtggatg ggctggataa ataccacac tggagagcca   180 acatatgctg atgacttcaa gggacggttt gccttctctt tggaaacctc taccagcact   240 gccttttgc agatcaacaa cctcaaaaat gaggacacgg ctacatattt ctgtgcaaga   300
tactacggta atccttacta cactatggac tattggggtc aaggaacttc actcaccgtc   360
tcctcaggtg gcggcggtag cggcggtggc ggttctggag gcggcggttc tgacattgtg   420
ctgtcacagt ctccatcctc cctagctgtg ttagttggag agaaggttac tatgagctgc   480
aagttcagtc agagcctttt atatagtagc aatcaaaaga actacttggc ctggtaccag   540
cagaaaccag ggcagtctcc taaactgcta atttactggg catccactag gaatctgggg   600
gtccctgatc gcttcacagg cagtggatct ggaacagatt tcaccctcac catcagcagt   660
gtgaaggctg aagacctggc agtttattac tgtcaacaat attatagcta tccattcacg   720
ttcggctcgg gaacaaagtt ggaaataaaa cgggctgatg ctgcaccaac tgtatcc     777
```

<210> SEQ ID NO 9
<211> LENGTH: 777
<212> TYPE: DNA
<213> ORGANISM: Artificial Sequence
<220> FEATURE:
<223> OTHER INFORMATION: Description of Artificial Sequence: scFv PL2
      with specificity against Phoma lingam; originates from
      Mus musculus.

<400> SEQUENCE: 9

```
atggccgatg tacagcttca ggagtcggga cctggcctcg tgaaaccttc tcagtctctg    60
tctctcacct gctctgtcac tggctactcc atcaccagtg gttattactg gaactggatc   120
cggcagtttc caggaaacaa actggaatgg atgggctaca taagctacga cggtaccaat   180
aacaacaacc catctctcaa aaatcgaatc tccatcactc gtgacgcatc taagaaccag   240 ttttcctga agttgaattc tgtgactact gaggacacag ctacatatca ctgtgcaaga   300 ggggcccct actatggtaa ggggacctgg tttccttact ggggccaagg accctggtc   360 accgtctcct caggctccac ctcaggctcc ggtaaacctg cccagggga gggatcaact   420 aagggcgcgc ctgaaattgt gctgacccag tctccatcct ccctggctat gtcagtagga   480
```

-continued

```
cagaaggtca ctatgagctg caagtccagt cagagccttt taaatagtag caatcaaaag    540
aactatttgg cctggtacca gcagaaacca ggacagtctc ctaaacttct ggtatatttt    600
gcatccacta gggaatctgg ggtccctgat cgcttcatag gcagtggatc tgggacagat    660
ttcactctca ccatcagcag tgtgcaggct gaagacctgg cagattactt ctgtcagcaa    720
cattatagca ctcctccgac gttcggtgga ggcaccaaac tggagatcaa acgggct       777
```

<210> SEQ ID NO 10
<211> LENGTH: 783
<212> TYPE: DNA
<213> ORGANISM: Artificial Sequence
<220> FEATURE:
<223> OTHER INFORMATION: Description of Artificial Sequence: scFv PLp9 with specificity against Phoma lingam; originates from Mus musculus.

<400> SEQUENCE: 10

```
atggctgccg tgacgttgga cgagtccggg ggcggcctcc agacgcccgg aggagcgctc     60
agcctcgtct gcaaggcctc cgggttcgac ttcaaggggt acgagatggc ctgggtgcga    120
caggcgcccg gcaaggggct ggaatgggtc gctgctatta gcagtggtta taacacaaac    180
tacggggcgg cggtgaaggg ccgtgccacc atctcgagga acaacgggca gagcacagtg    240
aggctgcagc tgaacaacct cagggctgag gacaccgcca cctactactg cgccaaaact    300
catggtgatt atggctgtgc tggtaatgct tggtgttctg ctggtaatat cgacgcatgg    360
ggccacggga ccgaggtcac cgtctcctca ggctccacct caggctccgg taaacctggc    420
ccaggggagg gatcaactaa gggcgcgcct gggctgactc aggcgtcctc ggtgtcagca    480
aacccgggag aaaccgtcaa gatcacctgc tccgggggtg gcagctatgc tggaagttac    540
tattatggct ggtaccagca gaagacacct ggcagtgccc ctgtcactgt gatctatagc    600
aacgacaaga gaccctcgaa catcccttca cgattctccg gttccctatc cggctcaaca    660
aacacattaa ccatcactgg ggtccaagtc gacgacgagg ctgtctattt ctgtggtgcc    720
tacgacaaca attatgctgg tatatttggg gccgggacaa ccctgaccgt cctaggccag    780
ccc                                                                  783
```

<210> SEQ ID NO 11
<211> LENGTH: 744
<212> TYPE: DNA
<213> ORGANISM: Artificial Sequence
<220> FEATURE:
<223> OTHER INFORMATION: Description of Artificial Sequence: scFv SS2 with specificity against Sclerotinia sclerotiorum; originates from Mus musculus.

<400> SEQUENCE: 11

```
atggcccagg tacagctgca gcagtctggg actgtgctgg caaggcctgg ggcttcagtg     60
aagatgtcct gcaaggcttc tggctacacc tttaccagct actggatgca ctgggtaaaa    120
cagaggcctg gacagggtct ggaatggatt ggcgctattt atcctggaaa tagtgatact    180
agctacaacc agaagttcaa gggcaaggcc aaactgactg cagtcacatc caccagcact    240
gcctacatgg agctcagcag cctgacaaat gaggactctg cggtctatta ctgtacaaga    300
actgactggg actatgctat ggactactgg ggtcaaggaa cctcggtcac cgtctcctca    360
ggctccacct caggctccgg taaacctggc ccaggggagg gatcaactaa gggcgcgcct    420
gacattgttc tcttccagtc tccagtaatc atgtctgctt ctccaggaga gaaggtcacc    480
atgacctgca gtgccagctc aagtgtaaat tacatttact ggtaccagtg gaagtcaggc    540
```

```
acctccccca aaagatggat ctttgacaca tccaaactgg cttctggagt ccctgttcgc      600
ttcagtggca gtgggtctgg gacctctttc tctctcacaa tcagcagcat ggaggctgaa      660
gatattgcca cttattactg ccagcagtgg agtagtcccc cactcacgtt cggtgctggg      720
accaaattgg aactgaaacg ggct                                             744

<210> SEQ ID NO 12
<211> LENGTH: 903
<212> TYPE: DNA
<213> ORGANISM: Wheat

<400> SEQUENCE: 12
atggagcagt gcggctcgca ggccggcggg gcgacgtgcc ccaactgcct ctgctgcagc       60
aagttcggct tctgcggctc cacctccgac tactgcggca acggctgcca gagccagtgc      120
aacggctgca gcggcggcgg caccccggta ccggtaccga cccccaccgg cggcggcgtg      180
tcctccatta tctcgcagtc gctcttcgac cagatgctgc tgcaccgcaa cgatgcggcg      240
tgccaggcca aggggttcta caactacggc gcctttgtag ccgccgccaa ctcgttctcg      300
ggcttcgcga ccacgggtgg cgccgacgtc aggaagcgcg aggtggccgc gttcctcgct      360
cagacctccc acgagaccac cggcgggtgg ccaacggcgc ccgacggccc ctactcgtgg      420
ggctactgct tcaaccagga gcgggcgcc gcctccgact actgctcgcc gaactcacag      480
tggccgtgcg cgccgggcaa gaagtacttc gggcgcgggc ccatccagat ctcatacaac      540
tacaactacg gccggctgg gcgggccatc ggaccgacc tgctcaacaa cccggacctc      600
gtggcgacgg atgcgaccgt gtcgtttaag acggcgctgt ggttctggat gacgccgcag      660
tcacctaaac cttcgagcca cgacgtgatt acgggccggt ggagccctc gggcgccgac      720 caggcggcgg ggagggtgcc tgggtacggt gtgatcacta acatcatcaa cggtgggctc      780
gagtgcgggc gcgggcagga cggccgtgtt gccgaccgga tcgggttcta caagcgctac      840
tgcgacctac tcggcgtcag ctacggcgac aacctggact gctacaacca gaggccgttc      900
gcc                                                                    903

<210> SEQ ID NO 13
<211> LENGTH: 159
<212> TYPE: DNA
<213> ORGANISM: Raphanus sativus

<400> SEQUENCE: 13
atggctcaga agttgtgtca gaggccaagt gggacatggt caggagtctg tggaaataat       60
aacgcgtgca agaatcagtg cattcgactt gagaaagcac gacatgggtc ttgcaactat      120
gtcttcccag ctcacaagtg tatctgttat ttcccttgt                             159

<210> SEQ ID NO 14
<211> LENGTH: 156
<212> TYPE: DNA
<213> ORGANISM: Homo sapiens

<400> SEQUENCE: 14
atgggccgta ggagaaggag tgttcagtgg tgcgccgtat cccaacccga ggccacaaaa       60
tgcttccaat ggcaaaggaa tatgagaaaa gtgcgtggcc ctcctgtcag ctgcataaag      120
agagactccc ccatccagtg tatccaggcc attgcg                                156

<210> SEQ ID NO 15
```

```
<211> LENGTH: 156
<212> TYPE: DNA
<213> ORGANISM: Aspergillus giganteus

<400> SEQUENCE: 15
atggccacct acaacggcaa gtgctacaag aaggacaaca tctgcaagta caaggcccag      60
agcggcaaga ccgctatctg caagtgctac gtcaagaagt gcccaaggga cggagccaag     120
tgcgagttcg acagctacaa gggcaagtgc tactgc                               156

<210> SEQ ID NO 16
<211> LENGTH: 105
<212> TYPE: DNA
<213> ORGANISM: Zea mays

<400> SEQUENCE: 16
atgggcagga gcggcagggg agagtgcagg aggcaatgcc tcaggaggca cgaaggccag      60
ccttgggaga cccaggagtg catgaggagg tgcaggagga ggga                      105

<210> SEQ ID NO 17
<211> LENGTH: 285
<212> TYPE: DNA
<213> ORGANISM: Allium cepa

<400> SEQUENCE: 17
atggcacaga acatatgccc aagggttaat cgaattgtga caccctgtgt ggcctacgga      60
ctcggaaggg caccaatcgc cccatgctgc agagccctga cgatctacg gtttgtgaat     120 actagaaacc tacgacgtgc tgcatgccgc tgcctcgtag gggtagtgaa ccggaacccc     180
ggtctgagac gaaaccctag atttcagaac attcctcgtg attgtcgcaa cacctttgtt     240
cgtcccttct ggtggcgtcc aagaattcaa tgcggcagga ttaac                    285

<210> SEQ ID NO 18
<211> LENGTH: 69
<212> TYPE: DNA
<213> ORGANISM: Artificial Sequence
<220> FEATURE:
<223> OTHER INFORMATION: Description of Artificial Sequence: leader
      peptide (targets apoplast) derived from the heavy chain of
      a Mus musculus antibody; codons are optimized.

<400> SEQUENCE: 18
atggactttc aagtgcagat tttcagcttc ctcctcatca gcgcctcagt tatcatctct      60
aggggatcc                                                             69

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: (G4S)2
      linker

<400> SEQUENCE: 19
ggtggaggcg gatctggtgg cggtggaagc                                      30

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: cmyc tag
```

-continued

<400> SEQUENCE: 20
gaacaaaaac tcatctcaga agaggatctg ggtgcactcg ac  42

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: His6 tag

<400> SEQUENCE: 21
catcaccatc accatcac  18

<210> SEQ ID NO 22
<211> LENGTH: 1878
<212> TYPE: DNA
<213> ORGANISM: Artificial Sequence
<220> FEATURE:
<223> OTHER INFORMATION: Description of Artificial Sequence: fusion
      protein comprising the leader peptide - chitinase - linker
      - scFv CWPD2 - cmyc/His6.

<400> SEQUENCE: 22

| | | |
|---|---|---|
| atggactttc aagtgcagat tttcagcttc ctcctcatca gcgcctcagt tatcatctct | 60 |
| aggggatcca tggagcagtg cggctcgcag gccggcgggg cgacgtgccc caactgcctc | 120 |
| tgctgcagca agttcggctt ctgcggctcc acctccgact actgcggcaa cggctgccag | 180 |
| agccagtgca acggctgcag cggcggcggc accccggtac cggtaccgac ccccaccggc | 240 |
| ggcggcgtgt cctccattat ctcgcagtcg ctcttcgacc agatgctgct gcaccgcaac | 300 |
| gatgcggcgt gccaggccaa ggggttctac aactacggcg cctttgtagc cgccgccaac | 360 |
| tcgttctcgg gcttcgcgac cacgggtggc gccgacgtca ggaagcgcga ggtggccgcg | 420 |
| ttcctcgctc agacctccca cgagaccacc ggcgggtggc aacggcgcc cgacggcccc | 480 |
| tactcgtggg gctactgctt caaccaggag cgcggcgccg cctccgacta ctgctcgccg | 540 |
| aactcacagt ggccgtgcgc gccgggcaag aagtacttcg gcgcgggcc catccagatc | 600 |
| tcatacaact acaactacgg gccggctggg cgggccatcg ggaccgacct gctcaacaac | 660 |
| ccggacctcg tggcgacgga tgcgaccgtg tcgtttaaga cggcgctgtg gttctggatg | 720 |
| acgccgcagt cacctaaacc ttcgagccac gacgtgatta cgggccggtg gagcccctcg | 780 |
| ggcgccgacc aggcggcggg gagggtgcct gggtacggtg tgatcactaa catcatcaac | 840 |
| ggtgggctcg agtgcgggcg cgggcaggac ggccgtgttg ccgaccggat cgggttctac | 900 |
| aagcgctact gcgacctact cggcgtcagc tacggcgaca acctggactg ctacaaccag | 960 |
| aggccgttcg ccgtcgacgg tggaggcgga tctggtggcg gtggaagcgc ggcccagccg | 1020 |
| gccatggctg ccgtgacgtt ggacgagtcc ggggcggcc tccagacgcc cggaggaggg | 1080 |
| ctcagcctcg tctgcaaggg ctccgggttt gacttcagca gtgacaccat gatgtgggtg | 1140 |
| cgccaggcgc ccggcaaggg gttggaattc gtcgctggta ttagtggtga tggtagtgac | 1200 |
| acaaactacg gtcggcggt gaaggggccgt gccaccatct cgaggacaa cgggcagagc | 1260 |
| acagtgaggc tgcagctgaa caacctcagg gctgaggaca ccgccaccta ctactgcacc | 1320 |
| agaggtcctt gtagtcctac gaagaattgt gctgctgatc gtatcgacgc atggggccac | 1380 |
| gggaccgagg tcaccgtctc ctcaggctcc acctcaggct ccggtaaacc tggcccaggg | 1440 |
| gagggatcaa ctaagggcgc gcctgcgctg actcagccgt cctcggtgtc agcaaacctg | 1500 |
| ggaggaaccg tcgagatcac ctgctccggg ggtggctata ggtatggctg gttccagcag | 1560 |

```
aagtctcctg gcagtgcccc tgtcacagtg atctactggg atgatgacag cgccaacaga    1620
ccctcgaaca tcccttcacg attctccggt tccacatctg gctccacagc cacattaacc    1680
atcactgggg tccaagccga cgacgaggct gtctatttct gtgggagcta tgacaggagt    1740
agtggttatg tttctatatt tggggccggg acaaccctga ccgtcctagg ccagcccgtc    1800
gaggcggccg cagaacaaaa actcatctca gaagaggatc tgggtgcact cgaccatcac    1860
catcaccatc acgtctag                                                  1878

<210> SEQ ID NO 23
<211> LENGTH: 1857
<212> TYPE: DNA
<213> ORGANISM: Artificial Sequence
<220> FEATURE:
<223> OTHER INFORMATION: Description of Artificial Sequence: fusion
      protein comprising the leader peptide - chitinase - linker
      - scFv VD2 - cmyc/His6

<400> SEQUENCE: 23
atggactttc aagtgcagat tttcagcttc ctcctcatca gcgcctcagt tatcatctct      60
aggggatcca tggagcagtg cggctcgcag gccggcgggg cgacgtgccc caactgcctc    120
tgctgcagca agttcggctt ctgcggctcc acctccgact actgcggcaa cggctgccag    180
agccagtgca acggctgcag cggcggcggc accccggtac cggtaccgac ccccaccggc    240
ggcggcgtgt cctccattat ctcgcagtcg ctcttcgacc agatgctgct gcaccgcaac    300
gatgcggcgt gccaggccaa ggggttctac aactacggcg cctttgtagc cgccgccaac    360
tcgttctcgg gcttcgcgac cacgggtggc gccgacgtca ggaagcgcga ggtggccgcg    420
ttcctcgctc agacctccca cgagaccacc ggcgggtggc aacggcgcc cgacggcccc    480 tactcgtggg gctactgctt caaccaggag cgcggcgccg cctccgacta ctgctcgccg    540
aactcacagt ggccgtgcgc gccgggcaag aagtacttcg ggcgcgggcc catccagatc    600
tcatacaact acaactacgg gccggctggg cgggccatcg ggaccgacct gctcaacaac    660
ccggacctcg tggcgacgga tgcgaccgtg tcgtttaaga cggcgctgtg gttctggatg    720
acgccgcagt cacctaaacc ttcgagccac gacgtgatta cgggccggtg gagcccctcg    780
ggcgccgacc aggcggcggg gagggtgcct ggtacggtg tgatcactaa catcatcaac    840
ggtgggctcg agtgcgggcg cgggcaggac ggccgtgttg ccgaccggat cgggttctac    900
aagcgctact gcgacctact cggcgtcagc tacggcgaca acctggactg ctacaaccag    960
aggccgttcg ccgtcgacgg tggaggcgga tctggtggcg gtggaagcgc ggcccagccg   1020
gccatggccc agatccagtt ggtgcagtct ggacctgagc tgaagaagcc tggagagaca   1080
gtcaagatct cctgcaaggt ttctggagat aacttcacaa actatggaat gcaatgggtg   1140
aagcaggctc caggaaaggg tttaaagtgg atggctgga taaacaccta cactggagag   1200
gcaacatatg ctgatgactc aagggacggg tttgccttct ctttggaaac ctctgccagc   1260
actgcctatt gcagatcaa caacctcaaa aatgaggaca cggctacata tttctgtgca   1320 agattttttgg gtaacccgta ctatgttatg gactactggg gtcaaggaac ctcagtcact   1380
gtctctgcag gtggcggcgg tagcggcggt ggcggttctg gaggcggcga ttctgatgtt   1440
ttgatgaccc agactccact ctccctgcct gtcagtcttg gagatcaagc ctccatctct   1500
tgcagatcta gtcagaacat tgtacatagt aatggaaaca cctatttgca atggtacctg   1560
cagaaaccag gccagtctcc aaagctcctg atctacaaag cttccaaccg attttctggg   1620
```

```
gtcccagcca ggttcagtgg cagtggatca gggacagatt tcacactcaa gatcagcaga    1680
gtggaggctg aggatctggg agtttattat tgctttcaag gttcacatgt tccgtacacg    1740
ttcggagggg ggaccaagtt ggaaataaaa cgtgctgtcg aggcggccgc agaacaaaaa    1800
ctcatctcag aagaggatct gggtgcactc gaccatcacc atcaccatca cgtctag      1857
```

<210> SEQ ID NO 24
<211> LENGTH: 1881
<212> TYPE: DNA
<213> ORGANISM: Artificial Sequence
<220> FEATURE:
<223> OTHER INFORMATION: Description of Artificial Sequence: fusion
protein comprising leader peptide - chitinase - linker -
scFv PL2 - cmyc/His6.

<400> SEQUENCE: 24

```
atggactttc aagtgcagat tttcagcttc ctcctcatca gcgcctcagt tatcatctct      60
aggggatcca tggagcagtg cggctcgcag gccggcgggg cgacgtgccc caactgcctc     120
tgctgcagca agttcggctt ctgcggctcc acctccgact actgcggcaa cggctgccag     180
agccagtgca acggctgcag cggcggcggc accccggtac cggtaccgac ccccaccggc     240
ggcggcgtgt cctccattat ctcgcagtcg ctcttcgacc agatgctgct gcaccgcaac     300
gatgcggcgt gccaggccaa ggggttctac aactacggcg cctttgtagc cgccgccaac     360
tcgttctcgg gcttcgcgac cacgggtggc gccgacgtca ggaagcgcga ggtggccgcg     420
ttcctcgctc agacctccca cgagaccacc ggcgggtggc caacggcgcc cgacggcccc     480
tactcgtggg gctactgctt caaccaggag gcgcggcgcc gctccgacta ctgctcgccg     540
aactcacagt ggccgtgcgc gccgggcaag aagtacttcg gcgcgggcc atccagatc      600 tcatacaact acaactacgg gccggctggg cgggccatcg gaccgacct gctcaacaac     660 ccggacctcg tggcgacgga tgcgaccgtg tcgtttaaga cggcgctgtg gttctggatg     720
acgccgcagt cacctaaacc ttcgagccac gacgtgatta cgggccggtg gagcccctcg     780
ggcgccgacc aggcggcggg gagggtgcct gggtacggtg tgatcactaa catcatcaac     840
ggtgggctcg agtgcgggcg cgggcaggac ggccgtgttg ccgaccggat cgggttctac     900
aagcgctact gcgacctact cggcgtcagc tacggcgaca acctggactg ctacaaccag     960
aggccgttcg ccgtcgacgg tggaggcgga tctggtggcg gtggaagcgc ggcccagccg    1020
gccatggccg atgtacagct tcaggagtcg ggacctggcc tcgtgaaacc ttctcagtct    1080
ctgtctctca cctgctctgt cactggctac tccatcacca gtggttatta ctggaactgg    1140
atccggcagt ttccaggaaa caaactggaa tggatgggct acataagcta cgacggtacc    1200
aataacaaca cccatctctc caaaaatcga atctccatca ctcgtgacgc atctaagaac    1260
cagtttttcc tgaagttgaa ttctgtgact actgaggaca cagctacata tcactgtgca    1320
agaggggccc cctactatgg taaggggacc tggtttcctt actggggcca agggaccctg    1380
gtcaccgtct cctcaggctc cacctcaggc tccggtaaac ctggcccagg ggagggatca    1440
actaagggcg cgcctgaaat tgtgctgacc cagtctccat cctccctggc tatgtcagta    1500
ggacagaagg tcactatgag ctgcaagtcc agtcagagcc ttttaaatag tagcaatcaa    1560
aagaactatt tggcctggta ccagcagaaa ccaggacagt ctcctaaact tctggtatat    1620
tttgcatcca ctagggaatc tggggtccct gatcgcttca taggcagtgg atctgggaca    1680
gatttcactc tcaccatcag cagtgtgcag gctgaagacc tggcagatta cttctgtcag    1740
caacattata gcactcctcc gacgttcggt ggaggcacca aactggagat caaacgggct    1800
```

```
gtcgaggcgg ccgcagaaca aaaactcatc tcagaagagg atctgggtgc actcgaccat   1860
caccatcacc atcacgtcta g                                             1881

<210> SEQ ID NO 25
<211> LENGTH: 1848
<212> TYPE: DNA
<213> ORGANISM: Artificial Sequence
<220> FEATURE:
<223> OTHER INFORMATION: Description of Artificial Sequence: fusion
      protein comprising the leader peptide - chitinase - linker
      - scFv SS2 - cmyc/His6.

<400> SEQUENCE: 25
atggactttc aagtgcagat tttcagcttc ctcctcatca gcgcctcagt tatcatctct     60
aggggatcca tggagcagtg cggctcgcag gccggcgggg cgacgtgccc caactgcctc    120
tgctgcagca agttcggctt ctgcggctcc acctccgact actgcggcaa cggctgccag    180
agccagtgca acggctgcag cggcggcggc accccggtac cggtaccgac ccccaccggc    240
ggcggcgtgt cctccattat ctcgcagtcg ctcttcgacc agatgctgct gcaccgcaac    300
gatgcggcgt gccaggccaa ggggttctac aactacggcg cctttgtagc cgccgccaac    360
tcgttctcgg gcttcgcgac cacgggtggc gccgacgtca ggaagcgcga ggtggccgcg    420
ttcctcgctc agacctccca cgagaccacc ggcgggtggc aacggcgcc cgacggcccc    480 tactcgtggg gctactgctt caaccaggag cgcggcgccg cctccgacta ctgctcgccg    540
aactcacagt ggccgtgcgc gccgggcaag aagtacttcg gcgcgggcc catccagatc    600 tcatacaact acaactacgg gccggctggg cgggccatcg ggaccgacct gctcaacaac    660
ccggacctcg tggcgacgga tgcgaccgtg tcgtttaaga cggcgctgtg gttctggatg    720
acgccgcagt cacctaaacc ttcgagccac gacgtgatta cgggccggtg gagccctcg    780 ggcgccgacc aggcggcggg gagggtgcct gggtacggtg tgatcactaa catcatcaac    840
ggtgggctcg agtgcgggcg cgggcaggac ggccgtgttg ccgaccggat cgggttctac    900
aagcgctact gcgacctact cggcgtcagc tacgcgaca acctggactg ctacaaccag    960
aggccgttcg ccgtcgacgg tggaggcgga tctggtggcg gtggaagcgc ggcccagccg   1020
gccatggccc aggtacagct gcagcagtct gggactgtgc tggcaaggcc tggggcttca   1080
gtgaagatgt cctgcaaggc ttctggctac acctttacca gctactggat gcactgggta   1140
aaacagaggc ctggacaggg tctggaatgg attggcgcta tttatcctgg aaatagtgat   1200
actagctaca accagaagtt caagggcaag gccaaactga ctgcagtcac atccaccagc   1260
actgcctaca tggagctcag cagcctgaca aatgaggact ctgcggtcta ttactgtaca   1320
agaactgact gggactatgc tatggactac tggggtcaag gaacctcggt caccgtctcc   1380
tcaggctcca cctcaggctc cggtaaacct ggcccagggg agggatcaac taagggcgcg   1440
cctgacattg ttctcttcca gtctccagta atcatgtctg cttctccagg agagaaggtc   1500
accatgacct gcagtgccag ctcaagtgta aattacattt actggtacca gtggaagtca   1560
ggcacctccc ccaaaagatg gatctttgac acatccaaac tggcttctgg agtccctgtt   1620
cgcttcagtg gcagtgggtc tgggacctct ttctctctca caatcagcag catggaggct   1680
gaagatattg ccacttatta ctgccagcag tggagtagtc ccccactcac gttcggtgct   1740
gggaccaaat tggaactgaa acgggctgtc gaggcggccg cagaacaaaa actcatctca   1800
gaagaggatc tgggtgcact cgaccatcac catcaccatc acgtctag                1848
```

<210> SEQ ID NO 26
<211> LENGTH: 258
<212> TYPE: PRT
<213> ORGANISM: Artificial Sequence
<220> FEATURE:
<223> OTHER INFORMATION: Description of Artificial Sequence: scFv CWPD2
    with specificity against Fusarium ssp.; originates
    from Gallus gallus.

<400> SEQUENCE: 26

Met Ala Ala Val Thr Leu Asp Glu Ser Gly Gly Gly Leu Gln Thr Pro
 1               5                  10                  15

Gly Gly Gly Leu Ser Leu Val Cys Lys Gly Ser Gly Phe Asp Phe Ser
             20                  25                  30

Ser Asp Thr Met Met Trp Val Arg Gln Ala Pro Gly Lys Gly Leu Glu
         35                  40                  45

Phe Val Ala Gly Ile Ser Gly Asp Gly Ser Thr Asn Tyr Gly Ser
     50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                 85                  90                  95

Tyr Cys Thr Arg Gly Pro Cys Ser Pro Thr Lys Asn Cys Ala Ala Asp
            100                 105                 110

Arg Ile Asp Ala Trp Gly His Gly Thr Glu Val Thr Val Ser Ser Gly
        115                 120                 125

Ser Thr Ser Gly Ser Gly Lys Pro Gly Pro Gly Glu Gly Ser Thr Lys
    130                 135                 140

Gly Ala Pro Ala Leu Thr Gln Pro Ser Ser Val Ser Ala Asn Leu Gly
145                 150                 155                 160

Gly Thr Val Glu Ile Thr Cys Ser Gly Gly Gly Tyr Arg Tyr Gly Trp
                165                 170                 175

Phe Gln Gln Lys Ser Pro Gly Ser Ala Pro Val Thr Val Ile Tyr Trp
            180                 185                 190

Asp Asp Asp Ser Ala Asn Arg Pro Ser Asn Ile Pro Ser Arg Phe Ser
        195                 200                 205

Gly Ser Thr Ser Gly Ser Thr Ala Thr Leu Thr Ile Thr Gly Val Gln
    210                 215                 220

Ala Asp Asp Glu Ala Val Tyr Phe Cys Gly Ser Tyr Asp Arg Ser Ser
225                 230                 235                 240

Gly Tyr Val Ser Ile Phe Gly Ala Gly Thr Thr Leu Thr Val Leu Gly
                245                 250                 255

Gln Pro

<210> SEQ ID NO 27
<211> LENGTH: 250
<212> TYPE: PRT
<213> ORGANISM: Artificial Sequence
<220> FEATURE:
<223> OTHER INFORMATION: Description of Artificial Sequence: scFv SGB3
    with specificity against Fusarium ssp.; originates from
    Gallus gallus.

<400> SEQUENCE: 27

Met Ala Ala Val Thr Leu Asp Glu Ser Gly Gly Gly Leu Gln Thr Pro
 1               5                  10                  15

Gly Gly Ala Leu Ser Leu Val Cys Lys Ala Ser Gly Phe Thr Phe Ser
             20                  25                  30

-continued

Ser Asn Gly Met Ala Trp Val Arg Gln Ala Pro Gly Lys Gly Leu Glu
             35                  40                  45

Trp Val Ala Gly Ile Asp Asp Gly Gly Ser Phe Thr Gly Tyr Gly Ala
     50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                 85                  90                  95

Tyr Cys Ala Arg Gly Thr Gly Gly Phe Gly Gly Asp Arg Ile Asp Ala
            100                 105                 110

Trp Gly His Gly Thr Glu Val Thr Val Ser Ser Gly Ser Thr Ser Gly
        115                 120                 125

Ser Gly Lys Pro Gly Pro Gly Glu Gly Ser Thr Lys Gly Ala Pro Ala
    130                 135                 140

Leu Thr Gln Pro Ser Ser Val Ser Ala Asn Leu Gly Gly Thr Val Lys
145                 150                 155                 160

Ile Thr Cys Ser Gly Ser Thr Ala His Tyr Ser Trp His Gln Gln Lys
                165                 170                 175

Ser Pro Gly Ser Ala Pro Val Thr Leu Ile Ser Phe Asn Asn Gln Arg
            180                 185                 190

Pro Ser Asp Ile Pro Ser Arg Phe Ser Gly Ser Lys Ser Gly Ser Thr
        195                 200                 205

Gly Thr Leu Thr Ile Thr Gly Val Arg Ala Glu Asp Glu Ala Val Tyr
    210                 215                 220

Tyr Cys Gly Gly Trp Asp Arg Ser Ile Thr Ala Gly Leu Phe Gly Ala
225                 230                 235                 240

Gly Thr Thr Leu Thr Val Leu Gly Gln Pro
                245                 250

<210> SEQ ID NO 28
<211> LENGTH: 252
<212> TYPE: PRT
<213> ORGANISM: Artificial Sequence
<220> FEATURE:
<223> OTHER INFORMATION: Description of Artificial Sequence: scFv
      FPCWPA5 with specificity against Fusarium ssp.; originates
      from Gallus gallus.

<400> SEQUENCE: 28

Met Ala Ala Val Thr Leu Asp Glu Ser Gly Gly Gly Leu Gln Thr Pro
 1               5                  10                  15

Gly Arg Ala Leu Ser Leu Val Cys Lys Ala Ser Gly Phe Thr Phe Ser
            20                  25                  30

Ser Tyr Ala Met Val Trp Val Arg Gln Ala Pro Gly Lys Gly Met Glu
        35                  40                  45

Trp Val Ala Gly Ile Gly Lys Asp Gly Gly Thr Asn Tyr Gly Ser
    50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Gly Thr Tyr
                85                  90                  95

Tyr Cys Gly Lys Thr Ser Cys Thr Thr Ser Ser Trp Cys Ala Ser His
            100                 105                 110

Ile Asp Ala Trp Gly His Gly Thr Glu Val Thr Val Ser Ser Gly Ser
        115                 120                 125

```
Thr Ser Gly Ser Gly Lys Pro Gly Pro Gly Glu Gly Ser Thr Lys Gly
        130                 135                 140

Ala Pro Ala Leu Thr Gln Pro Ser Ser Val Ser Ala Asn Pro Gly Glu
145                 150                 155                 160

Thr Val Lys Val Thr Cys Ser Gly Gly Ser Gly Ser Tyr Gly Trp Tyr
                165                 170                 175

Gln Gln Lys Ser Pro Gly Ser Ala Pro Val Thr Leu Ile Tyr Ser Asn
            180                 185                 190

Asp Lys Arg Pro Ser Asn Ile Pro Ser Arg Phe Ser Gly Ser Lys Ser
        195                 200                 205

Gly Ser Ala Asn Thr Leu Thr Ile Thr Gly Val Gln Val Glu Asp Glu
    210                 215                 220

Ala Val Tyr Tyr Cys Gly Ser Ala Asp Ser Asn Thr Asn Ala Ile Phe
225                 230                 235                 240

Gly Ala Gly Thr Thr Leu Thr Val Leu Gly Gln Pro
                245                 250

<210> SEQ ID NO 29
<211> LENGTH: 263
<212> TYPE: PRT
<213> ORGANISM: Artificial Sequence
<220> FEATURE:
<223> OTHER INFORMATION: Description of Artificial Sequence:  scFv
      SPIII7 with specificity against Fusarium ssp.; originates
      from Mus musculus.

<400> SEQUENCE: 29

Met Ala Glu Val Gln Leu Val Glu Ser Gly Gly Gly Leu Val Arg Pro
  1               5                  10                  15

Gly Asn Ser Leu Lys Leu Ser Cys Val Thr Ser Gly Phe Thr Phe Ser
             20                  25                  30

Asn Tyr Arg Met His Trp Leu Arg Gln Pro Pro Gly Lys Arg Leu Glu
         35                  40                  45

Trp Ile Ala Val Ile Lys Val Lys Ser Glu Asn Phe Gly Ala Asp Tyr
     50                  55                  60

Ala Glu Ser Val Lys Gly Arg Phe Thr Ile Ser Arg Asp Asp Ser Glu
 65                  70                  75                  80

Arg Ser Val Tyr Leu Gln Met Asn Arg Leu Arg Glu Glu Asp Thr Ala
                 85                  90                  95

Thr Tyr Tyr Cys Ser Arg Gly Ser Ser Glu Gly Phe Pro Tyr Trp Gly
            100                 105                 110

Gln Gly Thr Leu Val Thr Val Ser Ser Gly Ser Thr Ser Gly Ser Gly
        115                 120                 125

Lys Pro Gly Pro Gly Glu Gly Ser Thr Lys Gly Ala Pro Asp Ile Gln
    130                 135                 140

Met Thr Gln Ser Pro Ser Ser Leu Ser Val Ser Ala Gly Glu Lys Val
145                 150                 155                 160

Thr Leu Ser Cys Lys Ser Ser Gln Ser Leu Leu Asn Ser Gly Asn Gln
                165                 170                 175

Lys Asn Phe Leu Ala Trp Tyr Gln Gln Lys Pro Gly Gln Pro Pro Lys
            180                 185                 190

Leu Leu Ile Tyr Gly Ala Ser Thr Arg Glu Ser Gly Val Pro Ala Arg
        195                 200                 205

Phe Thr Gly Ser Gly Ser Gly Thr Asp Phe Thr Leu Thr Ile Ser Ser
    210                 215                 220

Val Gln Ala Glu Asp Gln Ala Val Tyr Tyr Cys Gln Asn Asp His Ser
```

```
                    225                 230                 235                 240
Tyr Pro Phe Thr Phe Gly Ser Gly Thr Lys Leu Glu Ile Lys Arg Ala
                245                 250                 255

Asp Ala Ala Pro Thr Val Ser
            260

<210> SEQ ID NO 30
<211> LENGTH: 251
<212> TYPE: PRT
<213> ORGANISM: Artificial Sequence
<220> FEATURE:
<223> OTHER INFORMATION: Description of Artificial Sequence: scFv VD2
      with specificity against Verticillium dahliae;
      originates from Mus musculus.

<400> SEQUENCE: 30

Met Ala Gln Ile Gln Leu Val Gln Ser Gly Pro Glu Leu Lys Lys Pro
 1               5                  10                  15

Gly Glu Thr Val Lys Ile Ser Cys Lys Val Ser Gly Asp Asn Phe Thr
            20                  25                  30

Asn Tyr Gly Met Gln Trp Val Lys Gln Ala Pro Gly Lys Gly Leu Lys
        35                  40                  45

Trp Met Gly Trp Ile Asn Thr Tyr Thr Gly Glu Ala Thr Tyr Ala Asp
 50                 55                  60

Asp Ser Lys Gly Arg Phe Ala Phe Ser Leu Glu Thr Ser Ala Ser Thr
 65                 70                  75                  80

Ala Tyr Leu Gln Ile Asn Asn Leu Lys Asn Glu Asp Thr Ala Thr Tyr
                85                  90                  95

Phe Cys Ala Arg Phe Leu Gly Asn Pro Tyr Tyr Val Met Asp Tyr Trp
            100                 105                 110

Gly Gln Gly Thr Ser Val Thr Val Ser Ala Gly Gly Gly Ser Gly
        115                 120                 125

Gly Gly Gly Ser Gly Gly Asp Ser Asp Val Leu Met Thr Gln Thr
    130                 135                 140

Pro Leu Ser Leu Pro Val Ser Leu Gly Asp Gln Ala Ser Ile Ser Cys
145                 150                 155                 160

Arg Ser Ser Gln Asn Ile Val His Ser Asn Gly Asn Thr Tyr Leu Gln
                165                 170                 175

Trp Tyr Leu Gln Lys Pro Gly Gln Ser Pro Lys Leu Leu Ile Tyr Lys
            180                 185                 190

Ala Ser Asn Arg Phe Ser Gly Val Pro Ala Arg Phe Ser Gly Ser Gly
        195                 200                 205

Ser Gly Thr Asp Phe Thr Leu Lys Ile Ser Arg Val Glu Ala Glu Asp
    210                 215                 220

Leu Gly Val Tyr Tyr Cys Phe Gln Gly Ser His Val Pro Tyr Thr Phe
225                 230                 235                 240

Gly Gly Gly Thr Lys Leu Glu Ile Lys Arg Ala
                245                 250

<210> SEQ ID NO 31
<211> LENGTH: 259
<212> TYPE: PRT
<213> ORGANISM: Artificial Sequence
<220> FEATURE:
<223> OTHER INFORMATION: Description of Artificial Sequence: scFv VDcw
      with specificity against Verticillium dahliae;
      originates from Mus musculus.

<400> SEQUENCE: 31
```

```
Met Ala Glu Val Lys Leu Leu Glu Ser Gly Pro Glu Leu Lys Pro
  1               5                  10                 15

Gly Glu Thr Val Lys Ile Ser Cys Lys Ala Ser Gly Tyr Thr Phe Thr
             20                  25                  30

Lys Tyr Gly Met Asn Trp Val Lys Gln Ala Pro Gly Lys Gly Leu Lys
         35                  40                  45

Trp Met Gly Trp Ile Asn Thr Tyr Thr Gly Glu Pro Thr Tyr Ala Asp
 50                  55                  60

Asp Phe Lys Gly Arg Phe Ala Phe Ser Leu Glu Thr Ser Thr Ser Thr
 65                  70                  75                  80

Ala Phe Leu Gln Ile Asn Asn Leu Lys Asn Glu Asp Thr Ala Thr Tyr
                 85                  90                  95

Phe Cys Ala Arg Tyr Tyr Gly Asn Pro Tyr Tyr Thr Met Asp Tyr Trp
             100                 105                 110

Gly Gln Gly Thr Ser Leu Thr Val Ser Ser Gly Gly Gly Gly Ser Gly
             115                 120                 125

Gly Gly Ser Gly Gly Gly Ser Asp Ile Val Leu Ser Gln Ser
 130                 135                 140

Pro Ser Ser Leu Ala Val Ser Val Gly Glu Lys Val Thr Met Ser Cys
145                 150                 155                 160

Lys Ser Ser Gln Ser Leu Leu Tyr Ser Ser Asn Gln Lys Asn Tyr Leu
                 165                 170                 175

Ala Trp Tyr Gln Gln Lys Pro Gly Gln Ser Pro Lys Leu Leu Ile Tyr
             180                 185                 190

Trp Ala Ser Thr Arg Glu Ser Gly Val Pro Asp Arg Phe Thr Gly Ser
             195                 200                 205

Gly Ser Gly Thr Asp Phe Thr Leu Thr Ile Ser Ser Val Lys Ala Glu
             210                 215                 220

Asp Leu Ala Val Tyr Tyr Cys Gln Gln Tyr Tyr Ser Tyr Pro Phe Thr
225                 230                 235                 240

Phe Gly Ser Gly Thr Lys Leu Glu Ile Lys Arg Ala Asp Ala Ala Pro
                 245                 250                 255

Thr Val Ser

<210> SEQ ID NO 32
<211> LENGTH: 248
<212> TYPE: PRT
<213> ORGANISM: Artificial Sequence
<220> FEATURE:
<223> OTHER INFORMATION: Description of Artificial Sequence: scFv VDM1
      with specificity against Verticillium dahliae;
      originates from Mus musculus.

<400> SEQUENCE: 32

Met Ala Gln Val Gln Leu Lys Gln Ser Gly Ala Glu Val Val Lys Pro
  1               5                  10                 15

Gly Ala Ser Val Lys Ile Ser Cys Lys Ala Ser Gly Tyr Arg Phe Thr
             20                  25                  30

Asp His Ala Ile His Trp Val Lys Gln Lys Pro Glu Gln Gly Leu Glu
         35                  40                  45

Trp Ile Gly Tyr Ile Ser Pro Gly Asn Gly Asp Ile Lys Tyr Asn Glu
 50                  55                  60

Lys Phe Arg Gly Lys Ala Thr Leu Thr Ala Asp Lys Ser Ser Ser Thr
 65                  70                  75                  80

Ala Tyr Met Gln Leu Asn Ser Leu Thr Ser Glu Asp Ser Ala Val Tyr
```

-continued

```
                85                  90                  95
Leu Cys Lys Arg Trp Pro Gly Ala Gly Met Asp Tyr Trp Gln Gly
            100                 105                 110

Thr Ser Val Thr Val Ser Ala Gly Gly Gly Ser Gly Gly Gly Gly
            115                 120                 125

Ser Gly Gly Gly Gly Ser Asp Ile Val Met Thr Gln Asn Glu Leu Ser
    130                 135                 140

Tyr Pro Val Thr Ser Gly Glu Ser Val Ser Ile Ser Cys Arg Ser Ser
145                 150                 155                 160

Lys Ser Leu Leu Tyr Lys Asp Gly Lys Thr Tyr Leu Asn Trp Phe Leu
                165                 170                 175

Gln Arg Pro Gly Gln Ser Pro Gln Leu Leu Ile Tyr Leu Met Ser Thr
                180                 185                 190

Arg Ala Ser Gly Val Ser Asp Arg Phe Ser Gly Ser Gly Ser Gly Thr
                195                 200                 205

Asp Phe Thr Leu Glu Ile Ser Arg Val Lys Ala Glu Asp Val Gly Val
    210                 215                 220

Tyr Tyr Cys Gln Gln Leu Val Glu Tyr Pro Leu Thr Phe Gly Ala Gly
225                 230                 235                 240

Thr Lys Leu Glu Leu Lys Arg Ala
                245

<210> SEQ ID NO 33
<211> LENGTH: 259
<212> TYPE: PRT
<213> ORGANISM: Artificial Sequence
<220> FEATURE:
<223> OTHER INFORMATION: Description of Artificial Sequence: scFv PL2
      with specificity against Phoma lingam; originates from
      Mus musculus.

<400> SEQUENCE: 33

Met Ala Glu Val Lys Leu Leu Glu Phe Gly Pro Glu Leu Lys Lys Pro
1               5                   10                  15

Gly Glu Thr Val Lys Ile Ser Cys Lys Ala Ser Gly Tyr Thr Phe Thr
            20                  25                  30

Lys Tyr Gly Met Asn Trp Val Lys Gln Ala Pro Gly Lys Gly Leu Lys
        35                  40                  45

Trp Met Gly Trp Ile Asn Thr Tyr Thr Gly Glu Pro Thr Tyr Ala Asp
    50                  55                  60

Asp Phe Lys Gly Arg Phe Ala Phe Ser Leu Glu Thr Ser Thr Ser Thr
65                  70                  75                  80

Ala Phe Leu Gln Ile Asn Asn Leu Lys Asn Glu Asp Thr Ala Thr Tyr
                85                  90                  95

Phe Cys Ala Arg Tyr Tyr Gly Asn Pro Tyr Tyr Thr Met Asp Tyr Trp
            100                 105                 110

Gly Gln Gly Thr Ser Leu Thr Val Ser Ser Gly Gly Gly Gly Ser Gly
        115                 120                 125

Gly Gly Gly Ser Gly Gly Gly Ser Asp Ile Val Leu Ser Gln Ser
    130                 135                 140

Pro Ser Ser Leu Ala Val Leu Val Gly Glu Lys Val Thr Met Ser Cys
145                 150                 155                 160

Lys Phe Ser Gln Ser Leu Leu Tyr Ser Ser Asn Gln Lys Asn Tyr Leu
                165                 170                 175

Ala Trp Tyr Gln Gln Lys Pro Gly Gln Ser Pro Lys Leu Leu Ile Tyr
                180                 185                 190
```

-continued

```
Trp Ala Ser Thr Arg Glu Ser Gly Val Pro Asp Arg Phe Thr Gly Ser
        195                 200                 205

Gly Ser Gly Thr Asp Phe Thr Leu Thr Ile Ser Ser Val Lys Ala Glu
    210                 215                 220

Asp Leu Ala Val Tyr Tyr Cys Gln Gln Tyr Tyr Ser Tyr Pro Phe Thr
225                 230                 235                 240

Phe Gly Ser Gly Thr Lys Leu Glu Ile Lys Arg Ala Asp Ala Ala Pro
                245                 250                 255

Thr Val Ser

<210> SEQ ID NO 34
<211> LENGTH: 259
<212> TYPE: PRT
<213> ORGANISM: Artificial Sequence
<220> FEATURE:
<223> OTHER INFORMATION: Description of Artificial Sequence: scFv PL2
      with specificity against Phoma lingam; originates from
      Mus musculus.

<400> SEQUENCE: 34

Met Ala Asp Val Gln Leu Gln Glu Ser Gly Pro Gly Leu Val Lys Pro
  1               5                  10                  15

Ser Gln Ser Leu Ser Leu Thr Cys Ser Val Thr Gly Tyr Ser Ile Thr
            20                  25                  30

Ser Gly Tyr Tyr Trp Asn Trp Ile Arg Gln Phe Pro Gly Asn Lys Leu
        35                  40                  45

Glu Trp Met Gly Tyr Ile Ser Tyr Asp Gly Thr Asn Asn Asn Asn Pro
     50                  55                  60

Ser Leu Lys Asn Arg Ile Ser Ile Thr Arg Asp Ala Ser Lys Asn Gln
 65                  70                  75                  80

Phe Phe Leu Lys Leu Asn Ser Val Thr Thr Glu Asp Thr Ala Thr Tyr
                85                  90                  95

His Cys Ala Arg Gly Ala Pro Tyr Tyr Gly Lys Gly Thr Trp Phe Pro
            100                 105                 110

Tyr Trp Gly Gln Gly Thr Leu Val Thr Val Ser Ser Gly Ser Thr Ser
        115                 120                 125

Gly Ser Gly Lys Pro Gly Pro Gly Glu Gly Ser Thr Lys Gly Ala Pro
    130                 135                 140

Glu Ile Val Leu Thr Gln Ser Pro Ser Ser Leu Ala Met Ser Val Gly
145                 150                 155                 160

Gln Lys Val Thr Met Ser Cys Lys Ser Ser Gln Ser Leu Leu Asn Ser
                165                 170                 175

Ser Asn Gln Lys Asn Tyr Leu Ala Trp Tyr Gln Gln Lys Pro Gly Gln
            180                 185                 190

Ser Pro Lys Leu Leu Val Tyr Phe Ala Ser Thr Arg Glu Ser Gly Val
        195                 200                 205

Pro Asp Arg Phe Ile Gly Ser Gly Ser Gly Thr Asp Phe Thr Leu Thr
    210                 215                 220

Ile Ser Ser Val Gln Ala Glu Asp Leu Ala Asp Tyr Phe Cys Gln Gln
225                 230                 235                 240

His Tyr Ser Thr Pro Pro Thr Phe Gly Gly Gly Thr Lys Leu Glu Ile
                245                 250                 255

Lys Arg Ala

<210> SEQ ID NO 35
```

<211> LENGTH: 261
<212> TYPE: PRT
<213> ORGANISM: Artificial Sequence
<220> FEATURE:
<223> OTHER INFORMATION: Description of Artificial Sequence: scFv PLp9
      with specificity against Phoma lingam; originates from
      Mus musculus.

<400> SEQUENCE: 35

```
Met Ala Val Thr Leu Asp Glu Ser Gly Gly Gly Leu Gln Thr Pro
 1               5                  10                  15

Gly Gly Ala Leu Ser Leu Val Cys Lys Ala Ser Gly Phe Asp Phe Lys
            20                  25                  30

Gly Tyr Glu Met Ala Trp Val Arg Gln Ala Pro Gly Lys Gly Leu Glu
        35                  40                  45

Trp Val Ala Ala Ile Ser Ser Gly Tyr Asn Thr Asn Tyr Gly Ala Ala
    50                  55                  60

Val Lys Gly Arg Ala Thr Ile Ser Arg Asn Asn Gly Gln Ser Thr Val
65                  70                  75                  80

Arg Leu Gln Leu Asn Asn Leu Arg Ala Glu Asp Thr Ala Thr Tyr Tyr
                85                  90                  95

Cys Ala Lys Thr His Gly Asp Tyr Gly Cys Ala Gly Asn Ala Trp Cys
            100                 105                 110

Ser Ala Gly Asn Ile Asp Ala Trp Gly His Gly Thr Glu Val Thr Val
        115                 120                 125

Ser Ser Gly Ser Thr Ser Gly Ser Gly Lys Pro Gly Pro Gly Glu Gly
    130                 135                 140

Ser Thr Lys Gly Ala Pro Gly Leu Thr Gln Ala Ser Ser Val Ser Ala
145                 150                 155                 160

Asn Pro Gly Glu Thr Val Lys Ile Thr Cys Ser Gly Gly Gly Ser Tyr
                165                 170                 175

Ala Gly Ser Tyr Tyr Tyr Gly Trp Tyr Gln Gln Lys Thr Pro Gly Ser
            180                 185                 190

Ala Pro Val Thr Val Ile Tyr Ser Asn Asp Lys Arg Pro Ser Asn Ile
        195                 200                 205

Pro Ser Arg Phe Ser Gly Ser Leu Ser Gly Ser Thr Asn Thr Leu Thr
    210                 215                 220

Ile Thr Gly Val Gln Val Asp Asp Glu Ala Val Tyr Phe Cys Gly Ala
225                 230                 235                 240

Tyr Asp Asn Asn Tyr Ala Gly Ile Phe Gly Ala Gly Thr Thr Leu Thr
                245                 250                 255

Val Leu Gly Gln Pro
            260
```

<210> SEQ ID NO 36
<211> LENGTH: 248
<212> TYPE: PRT
<213> ORGANISM: Artificial Sequence
<220> FEATURE:
<223> OTHER INFORMATION: Description of Artificial Sequence: scFv SS2
      with specificity against Sclerotinia sclerotiorum;
      originates from Mus musculus.

<400> SEQUENCE: 36

```
Met Ala Gln Val Gln Leu Gln Gln Ser Gly Thr Val Leu Ala Arg Pro
 1               5                  10                  15

Gly Ala Ser Val Lys Met Ser Cys Lys Ala Ser Gly Tyr Thr Phe Thr
            20                  25                  30
```

```
Ser Tyr Trp Met His Trp Val Lys Gln Arg Pro Gly Gln Gly Leu Glu
            35                  40                  45

Trp Ile Gly Ala Ile Tyr Pro Gly Asn Ser Asp Thr Ser Tyr Asn Gln
    50                  55                  60

Lys Phe Lys Gly Lys Ala Lys Leu Thr Ala Val Thr Ser Thr Ser Thr
65                  70                  75                  80

Ala Tyr Met Glu Leu Ser Ser Leu Thr Asn Glu Asp Ser Ala Val Tyr
                85                  90                  95

Tyr Cys Thr Arg Thr Asp Trp Asp Tyr Ala Met Asp Tyr Trp Gly Gln
            100                 105                 110

Gly Thr Ser Val Thr Val Ser Gly Ser Thr Ser Gly Ser Gly Lys
                115                 120                 125

Pro Gly Pro Gly Glu Gly Ser Thr Lys Gly Ala Pro Asp Ile Val Leu
            130                 135                 140

Phe Gln Ser Pro Val Ile Met Ser Ala Ser Pro Gly Glu Lys Val Thr
145                 150                 155                 160

Met Thr Cys Ser Ala Ser Ser Ser Val Asn Tyr Ile Tyr Trp Tyr Gln
                165                 170                 175

Trp Lys Ser Gly Thr Ser Pro Lys Arg Trp Ile Phe Asp Thr Ser Lys
            180                 185                 190

Leu Ala Ser Gly Val Pro Val Arg Phe Ser Gly Ser Gly Ser Gly Thr
                195                 200                 205

Ser Phe Ser Leu Thr Ile Ser Ser Met Glu Ala Glu Asp Ile Ala Thr
            210                 215                 220

Tyr Tyr Cys Gln Gln Trp Ser Ser Pro Pro Leu Thr Phe Gly Ala Gly
225                 230                 235                 240

Thr Lys Leu Glu Leu Lys Arg Ala
            245

<210> SEQ ID NO 37
<211> LENGTH: 301
<212> TYPE: PRT
<213> ORGANISM: Wheat

<400> SEQUENCE: 37

Met Glu Gln Cys Gly Ser Gln Ala Gly Gly Ala Thr Cys Pro Asn Cys
1               5                   10                  15

Leu Cys Cys Ser Lys Phe Gly Phe Cys Gly Ser Thr Ser Asp Tyr Cys
                20                  25                  30

Gly Asn Gly Cys Gln Ser Gln Cys Asn Gly Cys Ser Gly Gly Gly Thr
            35                  40                  45

Pro Val Pro Val Pro Thr Pro Thr Gly Gly Gly Val Ser Ser Ile Ile
    50                  55                  60

Ser Gln Ser Leu Phe Asp Gln Met Leu Leu His Arg Asn Asp Ala Ala
65                  70                  75                  80

Cys Gln Ala Lys Gly Phe Tyr Asn Tyr Gly Ala Phe Val Ala Ala Ala
                85                  90                  95

Asn Ser Phe Ser Gly Phe Ala Thr Thr Gly Gly Ala Asp Val Arg Lys
            100                 105                 110

Arg Glu Val Ala Ala Phe Leu Ala Gln Thr Ser His Glu Thr Thr Gly
                115                 120                 125

Gly Trp Pro Thr Ala Pro Asp Gly Pro Tyr Ser Trp Gly Tyr Cys Phe
            130                 135                 140

Asn Gln Glu Arg Gly Ala Ala Ser Asp Tyr Cys Ser Pro Asn Ser Gln
145                 150                 155                 160
```

```
Trp Pro Cys Ala Pro Gly Lys Lys Tyr Phe Gly Arg Gly Pro Ile Gln
                165                 170                 175

Ile Ser Tyr Asn Tyr Asn Tyr Gly Pro Ala Gly Arg Ala Ile Gly Thr
            180                 185                 190

Asp Leu Leu Asn Asn Pro Asp Leu Val Ala Thr Asp Ala Thr Val Ser
        195                 200                 205

Phe Lys Thr Ala Leu Trp Phe Trp Met Thr Pro Gln Ser Pro Lys Pro
    210                 215                 220

Ser Ser His Asp Val Ile Thr Gly Arg Trp Ser Pro Ser Gly Ala Asp
225                 230                 235                 240

Gln Ala Ala Gly Arg Val Pro Gly Tyr Gly Val Ile Thr Asn Ile Ile
                245                 250                 255

Asn Gly Gly Leu Glu Cys Gly Arg Gly Gln Asp Gly Arg Val Ala Asp
            260                 265                 270

Arg Ile Gly Phe Tyr Lys Arg Tyr Cys Asp Leu Leu Gly Val Ser Tyr
        275                 280                 285

Gly Asp Asn Leu Asp Cys Tyr Asn Gln Arg Pro Phe Ala
    290                 295                 300

<210> SEQ ID NO 38
<211> LENGTH: 53
<212> TYPE: PRT
<213> ORGANISM: Raphanus sativus

<400> SEQUENCE: 38

Met Ala Gln Lys Leu Cys Gln Arg Pro Ser Gly Thr Trp Ser Gly Val
1               5                   10                  15

Cys Gly Asn Asn Asn Ala Cys Lys Asn Gln Cys Ile Arg Leu Glu Lys
            20                  25                  30

Ala Arg His Gly Ser Cys Asn Tyr Val Phe Pro Ala His Lys Cys Ile
        35                  40                  45

Cys Tyr Phe Pro Cys
    50

<210> SEQ ID NO 39
<211> LENGTH: 52
<212> TYPE: PRT
<213> ORGANISM: Homo sapiens

<400> SEQUENCE: 39

Met Gly Arg Arg Arg Ser Val Gln Trp Cys Ala Val Ser Gln Pro
1               5                   10                  15

Glu Ala Thr Lys Cys Phe Gln Trp Gln Arg Asn Met Arg Lys Val Arg
            20                  25                  30

Gly Pro Pro Val Ser Cys Ile Lys Arg Asp Ser Pro Ile Gln Cys Ile
        35                  40                  45

Gln Ala Ile Ala
    50

<210> SEQ ID NO 40
<211> LENGTH: 52
<212> TYPE: PRT
<213> ORGANISM: Aspergillus giganteus

<400> SEQUENCE: 40

Met Ala Thr Tyr Asn Gly Lys Cys Tyr Lys Lys Asp Asn Ile Cys Lys
1               5                   10                  15
```

```
Tyr Lys Ala Gln Ser Gly Lys Thr Ala Ile Cys Lys Cys Tyr Val Lys
                20                  25                  30

Lys Cys Pro Arg Asp Gly Ala Lys Cys Glu Phe Asp Ser Tyr Lys Gly
            35                  40                  45

Lys Cys Tyr Cys
    50

<210> SEQ ID NO 41
<211> LENGTH: 35
<212> TYPE: PRT
<213> ORGANISM: Zea mays

<400> SEQUENCE: 41

Met Gly Arg Ser Gly Arg Gly Glu Cys Arg Arg Gln Cys Leu Arg Arg
 1               5                  10                  15

His Glu Gly Gln Pro Trp Glu Thr Gln Glu Cys Met Arg Arg Cys Arg
                20                  25                  30

Arg Arg Gly
        35

<210> SEQ ID NO 42
<211> LENGTH: 95
<212> TYPE: PRT
<213> ORGANISM: Allium cepa

<400> SEQUENCE: 42

Met Ala Gln Asn Ile Cys Pro Arg Val Asn Arg Ile Val Thr Pro Cys
 1               5                  10                  15

Val Ala Tyr Gly Leu Gly Arg Ala Pro Ile Ala Pro Cys Cys Arg Ala
                20                  25                  30

Leu Asn Asp Leu Arg Phe Val Asn Thr Arg Asn Leu Arg Arg Ala Ala
            35                  40                  45

Cys Arg Cys Leu Val Gly Val Val Asn Arg Asn Pro Gly Leu Arg Arg
    50                  55                  60

Asn Pro Arg Phe Gln Asn Ile Pro Arg Asp Cys Arg Asn Thr Phe Val
65                  70                  75                  80

Arg Pro Phe Trp Trp Arg Pro Arg Ile Gln Cys Gly Arg Ile Asn
                85                  90                  95

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: leader
      peptide (targeting the apoplast) derived from the heavy
      chain of an antibody from Mus musculus.

<400> SEQUENCE: 43

Met Asp Phe Gln Val Gln Ile Phe Ser Phe Leu Leu Ile Ser Ala Ser
 1               5                  10                  15

Val Ile Ile Ser Arg Gly Ser
                20

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: (G4S)2
      linker
```

-continued

```
<400> SEQUENCE: 44

Gly Gly Gly Gly Ser Gly Gly Gly Gly Ser
 1               5                  10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: cmyc tag

<400> SEQUENCE: 45

Glu Gln Lys Leu Ile Ser Glu Glu Asp Leu Gly Ala Leu Asp
 1               5                  10

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: His6 tag

<400> SEQUENCE: 46

His His His His His His
 1               5

<210> SEQ ID NO 47
<211> LENGTH: 625
<212> TYPE: PRT
<213> ORGANISM: Artificial Sequence
<220> FEATURE:
<223> OTHER INFORMATION: Description of Artificial Sequence: fusion
      protein comprising the leader peptide - chitinase - linker
      - scFv CWPD2 - cmyc/His6.

<400> SEQUENCE: 47

Met Asp Phe Gln Val Gln Ile Phe Ser Phe Leu Leu Ile Ser Ala Ser
 1               5                  10                  15

Val Ile Ile Ser Arg Gly Ser Met Glu Gln Cys Gly Ser Gln Ala Gly
                20                  25                  30

Gly Ala Thr Cys Pro Asn Cys Leu Cys Cys Ser Lys Phe Gly Phe Cys
            35                  40                  45

Gly Ser Thr Ser Asp Tyr Cys Gly Asn Gly Cys Gln Ser Gln Cys Asn
        50                  55                  60

Gly Cys Ser Gly Gly Gly Thr Pro Val Pro Val Pro Thr Pro Thr Gly
    65                  70                  75                  80

Gly Gly Val Ser Ser Ile Ile Ser Gln Ser Leu Phe Asp Gln Met Leu
                85                  90                  95

Leu His Arg Asn Asp Ala Ala Cys Gln Ala Lys Gly Phe Tyr Asn Tyr
               100                 105                 110

Gly Ala Phe Val Ala Ala Ala Asn Ser Phe Ser Gly Phe Ala Thr Thr
           115                 120                 125

Gly Gly Ala Asp Val Arg Lys Arg Glu Val Ala Ala Phe Leu Ala Gln
       130                 135                 140

Thr Ser His Glu Thr Thr Gly Gly Trp Pro Thr Ala Pro Asp Gly Pro
145                 150                 155                 160

Tyr Ser Trp Gly Tyr Cys Phe Asn Gln Glu Arg Gly Ala Ala Ser Asp
               165                 170                 175

Tyr Cys Ser Pro Asn Ser Gln Trp Pro Cys Ala Pro Gly Lys Lys Tyr
           180                 185                 190
```

-continued

```
Phe Gly Arg Gly Pro Ile Gln Ile Ser Tyr Asn Tyr Asn Tyr Gly Pro
        195                 200                 205

Ala Gly Arg Ala Ile Gly Thr Asp Leu Leu Asn Asn Pro Asp Leu Val
    210                 215                 220

Ala Thr Asp Ala Thr Val Ser Phe Lys Thr Ala Leu Trp Phe Trp Met
225                 230                 235                 240

Thr Pro Gln Ser Pro Lys Pro Ser Ser His Asp Val Ile Thr Gly Arg
                245                 250                 255

Trp Ser Pro Ser Gly Ala Asp Gln Ala Ala Gly Arg Val Pro Gly Tyr
            260                 265                 270

Gly Val Ile Thr Asn Ile Ile Asn Gly Gly Leu Glu Cys Gly Arg Gly
        275                 280                 285

Gln Asp Gly Arg Val Ala Asp Arg Ile Gly Phe Tyr Lys Arg Tyr Cys
    290                 295                 300

Asp Leu Leu Gly Val Ser Tyr Gly Asp Asn Leu Asp Cys Tyr Asn Gln
305                 310                 315                 320

Arg Pro Phe Ala Val Asp Gly Gly Gly Ser Gly Gly Gly Ser
                325                 330                 335

Ala Ala Gln Pro Ala Met Ala Ala Val Thr Leu Asp Glu Ser Gly Gly
            340                 345                 350

Gly Leu Gln Thr Pro Gly Gly Gly Leu Ser Leu Val Cys Lys Gly Ser
        355                 360                 365

Gly Phe Asp Phe Ser Ser Asp Thr Met Met Trp Val Arg Gln Ala Pro
    370                 375                 380

Gly Lys Gly Leu Glu Phe Val Ala Gly Ile Ser Gly Asp Gly Ser Asp
385                 390                 395                 400

Thr Asn Tyr Gly Ser Ala Val Lys Gly Arg Ala Thr Ile Ser Arg Asp
                405                 410                 415

Asn Gly Gln Ser Thr Val Arg Leu Gln Leu Asn Asn Leu Arg Ala Glu
            420                 425                 430

Asp Thr Ala Thr Tyr Tyr Cys Thr Arg Gly Pro Cys Ser Pro Thr Lys
        435                 440                 445

Asn Cys Ala Ala Asp Arg Ile Asp Ala Trp Gly His Gly Thr Glu Val
    450                 455                 460

Thr Val Ser Ser Gly Ser Thr Ser Gly Ser Gly Lys Pro Gly Pro Gly
465                 470                 475                 480

Glu Gly Ser Thr Lys Gly Ala Pro Ala Leu Thr Gln Pro Ser Ser Val
                485                 490                 495

Ser Ala Asn Leu Gly Gly Thr Val Glu Ile Thr Cys Ser Gly Gly Gly
            500                 505                 510

Tyr Arg Tyr Gly Trp Phe Gln Gln Lys Ser Pro Gly Ser Ala Pro Val
        515                 520                 525

Thr Val Ile Tyr Trp Asp Asp Ser Ala Asn Arg Pro Ser Asn Ile
    530                 535                 540

Pro Ser Arg Phe Ser Gly Ser Thr Ser Gly Ser Thr Ala Thr Leu Thr
545                 550                 555                 560

Ile Thr Gly Val Gln Ala Asp Asp Glu Ala Val Tyr Phe Cys Gly Ser
                565                 570                 575

Tyr Asp Arg Ser Ser Gly Tyr Val Ser Ile Phe Gly Ala Gly Thr Thr
            580                 585                 590

Leu Thr Val Leu Gly Gln Pro Val Asp Ala Ala Glu Gln Lys Leu
        595                 600                 605
```

-continued

```
Ile Ser Glu Glu Asp Leu Gly Ala Leu Asp His His His His His
610                 615                 620

Val
625

<210> SEQ ID NO 48
<211> LENGTH: 618
<212> TYPE: PRT
<213> ORGANISM: Artificial Sequence
<220> FEATURE:
<223> OTHER INFORMATION: Description of Artificial Sequence: fusion
      protein comprising the leader peptide - chitinase - linker
      - scFv VD2 - cmyc/His6.

<400> SEQUENCE: 48

Met Asp Phe Gln Val Gln Ile Phe Ser Phe Leu Leu Ile Ser Ala Ser
1               5                   10                  15

Val Ile Ile Ser Arg Gly Ser Met Glu Gln Cys Gly Ser Gln Ala Gly
                20                  25                  30

Gly Ala Thr Cys Pro Asn Cys Leu Cys Cys Ser Lys Phe Gly Phe Cys
            35                  40                  45

Gly Ser Thr Ser Asp Tyr Cys Gly Asn Gly Cys Gln Ser Gln Cys Asn
        50                  55                  60

Gly Cys Ser Gly Gly Thr Pro Val Pro Val Pro Thr Pro Thr Pro Gly
65                  70                  75                  80

Gly Gly Val Ser Ser Ile Ile Ser Gln Ser Leu Phe Asp Gln Met Leu
                85                  90                  95

Leu His Arg Asn Asp Ala Ala Cys Gln Ala Lys Gly Phe Tyr Asn Tyr
            100                 105                 110

Gly Ala Phe Val Ala Ala Asn Ser Phe Ser Gly Phe Ala Thr Thr
        115                 120                 125

Gly Gly Ala Asp Val Arg Lys Arg Glu Val Ala Ala Phe Leu Ala Gln
    130                 135                 140

Thr Ser His Glu Thr Thr Gly Gly Trp Pro Thr Ala Pro Asp Gly Pro
145                 150                 155                 160

Tyr Ser Trp Gly Tyr Cys Phe Asn Gln Glu Arg Gly Ala Ala Ser Asp
                165                 170                 175

Tyr Cys Ser Pro Asn Ser Gln Trp Pro Cys Ala Pro Gly Lys Lys Tyr
            180                 185                 190

Phe Gly Arg Gly Pro Ile Gln Ile Ser Tyr Asn Tyr Asn Tyr Gly Pro
        195                 200                 205

Ala Gly Arg Ala Ile Gly Thr Asp Leu Leu Asn Asn Pro Asp Leu Val
    210                 215                 220

Ala Thr Asp Ala Thr Val Ser Phe Lys Thr Ala Leu Trp Phe Trp Met
225                 230                 235                 240

Thr Pro Gln Ser Pro Lys Pro Ser Ser His Asp Val Ile Thr Gly Arg
                245                 250                 255

Trp Ser Pro Ser Gly Ala Asp Gln Ala Ala Gly Arg Val Pro Gly Tyr
            260                 265                 270

Gly Val Ile Thr Asn Ile Ile Asn Gly Gly Leu Glu Cys Gly Arg Gly
        275                 280                 285

Gln Asp Gly Arg Val Ala Asp Arg Ile Gly Phe Tyr Lys Arg Tyr Cys
    290                 295                 300

Asp Leu Leu Gly Val Ser Tyr Gly Asp Asn Leu Asp Cys Tyr Asn Gln
305                 310                 315                 320

Arg Pro Phe Ala Val Asp Gly Gly Gly Ser Gly Gly Gly Gly Ser
```

```
                 325                 330                 335
Ala Ala Gln Pro Ala Met Ala Gln Ile Gln Leu Val Gln Ser Gly Pro
            340                 345                 350

Glu Leu Lys Lys Pro Gly Glu Thr Val Lys Ile Ser Cys Lys Val Ser
        355                 360                 365

Gly Asp Asn Phe Thr Asn Tyr Gly Met Gln Trp Val Lys Gln Ala Pro
    370                 375                 380

Gly Lys Gly Leu Lys Trp Met Gly Trp Ile Asn Thr Tyr Thr Gly Glu
385                 390                 395                 400

Ala Thr Tyr Ala Asp Asp Ser Lys Gly Arg Phe Ala Phe Ser Leu Glu
            405                 410                 415

Thr Ser Ala Ser Thr Ala Tyr Leu Gln Ile Asn Asn Leu Lys Asn Glu
        420                 425                 430

Asp Thr Ala Thr Tyr Phe Cys Ala Arg Phe Leu Gly Asn Pro Tyr Tyr
    435                 440                 445

Val Met Asp Tyr Trp Gly Gln Gly Thr Ser Val Thr Val Ser Ala Gly
    450                 455                 460

Gly Gly Gly Ser Gly Gly Gly Ser Gly Gly Gly Asp Ser Asp Val
465                 470                 475                 480

Leu Met Thr Gln Thr Pro Leu Ser Leu Pro Val Ser Leu Gly Asp Gln
            485                 490                 495

Ala Ser Ile Ser Cys Arg Ser Ser Gln Asn Ile Val His Ser Asn Gly
        500                 505                 510

Asn Thr Tyr Leu Gln Trp Tyr Leu Gln Lys Pro Gly Gln Ser Pro Lys
    515                 520                 525

Leu Leu Ile Tyr Lys Ala Ser Asn Arg Phe Ser Gly Val Pro Ala Arg
    530                 535                 540

Phe Ser Gly Ser Gly Ser Gly Thr Asp Phe Thr Leu Lys Ile Ser Arg
545                 550                 555                 560

Val Glu Ala Glu Asp Leu Gly Val Tyr Tyr Cys Phe Gln Gly Ser His
            565                 570                 575

Val Pro Tyr Thr Phe Gly Gly Gly Thr Lys Leu Glu Ile Lys Arg Ala
        580                 585                 590

Val Asp Ala Ala Ala Glu Gln Lys Leu Ile Ser Glu Glu Asp Leu Gly
    595                 600                 605

Ala Leu Asp His His His His His His Val
    610                 615
```

<210> SEQ ID NO 49
<211> LENGTH: 626
<212> TYPE: PRT
<213> ORGANISM: Artificial Sequence
<220> FEATURE:
<223> OTHER INFORMATION: Description of Artificial Sequence: fusion
      protein comprising the leader peptide - chitinase- linker
      - scFv PL2 - cmyc/His6.

<400> SEQUENCE: 49

```
Met Asp Phe Gln Val Gln Ile Phe Ser Phe Leu Leu Ile Ser Ala Ser
1               5                   10                  15

Val Ile Ile Ser Arg Gly Ser Met Glu Gln Cys Gly Ser Gln Ala Gly
            20                  25                  30

Gly Ala Thr Cys Pro Asn Cys Leu Cys Cys Ser Lys Phe Gly Phe Cys
        35                  40                  45

Gly Ser Thr Ser Asp Tyr Cys Gly Asn Gly Cys Gln Ser Gln Cys Asn
    50                  55                  60
```

```
Gly Cys Ser Gly Gly Gly Thr Pro Val Pro Val Pro Thr Pro Thr Gly
 65                  70                  75                  80

Gly Gly Val Ser Ser Ile Ile Ser Gln Ser Leu Phe Asp Gln Met Leu
             85                  90                  95

Leu His Arg Asn Asp Ala Ala Cys Gln Ala Lys Gly Phe Tyr Asn Tyr
            100                 105                 110

Gly Ala Phe Val Ala Ala Asn Ser Phe Ser Gly Phe Ala Thr Thr
        115                 120                 125

Gly Gly Ala Asp Val Arg Lys Arg Glu Val Ala Ala Phe Leu Ala Gln
        130                 135                 140

Thr Ser His Glu Thr Thr Gly Gly Trp Pro Thr Ala Pro Asp Gly Pro
145                 150                 155                 160

Tyr Ser Trp Gly Tyr Cys Phe Asn Gln Glu Arg Gly Ala Ala Ser Asp
                165                 170                 175

Tyr Cys Ser Pro Asn Ser Gln Trp Pro Cys Ala Pro Gly Lys Lys Tyr
            180                 185                 190

Phe Gly Arg Gly Pro Ile Gln Ile Ser Tyr Asn Tyr Asn Tyr Gly Pro
        195                 200                 205

Ala Gly Arg Ala Ile Gly Thr Asp Leu Leu Asn Asn Pro Asp Leu Val
        210                 215                 220

Ala Thr Asp Ala Thr Val Ser Phe Lys Thr Ala Leu Trp Phe Trp Met
225                 230                 235                 240

Thr Pro Gln Ser Pro Lys Pro Ser Ser His Asp Val Ile Thr Gly Arg
                245                 250                 255

Trp Ser Pro Ser Gly Ala Asp Gln Ala Ala Gly Arg Val Pro Gly Tyr
            260                 265                 270

Gly Val Ile Thr Asn Ile Ile Asn Gly Gly Leu Glu Cys Gly Arg Gly
        275                 280                 285

Gln Asp Gly Arg Val Ala Asp Arg Ile Gly Phe Tyr Lys Arg Tyr Cys
        290                 295                 300

Asp Leu Leu Gly Val Ser Tyr Gly Asp Asn Leu Asp Cys Tyr Asn Gln
305                 310                 315                 320

Arg Pro Phe Ala Val Asp Gly Gly Gly Ser Gly Gly Gly Ser
                325                 330                 335

Ala Ala Gln Pro Ala Met Ala Asp Val Gln Leu Gln Glu Ser Gly Pro
        340                 345                 350

Gly Leu Val Lys Pro Ser Gln Ser Leu Ser Leu Thr Cys Ser Val Thr
        355                 360                 365

Gly Tyr Ser Ile Thr Ser Gly Tyr Tyr Trp Asn Trp Ile Arg Gln Phe
    370                 375                 380

Pro Gly Asn Lys Leu Glu Trp Met Gly Tyr Ile Ser Tyr Asp Gly Thr
385                 390                 395                 400

Asn Asn Asn Asn Pro Ser Leu Lys Asn Arg Ile Ser Ile Thr Arg Asp
                405                 410                 415

Ala Ser Lys Asn Gln Phe Phe Leu Lys Leu Asn Ser Val Thr Thr Glu
            420                 425                 430

Asp Thr Ala Thr Tyr His Cys Ala Arg Gly Ala Pro Tyr Tyr Gly Lys
            435                 440                 445

Gly Thr Trp Phe Pro Tyr Trp Gly Gln Gly Thr Leu Val Thr Val Ser
        450                 455                 460

Ser Gly Ser Thr Ser Gly Ser Gly Lys Pro Gly Pro Gly Glu Gly Ser
465                 470                 475                 480
```

```
Thr Lys Gly Ala Pro Glu Ile Val Leu Thr Gln Ser Pro Ser Ser Leu
                485                 490                 495

Ala Met Ser Val Gly Gln Lys Val Thr Met Ser Cys Lys Ser Ser Gln
                500                 505                 510

Ser Leu Leu Asn Ser Ser Asn Gln Lys Asn Tyr Leu Ala Trp Tyr Gln
                515                 520                 525

Gln Lys Pro Gly Gln Ser Pro Lys Leu Leu Val Tyr Phe Ala Ser Thr
            530                 535                 540

Arg Glu Ser Gly Val Pro Asp Arg Phe Ile Gly Ser Gly Ser Gly Thr
545                 550                 555                 560

Asp Phe Thr Leu Thr Ile Ser Ser Val Gln Ala Glu Asp Leu Ala Asp
                565                 570                 575

Tyr Phe Cys Gln Gln His Tyr Ser Thr Pro Pro Thr Phe Gly Gly Gly
                580                 585                 590

Thr Lys Leu Glu Ile Lys Arg Ala Val Asp Ala Ala Glu Gln Lys
                595                 600                 605

Leu Ile Ser Glu Glu Asp Leu Gly Ala Leu Asp His His His His
            610                 615                 620

His Val
625

<210> SEQ ID NO 50
<211> LENGTH: 615
<212> TYPE: PRT
<213> ORGANISM: Artificial Sequence
<220> FEATURE:
<223> OTHER INFORMATION: Description of Artificial Sequence: fusion
      protein comprising the leader peptide - chitinase - linker
      - scFv SS2 - cmyc/His6.

<400> SEQUENCE: 50

Met Asp Phe Gln Val Gln Ile Phe Ser Phe Leu Leu Ile Ser Ala Ser
  1               5                  10                  15

Val Ile Ile Ser Arg Gly Ser Met Glu Gln Cys Gly Ser Gln Ala Gly
                20                  25                  30

Gly Ala Thr Cys Pro Asn Cys Leu Cys Cys Ser Lys Phe Gly Phe Cys
            35                  40                  45

Gly Ser Thr Ser Asp Tyr Cys Gly Asn Gly Cys Gln Ser Gln Cys Asn
        50                  55                  60

Gly Cys Ser Gly Gly Gly Thr Pro Val Pro Val Pro Thr Pro Thr Gly
 65                 70                  75                  80

Gly Gly Val Ser Ser Ile Ile Ser Gln Ser Leu Phe Asp Gln Met Leu
                85                  90                  95

Leu His Arg Asn Asp Ala Ala Cys Gln Ala Lys Gly Phe Tyr Asn Tyr
                100                 105                 110

Gly Ala Phe Val Ala Ala Asn Ser Phe Ser Gly Phe Ala Thr Thr
            115                 120                 125

Gly Gly Ala Asp Val Arg Lys Arg Glu Val Ala Ala Phe Leu Ala Gln
        130                 135                 140

Thr Ser His Glu Thr Thr Gly Gly Trp Pro Thr Ala Pro Asp Gly Pro
145                 150                 155                 160

Tyr Ser Trp Gly Tyr Cys Phe Asn Gln Glu Arg Gly Ala Ala Ser Asp
                165                 170                 175

Tyr Cys Ser Pro Asn Ser Gln Trp Pro Cys Ala Pro Gly Lys Lys Tyr
                180                 185                 190

Phe Gly Arg Gly Pro Ile Gln Ile Ser Tyr Asn Tyr Asn Tyr Gly Pro
```

```
              195                 200                 205
Ala Gly Arg Ala Ile Gly Thr Asp Leu Leu Asn Asn Pro Asp Leu Val
    210                 215                 220

Ala Thr Asp Ala Thr Val Ser Phe Lys Thr Ala Leu Trp Phe Trp Met
225                 230                 235                 240

Thr Pro Gln Ser Pro Lys Pro Ser Ser His Asp Val Ile Thr Gly Arg
                245                 250                 255

Trp Ser Pro Ser Gly Ala Asp Gln Ala Ala Gly Arg Val Pro Gly Tyr
                260                 265                 270

Gly Val Ile Thr Asn Ile Ile Asn Gly Leu Glu Cys Gly Arg Gly
                275                 280                 285

Gln Asp Gly Arg Val Ala Asp Arg Ile Gly Phe Tyr Lys Arg Tyr Cys
    290                 295                 300

Asp Leu Leu Gly Val Ser Tyr Gly Asp Asn Leu Asp Cys Tyr Asn Gln
305                 310                 315                 320

Arg Pro Phe Ala Val Asp Gly Gly Gly Ser Gly Gly Gly Ser
                325                 330                 335

Ala Ala Gln Pro Ala Met Ala Gln Val Gln Leu Gln Gln Ser Gly Thr
                340                 345                 350

Val Leu Ala Arg Pro Gly Ala Ser Val Lys Met Ser Cys Lys Ala Ser
                355                 360                 365

Gly Tyr Thr Phe Thr Ser Tyr Trp Met His Trp Val Lys Gln Arg Pro
    370                 375                 380

Gly Gln Gly Leu Glu Trp Ile Gly Ala Ile Tyr Pro Gly Asn Ser Asp
385                 390                 395                 400

Thr Ser Tyr Asn Gln Lys Phe Lys Gly Lys Ala Lys Leu Thr Ala Val
                405                 410                 415

Thr Ser Thr Ser Thr Ala Tyr Met Glu Leu Ser Ser Leu Thr Asn Glu
                420                 425                 430

Asp Ser Ala Val Tyr Tyr Cys Thr Arg Thr Asp Trp Asp Tyr Ala Met
    435                 440                 445

Asp Tyr Trp Gly Gln Gly Thr Ser Val Thr Val Ser Ser Gly Ser Thr
450                 455                 460

Ser Gly Ser Gly Lys Pro Gly Pro Gly Glu Gly Ser Thr Lys Gly Ala
465                 470                 475                 480

Pro Asp Ile Val Leu Phe Gln Ser Pro Val Ile Met Ser Ala Ser Pro
                485                 490                 495

Gly Glu Lys Val Thr Met Thr Cys Ser Ala Ser Ser Ser Val Asn Tyr
                500                 505                 510

Ile Tyr Trp Tyr Gln Trp Lys Ser Gly Thr Ser Pro Lys Arg Trp Ile
    515                 520                 525

Phe Asp Thr Ser Lys Leu Ala Ser Gly Val Pro Val Arg Phe Ser Gly
    530                 535                 540

Ser Gly Ser Gly Thr Ser Phe Ser Leu Thr Ile Ser Ser Met Glu Ala
545                 550                 555                 560

Glu Asp Ile Ala Thr Tyr Tyr Cys Gln Gln Trp Ser Ser Pro Pro Leu
                565                 570                 575

Thr Phe Gly Ala Gly Thr Lys Leu Glu Leu Lys Arg Ala Val Asp Ala
                580                 585                 590

Ala Ala Glu Gln Lys Leu Ile Ser Glu Glu Asp Leu Gly Ala Leu Asp
    595                 600                 605

His His His His His Val
    610                 615
```

<210> SEQ ID NO 51
<211> LENGTH: 981
<212> TYPE: DNA
<213> ORGANISM: Artificial Sequence
<220> FEATURE:
<223> OTHER INFORMATION: Description of Artificial Sequence: precursor
fusion protein comprising the AG - linker -
scFv CWPD5.

<400> SEQUENCE: 51

```
atggccacct acaacggcaa gtgctacaag aaggacaaca tctgcaagta caaggcccag      60
agcggcaaga ccgctatctg caagtgctac gtcaagaagt gcccaaggga cggagccaag     120
tgcgagttcg acagctacaa gggcaagtgc tactgcgtcg acggtggagg cggatctggt     180
ggcggtggaa gcgcggccca gccggccatg gctgccgtga cgttggacga gtccggggc     240
ggcctccaga cgcccggagg agggctcagc ctcgtctgca agggctccgg gtttgacttc     300
agcagtgaca ccatgatgtg ggtgcgccag gcgcccggca aggggttgga attcgtcgct     360
ggtattagtg gtgatggtag tgacacaaac tacgggtcgg cggtgaaggg ccgtgccacc     420
atctcgaggg acaacgggca gagcacagtg aggctgcagc tgaacaacct cagggctgag     480
gacaccgcca cctactactg caccagaggt ccttgtagtc ctacgaagaa ttgtgctgct     540
gatcgtatcg acgcatgggg ccacgggacc gaggtcaccg tctcctcagg ctccacctca     600
ggctccggta aacctggccc aggggaggga tcaactaagg gcgcgcctgc gctgactcag     660
ccgtcctcgg tgtcagcaaa cctgggagga accgtcgaga tcacctgctc cggggtggc     720
tataggtatg ctggttccag cagaagtct cctggcagtg ccctgtcac agtgatctac     780
tgggatgatg acagcgccaa cagaccctcg aacatcccct tcacgattct cggttccaca     840
tctggctcca cagccacatt aaccatcact ggggtccaag ccgacgacga ggctgtctat     900
ttctgtggga gctatgacag gagtagtggt tatgtttcta tatttggggc cgggacaacc     960
ctgaccgtcc taggccagcc c                                               981
```

<210> SEQ ID NO 52
<211> LENGTH: 984
<212> TYPE: DNA
<213> ORGANISM: Artificial Sequence
<220> FEATURE:
<223> OTHER INFORMATION: Description of Artificial Sequence: precursor
fusion protein comprising the RS - linker -
scFv CWPD2.

<400> SEQUENCE: 52

```
atggctcaga gttgtgtca gaggccaagt gggacatggt caggagtctg tggaaataat      60
aacgcgtgca agaatcagtg cattcgactt gagaaagcac gacatgggtc ttgcaactat     120
gtcttcccag ctcacaagtg tatctgttat ttcccttgtg tcgacggtgg aggcggatct     180
ggtggcggtg aagcgcggc ccagccggcc atggctgccg tgacgttgga cgagtccggg     240
gcggcctcc agacgcccgg aggagggctc agcctcgtct gcaagggctc cgggtttgac     300
ttcagcagtg acaccatgat gtgggtgcgc caggcgcccg gcaaggggtt ggaattcgtc     360
gctggtatta gtggtgatgg tagtgacaca aactacgggt cggcggtgaa gggccgtgcc     420
accatctcga gggacaacgg gcagagcaca gtgaggctgc agctgaacaa cctcagggct     480
gaggacaccg ccacctacta ctgcaccaga ggtccttgta gtcctacgaa gaattgtgct     540
gctgatcgta tcgacgcatg gggccacggg accgaggtca ccgtctcctc aggctccacc     600
```

-continued

```
tcaggctccg gtaaacctgg cccaggggag ggatcaacta agggcgcgcc tgcgctgact      660
cagccgtcct cggtgtcagc aaacctggga ggaaccgtcg agatcacctg ctccgggggt      720
ggctataggt atggctggtt ccagcagaag tctcctggca gtgccccgt  cacagtgatc      780 tactgggatg atgacagcgc caacagaccc tcgaacatcc cttcacgatt ctccggttcc      840
acatctggct ccacagccac attaaccatc actggggtcc aagccgacga cgaggctgtc      900
tatttctgtg ggagctatga caggagtagt ggttatgttt ctatatttgg ggccgggaca      960
accctgaccg tcctaggcca gccc                                             984
```

<210> SEQ ID NO 53
<211> LENGTH: 981
<212> TYPE: DNA
<213> ORGANISM: Artificial Sequence
<220> FEATURE:
<223> OTHER INFORMATION: Description of Artificial Sequence: precursor
      fusion protein comprising the lactoferricin -
      linker - scFv CWPD2.

<400> SEQUENCE: 53

```
atgggccgta ggagaaggag tgttcagtgg tgcgccgtat cccaacccga ggccacaaaa       60
tgcttccaat ggcaaaggaa tatgagaaaa gtgcgtggcc ctcctgtcag ctgcataaag      120
agagactccc ccatccagtg tatccaggcc attgcggtcg acgtggaggc ggatctggt      180 ggcggtggaa gcgcggccca gccggccatg gctgccgtga cgttggacga gtccgggggc      240
ggcctccaga cgcccggagg agggctcagc ctcgtctgca agggctccgg gtttgacttc      300
agcagtgaca ccatgatgtg ggtgcgccag gcgcccggca aggggttgga attcgtcgct      360
ggtattagtg gtgatggtag tgacacaaac tacgggtcgg cggtgaaggg ccgtgccacc      420
atctcgaggg acaacgggca gagcacagtg aggctgcagc tgaacaacct cagggctgag      480
gacaccgcca cctactactg caccagaggt ccttgtagtc ctacgaagaa ttgtgctgct      540
gatcgtatcg acgcatgggg ccacgggacc gaggtcaccg tctcctcagg ctccacctca      600
ggctccggta aacctggccc aggggaggga tcaactaagg gcgcgcctgc gctgactcag      660
ccgtcctcgg tgtcagcaaa cctgggagga accgtcgaga tcacctgctc cggggggtggc      720 tataggtatg gctggttcca gcagaagtct cctggcagtg cccctgtcac agtgatctac      780
tgggatgatg acagcgccaa cagaccctcg aacatccctt cacgattctc cggttccaca      840
tctggctcca cagccacatt aaccatcact ggggtccaag ccgacgacga ggctgtctat      900
ttctgtggga gctatgacag gagtagtggt tatgtttcta tatttggggc cgggacaacc      960
ctgaccgtcc taggccagcc c                                                981
```

<210> SEQ ID NO 54
<211> LENGTH: 1728
<212> TYPE: DNA
<213> ORGANISM: Artificial Sequence
<220> FEATURE:
<223> OTHER INFORMATION: Description of Artificial Sequence: precursor
      fusion protein comprising the chitinase - linker -
      scFv CWPD2.

<400> SEQUENCE: 54

```
atggagcagt gcggctcgca ggccggcggg gcgacgtgcc ccaactgcct ctgctgcagc       60
aagttcggct ctgcggctc  cacctccgac tactgcggca acggctgcca gagccagtgc      120
aacggctgca gcggcggcgg caccccgta  ccggtaccga ccccaccgg  cggcggcgtg      180 tcctccatta tctcgcagtc gctcttcgac cagatgctgc tgcaccgcaa cgatgcggcg      240
```

| | |
|---|---|
| tgccaggcca aggggttcta caactacggc gcctttgtag ccgccgccaa ctcgttctcg | 300 |
| ggcttcgcga ccacgggtgg cgccgacgtc aggaagcgcg aggtggccgc gttcctcgct | 360 |
| cagacctccc acgagaccac cggcgggtgg ccaacggcgc ccgacggccc ctactcgtgg | 420 |
| ggctactgct tcaaccagga gcgcggcgcc gcctccgact actgctcgcc gaactcacag | 480 |
| tggccgtgcg cgccgggcaa gaagtacttc gggcgcgggc ccatccagat ctcatacaac | 540 |
| tacaactacg gccggctggg cgggccatc gggaccgacc tgctcaacaa cccggacctc | 600 |
| gtggcgacgg atgcgaccgt gtcgtttaag acggcgctgt ggttctggat gacgccgcag | 660 |
| tcacctaaac cttcgagcca cgacgtgatt acgggccggt ggagcccctc gggcgccgac | 720 |
| caggcggcgg ggagggtgcc tgggtacggt gtgatcacta acatcatcaa cggtgggctc | 780 |
| gagtgcgggc gcgggcagga cggccgtgtt gccgaccgga tcgggttcta caagcgctac | 840 |
| tgcgacctac tcggcgtcag ctacggcgac aacctggact gctacaacca gaggccgttc | 900 |
| gccgtcgacg gtggaggcgg atctggtggc ggtggaagcg cggcccagcc ggccatggct | 960 |
| gccgtgacgt tggacgagtc cggggcgcgg ctccagacgc ccggaggagg gctcagcctc | 1020 |
| gtctgcaagg gctccgggtt tgacttcagc agtgacacca tgatgtgggt gcgccaggcg | 1080 |
| cccggcaagg ggttggaatt cgtcgctggt attagtggtg atggtagtga cacaaactac | 1140 |
| gggtcggcgg tgaagggccg tgccaccatc tcgagggaca cgggcagag cacagtgagg | 1200 |
| ctgcagctga caacctcag ggctgaggac accgccacct actactgcac cagaggtcct | 1260 |
| tgtagtccta cgaagaattg tgctgctgat cgtatcgacg catggggcca cgggaccgag | 1320 |
| gtcaccgtct cctcaggctc cacctcaggc tccggtaaac ctggcccagg ggagggatca | 1380 |
| actaagggcg cgcctgcgct gactcagccg tcctcggtgt cagcaaacct gggaggaacc | 1440 |
| gtcgagatca cctgctccgg gggtggctat aggtatggct ggttccagca gaagtctcct | 1500 |
| ggcagtgccc ctgtcacagt gatctactgg gatgatgaca cgccaacag accctcgaac | 1560 |
| atcccttcac gattctccgg ttccacatct ggctccacag ccacattaac catcactggg | 1620 |
| gtccaagccg acgacgaggc tgtctatttc tgtgggagct atgacaggag tagtggttat | 1680 |
| gtttctatat ttggggccgg gacaaccctg accgtcctag ccagccc | 1728 |

<210> SEQ ID NO 55
<211> LENGTH: 1707
<212> TYPE: DNA
<213> ORGANISM: Artificial Sequence
<220> FEATURE:
<223> OTHER INFORMATION: Description of Artificial Sequence: precursor fusion protein comprising chitinase - linker - scFv VD2.

<400> SEQUENCE: 55

| | |
|---|---|
| atggagcagt gcggctcgca ggccggcggg gcgacgtgcc ccaactgcct ctgctgcagc | 60 |
| aagttcggct tctgcggctc cacctccgac tactgcggca acggctgcca gagccagtgc | 120 |
| aacggctgca gcgcggcgg caccccggta ccggtaccga cccccaccgg cggcggcgtg | 180 |
| tcctccatta tctcgcagtc gctcttcgac cagatgctgc tgcaccgcaa cgatgcggcg | 240 |
| tgccaggcca aggggttcta caactacggc gcctttgtag ccgccgccaa ctcgttctcg | 300 |
| ggcttcgcga ccacgggtgg cgccgacgtc aggaagcgcg aggtggccgc gttcctcgct | 360 |
| cagacctccc acgagaccac cggcgggtgg ccaacggcgc ccgacggccc ctactcgtgg | 420 |
| ggctactgct tcaaccagga gcgcggcgcc gcctccgact actgctcgcc gaactcacag | 480 |

```
tggccgtgcg cgccgggcaa gaagtacttc gggcgcgggc ccatccagat ctcatacaac      540
tacaactacg gccggctgg gcgggccatc gggaccgacc tgctcaacaa cccggacctc      600
gtggcgacgg atgcgaccgt gtcgtttaag acggcgctgt ggttctggat gacgccgcag      660
tcacctaaac cttcgagcca cgacgtgatt acggccggt ggagccctc gggcgccgac      720 caggcggcgg ggagggtgcc tgggtacggt gtgatcacta acatcatcaa cggtgggctc      780
gagtgcgggc gcgggcagga cggccgtgtt gccgaccgga tcgggttcta caagcgctac      840
tgcgacctac tcggcgtcag ctacggcgac aacctggact gctacaacca gaggccgttc      900
gccgtcgacg tggaggcgg atctggtggc ggtggaagcg cggcccagcc ggccatggcc      960
cagatccagt tggtgcagtc tggacctgag ctgaagaagc ctggagagac agtcaagatc     1020
tcctgcaagg tttctggaga taacttcaca aactatggaa tgcaatgggt gaagcaggct     1080
ccaggaaagg gtttaaagtg gatgggctgg ataaacacct acactggaga ggcaacatat     1140
gctgatgact ccaagggacg gtttgccttc tctttggaaa cctctgccag cactgcctat     1200
ttgcagatca acaacctcaa aaatgaggac acggctacat atttctgtgc aagattttg      1260 ggtaacccgt actatgttat ggactactgg ggtcaaggaa cctcagtcac tgtctctgca     1320
ggtggcggcg gtagcggcgg tggcggttct ggaggcggcg attctgatgt tttgatgacc     1380
cagactccac tctccctgcc tgtcagtctt ggagatcaag cctccatctc ttgcagatct     1440
agtcagaaca ttgtacatag taatggaaac acctatttgc aatggtacct gcagaaacca     1500
ggccagtctc caaagctcct gatctacaaa gcttccaacc gattttctgg ggtcccagcc     1560
aggttcagtg gcagtggatc aggacagat ttcacactca agatcagcag agtggaggct     1620
gaggatctgg gagtttatta ttgctttcaa ggttcacatg ttccgtacac gttcggaggg     1680
gggaccaagt tggaaataaa acgtgct                                          1707
```

<210> SEQ ID NO 56
<211> LENGTH: 960
<212> TYPE: DNA
<213> ORGANISM: Artificial Sequence
<220> FEATURE:
<223> OTHER INFORMATION: Description of Artificial Sequence: precursor fusion protein comprising AG - linker - scFv VD2.

<400> SEQUENCE: 56

```
atggccacct acaacggcaa gtgctacaag aaggacaaca tctgcaagta caaggcccag       60
agcggcaaga ccgctatctg caagtgctac gtcaagaagt gcccaaggga cggagccaag      120
tgcgagttcg acagctacaa gggcaagtgc tactgcgtcg acggtggagg cggatctggt      180
ggcggtggaa gcgcggccca gcggccatg gcccagatcc agttggtgca gtctggacct      240
gagctgaaga agcctggaga cagtcaag atctcctgca aggtttctgg agataacttc      300
acaaactatg gaatgcaatg ggtgaagcag gctccaggaa agggtttaaa gtggatgggc      360
tggataaaca cctacactgg agaggcaaca tatgctgatg actccaaggg acggtttgcc      420
ttctctttgg aaacctctgc cagcactgcc tatttgcaga tcaacaacct caaaaatgag      480
gacacggcta catatttctg tgcaagattt ttgggtaacc cgtactatgt tatggactac      540
tggggtcaag gaacctcagt cactgtctct gcaggtggcg gcggtagcgg cggtggcggt      600
tctggaggcg gcgattctga tgttttgatg acccagactc cactctccct gcctgtcagt      660
cttggagatc aagcctccat ctcttgcaga tctagtcaga acattgtaca tagtaatgga      720
aacacctatt tgcaatggta cctgcagaaa ccaggccagt ctccaaagct cctgatctac      780
```

| aaagcttcca | accgattttc | tggggtccca | gccaggttca | gtggcagtgg | atcagggaca | 840 |
| gatttcacac | tcaagatcag | cagagtggag | gctgaggatc | tgggagttta | ttattgcttt | 900 |
| caaggttcac | atgttccgta | cacgttcgga | gggggaccca | agttggaaat | aaaacgtgct | 960 |

<210> SEQ ID NO 57
<211> LENGTH: 987
<212> TYPE: DNA
<213> ORGANISM: Artificial Sequence
<220> FEATURE:
<223> OTHER INFORMATION: Description of Artificial Sequence: precursor
      fusion protein comprising RS - linker - scFv VDcw.

<400> SEQUENCE: 57

| atggctcaga | agttgtgtca | gaggccaagt | gggacatggt | caggagtctg | tggaaataat | 60 |
| aacgcgtgca | agaatcagtg | cattcgactt | gagaaagcac | gacatgggtc | ttgcaactat | 120 |
| gtcttcccag | ctcacaagtg | tatctgttat | ttcccttgtg | tcgacggtgg | aggcggatct | 180 |
| ggtggcggtg | gaagcgcggc | ccagccggcc | atggccgagg | tgaagcttct | cgagtctgga | 240 |
| cctgagctga | gaagcctgg | agagacggtc | aagatctcct | gcaaggcttc | tgggtatacc | 300 |
| ttcacaaagt | atggaatgaa | ctgggtgaag | caggctccag | gaaagggttt | aaagtggatg | 360 |
| ggctggataa | atacctacac | tggagagcca | acatatgctg | atgacttcaa | gggacggttt | 420 |
| gccttctctt | tggaaacctc | taccagcact | gcctttttgc | agatcaacaa | cctcaaaaat | 480 |
| gaggacacgg | ctacatattt | ctgtgcaaga | tactacggta | tccttacta | cactatggac | 540 |
| tattggggtc | aaggaacttc | actcaccgtc | tcctcaggtg | gcggcggtag | cggcggtggc | 600 |
| ggttctggag | gcggcggttc | tgacattgtg | ctgtcacagt | ctccatcctc | cctagctgtg | 660 |
| tcagttggag | agaaggttac | tatgagctgc | aagtccagtc | agagccttt | atatagtagc | 720 |
| aatcaaaaga | actacttggc | ctggtaccag | cagaaaccag | gcagtctcc | taaactgctg | 780 |
| atttactggg | catccactag | ggaatctggg | gtccctgatc | gcttcacagg | cagtggatct | 840 |
| gggacagatt | tcaccctcac | catcagcagt | gtgaaggctg | aagacctggc | agtttattac | 900 |
| tgtcaacaat | attatagcta | tccattcacg | ttcggctcgg | gacaaagtt | ggaaataaaa | 960 |
| cgggctgatg | ctgcaccaac | tgtatcc | | | | 987 |

<210> SEQ ID NO 58
<211> LENGTH: 951
<212> TYPE: DNA
<213> ORGANISM: Artificial Sequence
<220> FEATURE:
<223> OTHER INFORMATION: Description of Artificial Sequence: precursor
      fusion protein comprising AG - linker - scFv VDM1.

<400> SEQUENCE: 58

| atggccacct | acaacggcaa | gtgctacaag | aaggacaaca | tctgcaagta | caaggcccag | 60 |
| agcggcaaga | ccgctatctg | caagtgctac | gtcaagaagt | gcccaaggga | cggagccaag | 120 |
| tgcgagttcg | acagctacaa | gggcaagtgc | tactgcgtcg | acggtggagg | cggatctggt | 180 |
| ggcggtggaa | gcgcggccca | gccggccatg | gcccaggtgc | agctgaagca | gtcaggagct | 240 |
| gaggtggtga | acctggggc | ttcagtgaag | atatcctgca | aggcctctgg | ctacaggttc | 300 |
| actgaccatg | ctattcactg | ggtgaagcag | aagcctgaac | agggcctgga | atggattgga | 360 |
| tatatttctc | ccggaaatgg | tgatattaag | tacaatgaga | agttcagggg | caaggccaca | 420 |
| ctgactgcag | acaaatcctc | tagcactgcc | tacatgcagc | tcaacagcct | gacatctgag | 480 |
| gattctgcag | tgtatctctg | taaaagatgg | cctggagcgg | ggatggacta | ctggggtcaa | 540 |

```
ggaacctcag tcaccgtctc tgcaggtggc ggcggtagcg gcggtggcgg ttctggaggc    600
ggcggttctg atattgtgat gacccaaaat gagctctcct atcctgtcac ttctggagaa    660
tcagtttcca tctcctgcag gtctagtaag agtctcctat ataaggatgg aagacatac    720 ttgaattggt ttctgcagag accaggacaa tctcctcagc tcctgatcta tttgatgtcc    780
acccgtgcat caggagtctc agaccggttt agtggcagtg gtcaggaac agatttcacc     840 ctggaaatca gtagagtgaa ggctgaggat gtgggtgtgt attactgtca acaacttgta    900
gagtatccgc tcacgttcgg tgctgggacc aagttggagc tgaaacgggc t             951

<210> SEQ ID NO 59
<211> LENGTH: 987
<212> TYPE: DNA
<213> ORGANISM: Artificial Sequence
<220> FEATURE:
<223> OTHER INFORMATION: Description of Artificial Sequence: precursor
      fusion protein comprising RS - linker scFv VDM2.

<400> SEQUENCE: 59
atggctcaga agttgtgtca gaggccaagt gggacatggt caggagtctg tggaaataat     60
aacgcgtgca agaatcagtg cattcgactt gagaaagcac gacatgggtc ttgcaactat    120
gtcttcccag ctcacaagtg tatctgttat ttcccttgtg tcgacggtgg aggcggatct    180
ggtggcggtg aagcgcggc ccagccggcc atggccgagg tgaagcttct cgagtttgga    240
cctgagctga gaagcctgg agagacggtc aagatctcct gcaaggcttc tgggtatacc    300
ttcacaaagt atggaatgaa ctgggtgaag caggctccag aaaggggttt aaagtggatg    360
ggctggataa ataccatacac tggagagcca acatatgctg atgacttcaa gggacggttt    420
gccttctctt tggaaacctc taccagcact gccttttgc agatcaacaa cctcaaaaat    480
gaggacacgg ctacatattt ctgtgcaaga tactacggta atccttacta cactatggac    540
tattggggtc aaggaacttc actcaccgtc tcctcaggtg gcggcggtag cggcggtggc    600
ggttctggag gcggcggttc tgacattgtg ctgtcacagt ctccatcctc cctagctgtg    660
ttagttggag agaaggttac tatgagctgc aagttcagtc agagccttt atatagtagc    720 aatcaaaaga actacttggc ctggtaccag cagaaaccag gcagtctcc taaactgcta    780 atttactggg catccactag ggaatctggg gtccctgatc gcttcacagg cagtggatct    840
ggaacagatt tcaccctcac catcagcagt gtgaaggctg aagacctggc agtttattac    900
tgtcaacaat attatagcta ccattcacg ttcggctcgg gaacaaagtt ggaaataaaa    960
cgggctgatg ctgcaccaac tgtatcc                                        987

<210> SEQ ID NO 60
<211> LENGTH: 1113
<212> TYPE: DNA
<213> ORGANISM: Artificial Sequence
<220> FEATURE:
<223> OTHER INFORMATION: Description of Artificial Sequence: precursor
      fusion protein comprising ACE - linker - scFv PL2.

<400> SEQUENCE: 60
atggcacaga acatatgccc aagggttaat cgaattgtga cacccctgtgt ggcctacgga     60 ctcggaaggg caccaatcgc cccatgctgc agagccctga cgatctacg gtttgtgaat    120 actagaaacc tacgacgtgc tgcatgccgc tgcctcgtag ggtagtgaa ccggaacccc     180 ggtctgagac gaaaccctag atttcagaac attcctcgtg attgtcgcaa caccttgtt    240
```

| | |
|---|---|
| cgtcccttct ggtggcgtcc aagaattcaa tgcggcagga ttaacgtcga cggtggaggc | 300 |
| ggatctggtg gcggtggaag cgcggcccag ccggccatgg ccgatgtaca gcttcaggag | 360 |
| tcgggacctg gcctcgtgaa accttctcag tctctgtctc tcacctgctc tgtcactggc | 420 |
| tactccatca ccagtggtta ttactggaac tggatccggc agtttccagg aaacaaactg | 480 |
| gaatggatgg gctacataag ctacgacggt accaataaca caacccatc tctcaaaaat | 540 |
| cgaatctcca tcactcgtga cgcatctaag aaccagtttt tcctgaagtt gaattctgtg | 600 |
| actactgagg acacagctac atatcactgt gcaagagggg cccctacta tggtaagggg | 660 |
| acctggtttc cttactgggg ccaagggacc ctggtcaccg tctcctcagg ctccacctca | 720 |
| ggctccggta aacctggccc aggggaggga tcaactaagg gcgcgcctga aattgtgctg | 780 |
| acccagtctc catcctccct ggctatgtca gtaggacaga aggtcactat gagctgcaag | 840 |
| tccagtcaga gccttttaaa tagtagcaat caaagaact attggcctg gtaccagcag | 900 |
| aaaccaggac agtctcctaa acttctggta tattttgcat ccactaggga atctggggtc | 960 |
| cctgatcgct tcataggcag tggatctggg acagatttca ctctcaccat cagcagtgtg | 1020 |
| caggctgaag acctggcaga ttacttctgt cagcaacatt atagcactcc tccgacgttc | 1080 |
| ggtggaggca ccaaactgga gatcaaacgg gct | 1113 |

<210> SEQ ID NO 61
<211> LENGTH: 939
<212> TYPE: DNA
<213> ORGANISM: Artificial Sequence
<220> FEATURE:
<223> OTHER INFORMATION: Description of Artificial Sequence: precursor
fusion protein comprising MBP - linker -
scFv PLp9.

<400> SEQUENCE: 61

| | |
|---|---|
| atgggcagga gcggcagggg agagtgcagg aggcaatgcc tcaggaggca cgaaggccag | 60 |
| ccttgggaga cccaggagtg catgaggagg tgcaggagga ggggagtcga cggtggaggc | 120 |
| ggatctggtg gcggtggaag cgcggcccag ccggccatgg ctgccgtgac gttggacgag | 180 |
| tccgggggcg gcctccagac gcccggagga gcgctcagcc tcgtctgcaa ggcctccggg | 240 |
| ttcgacttca gggggtacga gatggcctgg gtgcgacagg cgcccggcaa ggggctggaa | 300 |
| tgggtcgctg ctattagcag tggttataac acaaactacg gggcggcggt gaagggccgt | 360 |
| gccaccatct cgaggaacaa cgggcagagc acagtgaggc tgcagctgaa caacctcagg | 420 |
| gctgaggaca ccgccaccta ctactgcgcc aaaaactcatg gtgattatgg ctgtgctggt | 480 |
| aatgcttggt gttctgctgg taatatcgac gcatggggcc acgggaccga ggtcaccgtc | 540 |
| tcctcaggct ccacctcagg ctccggtaaa cctggcccag ggagggatc aactaagggc | 600 |
| gcgcctgggc tgactcaggc gtcctcggtg tcagcaaacc cgggagaaac cgtcaagatc | 660 |
| acctgctccg ggggtggcag ctatgctgga agttactatt atggctggta ccagcagaag | 720 |
| acacctggca gtgcccctgt cactgtgatc tatagcaacg acaagagacc ctcgaacatc | 780 |
| ccttcacgat tctccggttc cctatccggc tcaacaaaca cattaaccat cactggggtc | 840 |
| caagtcgacg acgaggctgt ctatttctgt ggtgcctacg acaacaatta tgctggtata | 900 |
| tttggggccg ggacaaccct gaccgtccta ggccagccc | 939 |

<210> SEQ ID NO 62
<211> LENGTH: 327
<212> TYPE: PRT
<213> ORGANISM: Artificial Sequence

```
<220> FEATURE:
<223> OTHER INFORMATION: Description of Artificial Sequence: precursor
      fusion protein comprising AG - linker -
      scFv CWPD2.

<400> SEQUENCE: 62

Met Ala Thr Tyr Asn Gly Lys Cys Tyr Lys Lys Asp Asn Ile Cys Lys
1               5                   10                  15

Tyr Lys Ala Gln Ser Gly Lys Thr Ala Ile Cys Lys Cys Tyr Val Lys
            20                  25                  30

Lys Cys Pro Arg Asp Gly Ala Lys Cys Glu Phe Asp Ser Tyr Lys Gly
        35                  40                  45

Lys Cys Tyr Cys Val Asp Gly Gly Gly

<400> SEQUENCE: 63

```
Met Ala Gln Lys Leu Cys Gln Arg Pro Ser Gly Thr Trp Ser Gly Val
  1               5                  10                  15
Cys Gly Asn Asn Ala Cys Lys Asn Gln Cys Ile Arg Leu Glu Lys
             20                  25                  30
Ala Arg His Gly Ser Cys Asn Tyr Val Phe Pro Ala His Lys Cys Ile
             35                  40                  45
Cys Tyr Phe Pro Cys Val Asp Gly Gly Gly Ser Gly Gly Gly Gly
 50                  55                  60
Ser Ala Ala Gln Pro Ala Met Ala Val Thr Leu Asp Glu Ser Gly
 65                  70                  75                  80
Gly Gly Leu Gln Thr Pro Gly Gly Leu Ser Leu Val Cys Lys Gly
                 85                  90                  95
Ser Gly Phe Asp Phe Ser Ser Asp Thr Met Met Trp Val Arg Gln Ala
                100                 105                 110
Pro Gly Lys Gly Leu Glu Phe Val Ala Gly Ile Ser Gly Asp Gly Ser
                115                 120                 125
Asp Thr Asn Tyr Gly Ser Ala Val Lys Gly Arg Ala Thr Ile Ser Arg
                130                 135                 140
Asp Asn Gly Gln Ser Thr Val Arg Leu Gln Leu Asn Asn Leu Arg Ala
145                 150                 155                 160
Glu Asp Thr Ala Thr Tyr Tyr Cys Thr Arg Gly Pro Cys Ser Pro Thr
                165                 170                 175
Lys Asn Cys Ala Ala Asp Arg Ile Asp Ala Trp Gly His Gly Thr Glu
                180                 185                 190
Val Thr Val Ser Ser Gly Ser Thr Ser Gly Ser Gly Lys Pro Gly Pro
                195                 200                 205
Gly Glu Gly Ser Thr Lys Gly Ala Pro Ala Leu Thr Gln Pro Ser Ser
                210                 215                 220
Val Ser Ala Asn Leu Gly Gly Thr Val Glu Ile Thr Cys Ser Gly Gly
225                 230                 235                 240
Gly Tyr Arg Tyr Gly Trp Phe Gln Gln Lys Ser Pro Gly Ser Ala Pro
                245                 250                 255
Val Thr Val Ile Tyr Trp Asp Asp Ser Ala Asn Arg Pro Ser Asn
                260                 265                 270
Ile Pro Ser Arg Phe Ser Gly Ser Thr Ser Gly Ser Thr Ala Thr Leu
                275                 280                 285
Thr Ile Thr Gly Val Gln Ala Asp Asp Glu Ala Val Tyr Phe Cys Gly
                290                 295                 300
Ser Tyr Asp Arg Ser Ser Gly Tyr Val Ser Ile Phe Gly Ala Gly Thr
305                 310                 315                 320
Thr Leu Thr Val Leu Gly Gln Pro
                325
```

<210> SEQ ID NO 64
<211> LENGTH: 327
<212> TYPE: PRT
<213> ORGANISM: Artificial Sequence
<220> FEATURE:
<223> OTHER INFORMATION: Description of Artificial Sequence: precursor fusion protein comprising lactoferricin - linker - scFv CWPD2.

<400> SEQUENCE: 64

Met Gly Arg Arg Arg Arg Ser Val Gln Trp Cys Ala Val Ser Gln Pro

```
  1               5                  10                 15
Glu Ala Thr Lys Cys Phe Gln Trp Gln Arg Asn Met Arg Lys Val Arg
                20                 25                 30

Gly Pro Pro Val Ser Cys Ile Lys Arg Asp Ser Pro Ile Gln Cys Ile
            35                 40                 45

Gln Ala Ile Ala Val Asp Gly Gly Gly Ser Gly Gly Gly Gly Ser
        50                 55                 60

Ala Ala Gln Pro Ala Met Ala Ala Val Thr Leu Asp Glu Ser Gly Gly
65                  70                 75                 80

Gly Leu Gln Thr Pro Gly Gly Leu Ser Leu Val Cys Lys Gly Ser
                85                 90                 95

Gly Phe Asp Phe Ser Ser Asp Thr Met Met Trp Val Arg Gln Ala Pro
                100                105                110

Gly Lys Gly Leu Glu Phe Val Ala Gly Ile Ser Gly Asp Gly Ser Asp
            115                120                125

Thr Asn Tyr Gly Ser Ala Val Lys Gly Arg Ala Thr Ile Ser Arg Asp
        130                135                140

Asn Gly Gln Ser Thr Val Arg Leu Gln Leu Asn Asn Leu Arg Ala Glu
145                 150                155                160

Asp Thr Ala Thr Tyr Tyr Cys Thr Arg Gly Pro Cys Ser Pro Thr Lys
                165                170                175

Asn Cys Ala Ala Asp Arg Ile Asp Ala Trp Gly His Gly Thr Glu Val
            180                185                190

Thr Val Ser Ser Gly Ser Thr Ser Gly Ser Gly Lys Pro Gly Pro Gly
        195                200                205

Glu Gly Ser Thr Lys Gly Ala Pro Ala Leu Thr Gln Pro Ser Ser Val
    210                215                220

Ser Ala Asn Leu Gly Gly Thr Val Glu Ile Thr Cys Ser Gly Gly
225                 230                235                240

Tyr Arg Tyr Gly Trp Phe Gln Gln Lys Ser Pro Gly Ser Ala Pro Val
                245                250                255

Thr Val Ile Tyr Trp Asp Asp Asp Ser Ala Asn Arg Pro Ser Asn Ile
            260                265                270

Pro Ser Arg Phe Ser Gly Ser Thr Ser Gly Ser Thr Ala Thr Leu Thr
        275                280                285

Ile Thr Gly Val Gln Ala Asp Asp Glu Ala Val Tyr Phe Cys Gly Ser
    290                295                300

Tyr Asp Arg Ser Ser Gly Tyr Val Ser Ile Phe Gly Ala Gly Thr Thr
305                 310                315                320

Leu Thr Val Leu Gly Gln Pro
                325

<210> SEQ ID NO 65
<211> LENGTH: 576
<212> TYPE: PRT
<213> ORGANISM: Artificial Sequence
<220> FEATURE:
<223> OTHER INFORMATION: Description of Artificial Sequence: precursor
      fusion protein comprising chitinase - linker -
      scFv CWPD2.

<400> SEQUENCE: 65

Met Glu Gln Cys Gly Ser Gln Ala Gly Gly Ala Thr Cys Pro Asn Cys
 1               5                  10                 15

Leu Cys Cys Ser Lys Phe Gly Phe Cys Gly Ser Thr Ser Asp Tyr Cys
                20                 25                 30
```

-continued

```
Gly Asn Gly Cys Gln Ser Gln Cys Asn Gly Cys Ser Gly Gly Gly Thr
            35                  40                  45
Pro Val Pro Val Pro Thr Pro Thr Gly Gly Gly Val Ser Ser Ile Ile
 50                  55                  60
Ser Gln Ser Leu Phe Asp Gln Met Leu Leu His Arg Asn Asp Ala Ala
 65                  70                  75                  80
Cys Gln Ala Lys Gly Phe Tyr Asn Tyr Gly Ala Phe Val Ala Ala Ala
                85                  90                  95
Asn Ser Phe Ser Gly Phe Ala Thr Thr Gly Gly Ala Asp Val Arg Lys
                100                 105                 110
Arg Glu Val Ala Ala Phe Leu Ala Gln Thr Ser His Glu Thr Thr Gly
                115                 120                 125
Gly Trp Pro Thr Ala Pro Asp Gly Pro Tyr Ser Trp Gly Tyr Cys Phe
            130                 135                 140
Asn Gln Glu Arg Gly Ala Ala Ser Asp Tyr Cys Ser Pro Asn Ser Gln
145                 150                 155                 160
Trp Pro Cys Ala Pro Gly Lys Lys Tyr Phe Gly Arg Gly Pro Ile Gln
                165                 170                 175
Ile Ser Tyr Asn Tyr Asn Tyr Gly Pro Ala Gly Arg Ala Ile Gly Thr
                180                 185                 190
Asp Leu Leu Asn Asn Pro Asp Leu Val Ala Thr Asp Ala Thr Val Ser
            195                 200                 205
Phe Lys Thr Ala Leu Trp Phe Trp Met Thr Pro Gln Ser Pro Lys Pro
 210                 215                 220
Ser Ser His Asp Val Ile Thr Gly Arg Trp Ser Pro Ser Gly Ala Asp
225                 230                 235                 240
Gln Ala Ala Gly Arg Val Pro Gly Tyr Gly Val Ile Thr Asn Ile Ile
                245                 250                 255
Asn Gly Gly Leu Glu Cys Gly Arg Gly Gln Asp Gly Arg Val Ala Asp
                260                 265                 270
Arg Ile Gly Phe Tyr Lys Arg Tyr Cys Asp Leu Leu Gly Val Ser Tyr
            275                 280                 285
Gly Asp Asn Leu Asp Cys Tyr Asn Gln Arg Pro Phe Ala Val Asp Gly
            290                 295                 300
Gly Gly Gly Ser Gly Gly Gly Ser Ala Ala Gln Pro Ala Met Ala
305                 310                 315                 320
Ala Val Thr Leu Asp Glu Ser Gly Gly Leu Gln Thr Pro Gly Gly
                325                 330                 335
Gly Leu Ser Leu Val Cys Lys Gly Ser Gly Phe Asp Phe Ser Ser Asp
            340                 345                 350
Thr Met Met Trp Val Arg Gln Ala Pro Gly Lys Gly Leu Glu Phe Val
            355                 360                 365
Ala Gly Ile Ser Gly Asp Gly Ser Asp Thr Asn Tyr Gly Ser Ala Val
            370                 375                 380
Lys Gly Arg Ala Thr Ile Ser Arg Asp Asn Gly Gln Ser Thr Val Arg
385                 390                 395                 400
Leu Gln Leu Asn Asn Leu Arg Ala Glu Asp Thr Ala Thr Tyr Tyr Cys
                405                 410                 415
Thr Arg Gly Pro Cys Ser Pro Thr Lys Asn Cys Ala Ala Asp Arg Ile
                420                 425                 430
Asp Ala Trp Gly His Gly Thr Glu Val Thr Val Ser Ser Gly Ser Thr
            435                 440                 445
```

```
Ser Gly Ser Gly Lys Pro Gly Pro Gly Glu Gly Ser Thr Lys Gly Ala
    450                 455                 460

Pro Ala Leu Thr Gln Pro Ser Ser Val Ser Ala Asn Leu Gly Gly Thr
465                 470                 475                 480

Val Glu Ile Thr Cys Ser Gly Gly Tyr Arg Tyr Gly Trp Phe Gln
                485                 490                 495

Gln Lys Ser Pro Gly Ser Ala Pro Val Thr Val Ile Tyr Trp Asp Asp
                500                 505                 510

Asp Ser Ala Asn Arg Pro Ser Asn Ile Pro Ser Arg Phe Ser Gly Ser
            515                 520                 525

Thr Ser Gly Ser Thr Ala Thr Leu Thr Ile Thr Gly Val Gln Ala Asp
    530                 535                 540

Asp Glu Ala Val Tyr Phe Cys Gly Ser Tyr Asp Arg Ser Ser Gly Tyr
545                 550                 555                 560

Val Ser Ile Phe Gly Ala Gly Thr Thr Leu Thr Val Leu Gly Gln Pro
                565                 570                 575

<210> SEQ ID NO 66
<211> LENGTH: 569
<212> TYPE: PRT
<213> ORGANISM: Artificial Sequence
<220> FEATURE:
<223> OTHER INFORMATION: Description of Artificial Sequence: precursor
      fusion protein comprising chitinase - linker -
      scFv VD2.

<400> SEQUENCE: 66

Met Glu Gln Cys Gly Ser Gln Ala Gly Gly Ala Thr Cys Pro Asn Cys
  1               5                  10                  15

Leu Cys Cys Ser Lys Phe Gly Phe Cys Gly Ser Thr Ser Asp Tyr Cys
                20                  25                  30

Gly Asn Gly Cys Gln Ser Gln Cys Asn Gly Cys Ser Gly Gly Gly Thr
            35                  40                  45

Pro Val Pro Val Pro Thr Pro Thr Gly Gly Gly Val Ser Ser Ile Ile
    50                  55                  60

Ser Gln Ser Leu Phe Asp Gln Met Leu Leu His Arg Asn Asp Ala Ala
65                  70                  75                  80

Cys Gln Ala Lys Gly Phe Tyr Asn Tyr Gly Ala Phe Val Ala Ala Ala
                85                  90                  95

Asn Ser Phe Ser Gly Phe Ala Thr Thr Gly Gly Ala Asp Val Arg Lys
            100                 105                 110

Arg Glu Val Ala Ala Phe Leu Ala Gln Thr Ser His Glu Thr Thr Gly
        115                 120                 125

Gly Trp Pro Thr Ala Pro Asp Gly Pro Tyr Ser Trp Gly Tyr Cys Phe
    130                 135                 140

Asn Gln Glu Arg Gly Ala Ala Ser Asp Tyr Cys Ser Pro Asn Ser Gln
145                 150                 155                 160

Trp Pro Cys Ala Pro Gly Lys Lys Tyr Phe Gly Arg Gly Pro Ile Gln
                165                 170                 175

Ile Ser Tyr Asn Tyr Asn Tyr Gly Pro Ala Gly Arg Ala Ile Gly Thr
            180                 185                 190

Asp Leu Leu Asn Asn Pro Asp Leu Val Ala Thr Asp Ala Thr Val Ser
        195                 200                 205

Phe Lys Thr Ala Leu Trp Phe Trp Met Thr Pro Gln Ser Pro Lys Pro
    210                 215                 220

Ser Ser His Asp Val Ile Thr Gly Arg Trp Ser Pro Ser Gly Ala Asp
```

```
                225                 230                 235                 240
Gln Ala Ala Gly Arg Val Pro Gly Tyr Gly Val Ile Thr Asn Ile Ile
                    245                 250                 255
Asn Gly Gly Leu Glu Cys Gly Arg Gly Gln Asp Gly Arg Val Ala Asp
                260                 265                 270
Arg Ile Gly Phe Tyr Lys Arg Tyr Cys Asp Leu Leu Gly Val Ser Tyr
            275                 280                 285
Gly Asp Asn Leu Asp Cys Tyr Asn Gln Arg Pro Phe Ala Val Asp Gly
        290                 295                 300
Gly Gly Gly Ser Gly Gly Gly Ser Ala Ala Gln Pro Ala Met Ala
305                 310                 315                 320
Gln Ile Gln Leu Val Gln Ser Gly Pro Glu Leu Lys Lys Pro Gly Glu
                    325                 330                 335
Thr Val Lys Ile Ser Cys Lys Val Ser Gly Asp Asn Phe Thr Asn Tyr
                340                 345                 350
Gly Met Gln Trp Val Lys Gln Ala Pro Gly Lys Gly Leu Lys Trp Met
            355                 360                 365
Gly Trp Ile Asn Thr Tyr Thr Gly Glu Ala Thr Tyr Ala Asp Asp Ser
        370                 375                 380
Lys Gly Arg Phe Ala Phe Ser Leu Glu Thr Ser Ala Ser Thr Ala Tyr
385                 390                 395                 400
Leu Gln Ile Asn Asn Leu Lys Asn Glu Asp Thr Ala Thr Tyr Phe Cys
                    405                 410                 415
Ala Arg Phe Leu Gly Asn Pro Tyr Tyr Val Met Asp Tyr Trp Gly Gln
                420                 425                 430
Gly Thr Ser Val Thr Val Ser Ala Gly Gly Gly Ser Gly Gly Gly
            435                 440                 445
Gly Ser Gly Gly Gly Asp Ser Asp Val Leu Met Thr Gln Thr Pro Leu
        450                 455                 460
Ser Leu Pro Val Ser Leu Gly Asp Gln Ala Ser Ile Ser Cys Arg Ser
465                 470                 475                 480
Ser Gln Asn Ile Val His Ser Asn Gly Asn Thr Tyr Leu Gln Trp Tyr
                    485                 490                 495
Leu Gln Lys Pro Gly Gln Ser Pro Lys Leu Leu Ile Tyr Lys Ala Ser
                500                 505                 510
Asn Arg Phe Ser Gly Val Pro Ala Arg Phe Ser Gly Ser Gly Ser Gly
            515                 520                 525
Thr Asp Phe Thr Leu Lys Ile Ser Arg Val Glu Ala Glu Asp Leu Gly
        530                 535                 540
Val Tyr Tyr Cys Phe Gln Gly Ser His Val Pro Tyr Thr Phe Gly Gly
545                 550                 555                 560
Gly Thr Lys Leu Glu Ile Lys Arg Ala
                565

<210> SEQ ID NO 67
<211> LENGTH: 320
<212> TYPE: PRT
<213> ORGANISM: Artificial Sequence
<220> FEATURE:
<223> OTHER INFORMATION: Description of Artificial Sequence: precursor
      fusion protein comprising AG - linker - scFv VD2.

<400> SEQUENCE: 67

Met Ala Thr Tyr Asn Gly Lys Cys Tyr Lys Lys Asp Asn Ile Cys Lys
 1               5                   10                  15
```

```
Tyr Lys Ala Gln Ser Gly Lys Thr Ala Ile Cys Lys Cys Tyr Val Lys
             20                  25                  30

Lys Cys Pro Arg Asp Gly Ala Lys Cys Glu Phe Asp Ser Tyr Lys Gly
             35                  40                  45

Lys Cys Tyr Cys Val Asp Gly Gly Gly Ser Gly Gly Gly Gly Ser
 50                  55                  60

Ala Ala Gln Pro Ala Met Ala Gln Ile Gln Leu Val Gln Ser Gly Pro
 65                  70                  75                  80

Glu Leu Lys Lys Pro Gly Glu Thr Val Lys Ile Ser Cys Lys Val Ser
             85                  90                  95

Gly Asp Asn Phe Thr Asn Tyr Gly Met Gln Trp Val Lys Gln Ala Pro
            100                 105                 110

Gly Lys Gly Leu Lys Trp Met Gly Trp Ile Asn Thr Tyr Thr Gly Glu
            115                 120                 125

Ala Thr Tyr Ala Asp Asp Ser Lys Gly Arg Phe Ala Phe Ser Leu Glu
130                 135                 140

Thr Ser Ala Ser Thr Ala Tyr Leu Gln Ile Asn Asn Leu Lys Asn Glu
145                 150                 155                 160

Asp Thr Ala Thr Tyr Phe Cys Ala Arg Phe Leu Gly Asn Pro Tyr Tyr
                165                 170                 175

Val Met Asp Tyr Trp Gly Gln Gly Thr Ser Val Thr Val Ser Ala Gly
            180                 185                 190

Gly Gly Gly Ser Gly Gly Gly Gly Ser Gly Gly Gly Asp Ser Asp Val
            195                 200                 205

Leu Met Thr Gln Thr Pro Leu Ser Leu Pro Val Ser Leu Gly Asp Gln
    210                 215                 220

Ala Ser Ile Ser Cys Arg Ser Gln Asn Ile Val His Ser Asn Gly
225                 230                 235                 240

Asn Thr Tyr Leu Gln Trp Tyr Leu Gln Lys Pro Gly Gln Ser Pro Lys
                245                 250                 255

Leu Leu Ile Tyr Lys Ala Ser Asn Arg Phe Ser Gly Val Pro Ala Arg
                260                 265                 270

Phe Ser Gly Ser Gly Ser Gly Thr Asp Phe Thr Leu Lys Ile Ser Arg
            275                 280                 285

Val Glu Ala Glu Asp Leu Gly Val Tyr Tyr Cys Phe Gln Gly Ser His
    290                 295                 300

Val Pro Tyr Thr Phe Gly Gly Gly Thr Lys Leu Glu Ile Lys Arg Ala
305                 310                 315                 320

<210> SEQ ID NO 68
<211> LENGTH: 329
<212> TYPE: PRT
<213> ORGANISM: Artificial Sequence
<220> FEATURE:
<223> OTHER INFORMATION: Description of Artificial Sequence: precursor
      fusion protein comprising RS - linker scFv VD2.

<400> SEQUENCE: 68

Met Ala Gln Lys Leu Cys Gln Arg Pro Ser Gly Thr Trp Ser Gly Val
 1               5                  10                  15

Cys Gly Asn Asn Asn Ala Cys Lys Asn Gln Cys Ile Arg Leu Glu Lys
             20                  25                  30

Ala Arg His Gly Ser Cys Asn Tyr Val Phe Pro Ala His Lys Cys Ile
         35                  40                  45

Cys Tyr Phe Pro Cys Val Asp Gly Gly Gly Ser Gly Gly Gly Gly
 50                  55                  60
```

```
Ser Ala Ala Gln Pro Ala Met Ala Glu Val Lys Leu Leu Glu Ser Gly
65                  70                  75                  80

Pro Glu Leu Lys Lys Pro Gly Glu Thr Val Lys Ile Ser Cys Lys Ala
                85                  90                  95

Ser Gly Tyr Thr Phe Thr Lys Tyr Gly Met Asn Trp Val Lys Gln Ala
            100                 105                 110

Pro Gly Lys Gly Leu Lys Trp Met Gly Trp Ile Asn Thr Tyr Thr Gly
        115                 120                 125

Glu Pro Thr Tyr Ala Asp Asp Phe Lys Gly Arg Phe Ala Phe Ser Leu
    130                 135                 140

Glu Thr Ser Thr Ser Thr Ala Phe Leu Gln Ile Asn Asn Leu Lys Asn
145                 150                 155                 160

Glu Asp Thr Ala Thr Tyr Phe Cys Ala Arg Tyr Tyr Gly Asn Pro Tyr
                165                 170                 175

Tyr Thr Met Asp Tyr Trp Gly Gln Gly Thr Ser Leu Thr Val Ser Ser
            180                 185                 190

Gly Gly Gly Gly Ser Gly Gly Gly Ser Gly Gly Gly Gly Ser Asp
        195                 200                 205

Ile Val Leu Ser Gln Ser Pro Ser Ser Leu Ala Val Ser Val Gly Glu
    210                 215                 220

Lys Val Thr Met Ser Cys Lys Ser Ser Gln Ser Leu Leu Tyr Ser Ser
225                 230                 235                 240

Asn Gln Lys Asn Tyr Leu Ala Trp Tyr Gln Gln Lys Pro Gly Gln Ser
                245                 250                 255

Pro Lys Leu Leu Ile Tyr Trp Ala Ser Thr Arg Glu Ser Gly Val Pro
            260                 265                 270

Asp Arg Phe Thr Gly Ser Gly Ser Gly Thr Asp Phe Thr Leu Thr Ile
        275                 280                 285

Ser Ser Val Lys Ala Glu Asp Leu Ala Val Tyr Tyr Cys Gln Gln Tyr
290                 295                 300

Tyr Ser Tyr Pro Phe Thr Phe Gly Ser Gly Thr Lys Leu Glu Ile Lys
305                 310                 315                 320

Arg Ala Asp Ala Ala Pro Thr Val Ser
                325

<210> SEQ ID NO 69
<211> LENGTH: 317
<212> TYPE: PRT
<213> ORGANISM: Artificial Sequence
<220> FEATURE:
<223> OTHER INFORMATION: Description of Artificial Sequence: precursor
      fusion protein comprising AG - linker - scFv VDM1.

<400> SEQUENCE: 69

Met Ala Thr Tyr Asn Gly Lys Cys Tyr Lys Lys Asp Asn Ile Cys Lys
1               5                   10

-continued

```
                    85                  90                  95
Gly Tyr Arg Phe Thr Asp His Ala Ile His Trp Val Lys Gln Lys Pro
                100                 105                 110
Glu Gln Gly Leu Glu Trp Ile Gly Tyr Ile Ser Pro Gly Asn Gly Asp
            115                 120                 125
Ile Lys Tyr Asn Glu Lys Phe Arg Gly Lys Ala Thr Leu Thr Ala Asp
        130                 135                 140
Lys Ser Ser Ser Thr Ala Tyr Met Gln Leu Asn Ser Leu Thr Ser Glu
145                 150                 155                 160
Asp Ser Ala Val Tyr Leu Cys Lys Arg Trp Pro Gly Ala Gly Met Asp
                165                 170                 175
Tyr Trp Gly Gln Gly Thr Ser Val Thr Val Ser Ala Gly Gly Gly Gly
            180                 185                 190
Ser Gly Gly Gly Gly Ser Gly Gly Gly Gly Ser Asp Ile Val Met Thr
        195                 200                 205
Gln Asn Glu Leu Ser Tyr Pro Val Thr Ser Gly Glu Ser Val Ser Ile
    210                 215                 220
Ser Cys Arg Ser Ser Lys Ser Leu Leu Tyr Lys Asp Gly Lys Thr Tyr
225                 230                 235                 240
Leu Asn Trp Phe Leu Gln Arg Pro Gly Gln Ser Pro Gln Leu Leu Ile
                245                 250                 255
Tyr Leu Met Ser Thr Arg Ala Ser Gly Val Ser Asp Arg Phe Ser Gly
            260                 265                 270
Ser Gly Ser Gly Thr Asp Phe Thr Leu Glu Ile Ser Arg Val Lys Ala
        275                 280                 285
Glu Asp Val Gly Val Tyr Tyr Cys Gln Gln Leu Val Glu Tyr Pro Leu
    290                 295                 300
Thr Phe Gly Ala Gly Thr Lys Leu Glu Leu Lys Arg Ala
305                 310                 315
```

<210> SEQ ID NO 70
<211> LENGTH: 329
<212> TYPE: PRT
<213> ORGANISM: Artificial Sequence
<220> FEATURE:
<223> OTHER INFORMATION: Description of Artificial Sequence: precursor
      fusion protein comprising RS - linker - scFv VDM2.

<400> SEQUENCE: 70

```
Met Ala Gln Lys Leu Cys Gln Arg Pro Ser Gly Thr Trp Ser Gly Val
1               5                   10                  15
Cys Gly Asn Asn Asn Ala Cys Lys Asn Gln Cys Ile Arg Leu Glu Lys
            20                  25                  30
Ala Arg His Gly Ser Cys Asn Tyr Val Phe Pro Ala His Lys Cys Ile
        35                  40                  45
Cys Tyr Phe Pro Cys Val Asp Gly Gly Gly Ser Gly Gly Gly Gly
    50                  55                  60
Ser Ala Ala Gln Pro Ala Met Ala Glu Val Lys Leu Leu Glu Phe Gly
65                  70                  75                  80
Pro Glu Leu Lys Lys Pro Gly Glu Thr Val Lys Ile Ser Cys Lys Ala
                85                  90                  95
Ser Gly Tyr Thr Phe Thr Lys Tyr Gly Met Asn Trp Val Lys Gln Ala
                100                 105                 110
Pro Gly Lys Gly Leu Lys Trp Met Gly Trp Ile Asn Thr Tyr Thr Gly
            115                 120                 125
```

-continued

```
Glu Pro Thr Tyr Ala Asp Asp Phe Lys Gly Arg Phe Ala Phe Ser Leu
        130                 135                 140

Glu Thr Ser Thr Ser Thr Ala Phe Leu Gln Ile Asn Asn Leu Lys Asn
145                 150                 155                 160

Glu Asp Thr Ala Thr Tyr Phe Cys Ala Arg Tyr Tyr Gly Asn Pro Tyr
                165                 170                 175

Tyr Thr Met Asp Tyr Trp Gly Gln Gly Thr Ser Leu Thr Val Ser Ser
            180                 185                 190

Gly Gly Gly Gly Ser Gly Gly Gly Ser Gly Gly Gly Ser Asp
        195                 200                 205

Ile Val Leu Ser Gln Ser Pro Ser Ser Leu Ala Val Leu Val Gly Glu
    210                 215                 220

Lys Val Thr Met Ser Cys Lys Phe Ser Gln Ser Leu Leu Tyr Ser Ser
225                 230                 235                 240

Asn Gln Lys Asn Tyr Leu Ala Trp Tyr Gln Gln Lys Pro Gly Gln Ser
                245                 250                 255

Pro Lys Leu Leu Ile Tyr Trp Ala Ser Thr Arg Glu Ser Gly Val Pro
            260                 265                 270

Asp Arg Phe Thr Gly Ser Gly Ser Gly Thr Asp Phe Thr Leu Thr Ile
        275                 280                 285

Ser Ser Val Lys Ala Glu Asp Leu Ala Val Tyr Tyr Cys Gln Gln Tyr
    290                 295                 300

Tyr Ser Tyr Pro Phe Thr Phe Gly Ser Gly Thr Lys Leu Glu Ile Lys
305                 310                 315                 320

Arg Ala Asp Ala Ala Pro Thr Val Ser
                325

<210> SEQ ID NO 71
<211> LENGTH: 371
<212> TYPE: PRT
<213> ORGANISM: Artificial Sequence
<220> FEATURE:
<223> OTHER INFORMATION: Description of Artificial Sequence: precursor
      fusion protein comprising ACE - linker -
      scFv PL2.

<400> SEQUENCE: 71

Met Ala Gln Asn Ile Cys Pro Arg Val Asn Arg Ile Val Thr Pro Cys
1               5                   10                  15

Val Ala Tyr Gly Leu Gly Arg Ala Pro Ile Ala Pro Cys Cys Arg Ala
            20                  25                  30

Leu Asn Asp Leu Arg Phe Val Asn Thr Arg Asn Leu Arg Arg Ala Ala
        35                  40                  45

Cys Arg Cys Leu Val Gly Val Val Asn Arg Asn Pro Gly Leu Arg Arg
    50                  55                  60

Asn Pro Arg Phe Gln Asn Ile Pro Arg Asp Cys Arg Asn Thr Phe Val
65                  70                  75                  80

Arg Pro Phe Trp Trp Arg Pro Arg Ile Gln Cys Gly Arg Ile Asn Val
                85                  90                  95

Asp Gly Gly Gly Gly Ser Gly Gly Gly Ser Ala Ala Gln Pro Ala
            100                 105                 110

Met Ala Asp Val Gln Leu Gln Glu Ser Gly Pro Gly Leu Val Lys Pro
        115                 120                 125

Ser Gln Ser Leu Ser Leu Thr Cys Ser Val Thr Gly Tyr Ser Ile Thr
    130                 135                 140

Ser Gly Tyr Tyr Trp Asn Trp Ile Arg Gln Phe Pro Gly Asn Lys Leu
```

-continued

```
             145                 150                 155                 160
Glu Trp Met Gly Tyr Ile Ser Tyr Asp Gly Thr Asn Asn Asn Pro
                165                 170                 175

Ser Leu Lys Asn Arg Ile Ser Ile Thr Arg Asp Ala Ser Lys Asn Gln
                180                 185                 190

Phe Phe Leu Lys Leu Asn Ser Val Thr Thr Glu Asp Thr Ala Thr Tyr
                195                 200                 205

His Cys Ala Arg Gly Ala Pro Tyr Tyr Gly Lys Gly Thr Trp Phe Pro
                210                 215                 220

Tyr Trp Gly Gln Gly Thr Leu Val Thr Val Ser Ser Gly Ser Thr Ser
225                 230                 235                 240

Gly Ser Gly Lys Pro Gly Pro Gly Glu Gly Ser Thr Lys Gly Ala Pro
                245                 250                 255

Glu Ile Val Leu Thr Gln Ser Pro Ser Ser Leu Ala Met Ser Val Gly
                260                 265                 270

Gln Lys Val Thr Met Ser Cys Lys Ser Ser Gln Ser Leu Leu Asn Ser
                275                 280                 285

Ser Asn Gln Lys Asn Tyr Leu Ala Trp Tyr Gln Gln Lys Pro Gly Gln
                290                 295                 300

Ser Pro Lys Leu Leu Val Tyr Phe Ala Ser Thr Arg Glu Ser Gly Val
305                 310                 315                 320

Pro Asp Arg Phe Ile Gly Ser Gly Ser Gly Thr Asp Phe Thr Leu Thr
                325                 330                 335

Ile Ser Ser Val Gln Ala Glu Asp Leu Ala Asp Tyr Phe Cys Gln Gln
                340                 345                 350

His Tyr Ser Thr Pro Pro Thr Phe Gly Gly Gly Thr Lys Leu Glu Ile
                355                 360                 365

Lys Arg Ala
    370

<210> SEQ ID NO 72
<211> LENGTH: 313
<212> TYPE: PRT
<213> ORGANISM: Artificial Sequence
<220> FEATURE:
<223> OTHER INFORMATION: Description of Artificial Sequence: precursor
      fusion protein comprising MBP - linker -
      scFv PLp9.

<400> SEQUENCE: 72

Met Gly Arg Ser Gly Arg Gly Glu Cys Arg Arg Gln Cys Leu Arg Arg
1               5                   10                  15

His Glu Gly Gln Pro Trp Glu Thr Gln Glu Cys Met Arg Arg Cys Arg
                20                  25                  30

Arg Arg Gly Val Asp Gly Gly Gly Ser Gly Gly Gly Gly Ser Ala
            35                  40                  45

Ala Gln Pro Ala Met Ala Ala Val Thr Leu Asp Glu Ser Gly Gly Gly
        50                  55                  60

Leu Gln Thr Pro Gly Gly Ala Leu Ser Leu Val Cys Lys Ala Ser Gly
65                  70                  75                  80

Phe Asp Phe Lys Gly Tyr Glu Met Ala Trp Val Arg Gln Ala Pro Gly
                85                  90                  95

Lys Gly Leu Glu Trp Val Ala Ala Ile Ser Ser Gly Tyr Asn Thr Asn
                100                 105                 110

Tyr Gly Ala Ala Val Lys Gly Arg Ala Thr Ile Ser Arg Asn Asn Gly
                115                 120                 125
```

```
Gln Ser Thr Val Arg Leu Gln Leu Asn Asn Leu Arg Ala Glu Asp Thr
    130                 135                 140

Ala Thr Tyr Tyr Cys Ala Lys Thr His Gly Asp Tyr Gly Cys Ala Gly
145                 150                 155                 160

Asn Ala Trp Cys Ser Ala Gly Asn Ile Asp Ala Trp Gly His Gly Thr
            165                 170                 175

Glu Val Thr Val Ser Ser Gly Ser Thr Ser Gly Ser Gly Lys Pro Gly
            180                 185                 190

Pro Gly Glu Gly Ser Thr Lys Gly Ala Pro Gly Leu Thr Gln Ala Ser
        195                 200                 205

Ser Val Ser Ala Asn Pro Gly Glu Thr Val Lys Ile Thr Cys Ser Gly
    210                 215                 220

Gly Gly Ser Tyr Ala Gly Ser Tyr Tyr Tyr Gly Trp Tyr Gln Gln Lys
225                 230                 235                 240

Thr Pro Gly Ser Ala Pro Val Thr Val Ile Tyr Ser Asn Asp Lys Arg
                245                 250                 255

Pro Ser Asn Ile Pro Ser Arg Phe Ser Gly Ser Leu Ser Gly Ser Thr
            260                 265                 270

Asn Thr Leu Thr Ile Thr Gly Val Gln Val Asp Asp Glu Ala Val Tyr
    275                 280                 285

Phe Cys Gly Ala Tyr Asp Asn Asn Tyr Ala Gly Ile Phe Gly Ala Gly
    290                 295                 300

Thr Thr Leu Thr Val Leu Gly Gln Pro
305                 310
```